US012751997B2

(12) United States Patent
Yongqing et al.

(10) Patent No.: US 12,751,997 B2
(45) Date of Patent: Oct. 6, 2026

(54) PROTEASE COMPOSITION

(71) Applicant: Anatara Lifesciences Limited, Queensland (AU)

(72) Inventors: Tang Yongqing, Queensland (AU); Michael Leo West, Queensland (AU)

(73) Assignee: Anatara Lifesciences Limited, Queensland (AU)

( * ) Notice: Subject to any disclaimer, the term of this patent is extended or adjusted under 35 U.S.C. 154(b) by 665 days.

(21) Appl. No.: 18/002,227

(22) PCT Filed: Jun. 15, 2021

(86) PCT No.: PCT/IB2021/055237

§ 371 (c)(1),
(2) Date: Dec. 16, 2022

(87) PCT Pub. No.: WO2021/255625

PCT Pub. Date: Dec. 23, 2021

(65) Prior Publication Data

US 2023/0263867 A1 Aug. 24, 2023

(30) Foreign Application Priority Data

Jun. 16, 2020 (AU) ................................ 2020901985

(51) Int. Cl.

| | |
|---|---|
| ***A61K 38/48*** | (2006.01) |
| ***A61K 9/19*** | (2006.01) |
| ***A61K 47/02*** | (2006.01) |
| ***A61K 47/12*** | (2006.01) |
| ***A61K 47/18*** | (2017.01) |
| ***A61K 47/24*** | (2006.01) |
| ***C12N 9/50*** | (2006.01) |

(52) U.S. Cl.
CPC ............ *A61K 38/4873* (2013.01); *A61K 9/19* (2013.01); *A61K 47/02* (2013.01); *A61K 47/12* (2013.01); *A61K 47/183* (2013.01); *A61K 47/24* (2013.01); *C12N 9/63* (2013.01); *C12Y 304/22031* (2013.01)

(58) Field of Classification Search
None
See application file for complete search history.

(56) References Cited

U.S. PATENT DOCUMENTS

2010/0272659 A1* 10/2010 Muller ..................... C12N 9/50 424/59
2018/0264091 A1* 9/2018 Mynott .................... C12N 9/63

FOREIGN PATENT DOCUMENTS

| | | | | |
|---|---|---|---|---|
| EP | 2173868 | B1 | 10/2012 | |
| WO | 2006054309 | A2 | 5/2006 | |
| WO | WO-2010080830 | A1 * | 7/2010 | .............. A61P 31/02 |
| WO | 2013011514 | A1 | 1/2013 | |
| WO | 2017031299 | A1 | 2/2017 | |
| WO | WO2021255625 | A1 | 12/2021 | |

OTHER PUBLICATIONS

International Application Status Report generated on Dec. 12, 2022 in International Application No. PCT/IB2021/055237.
International Search Report mailed Aug. 27, 2021 in International Application No. PCT/IB2021/055237.
Written Opinion mailed on Aug. 27, 2021 in International Application No. PCT/IB2021/055237.
Yongqing Tang et al: "Determination of the crystal structure and substrate specificity of ananain", Biochimie, Masson, Paris, FR, vol. 166, Jul. 12, 2019 (Jul. 12, 2019), pp. 194-202, XP085874424, ISSN: 0300-9084, DOI: 10.1016/J.BIOCHI.2019.07.01 1 [retrieved on Jul. 12, 2019).
Rowan, A. D et al.: "Ananain: A Novel Cysteine Proteinase Found in Pineapple Stem", Archives of Biochemistry and Biophysics, vol. 267, No. 1, 1988, pp. 262-270, XP024761115, DOI: 10.1016/0003-9861(88)90031 -8.
Carter, C.E et al.: "Mutagenesis and Kinetic Studies of a Plant Cysteine Proteinase with an Unusual Arrangement of Acidic Amino Acids in and around the Active Site", Biochemistry, vol. 39, 2000, pp. 11005-11013, XP002472342, DOI: 10.1021 /bi992714w.
European Patent Office, Extended European Search Report in related European Application No. 21825115.5, issued Jul. 1, 2024.
Rowan, A.D. et al.: "Pineapple cysteine endopeptidases", Methods in Enzymology, Academic Press, vol. 244, 1994, pp. 555-568, ISSN 0076-6879, ISBN 9780121821456, DOI: 10.1016/0076-6879(94)44040-9.

* cited by examiner

*Primary Examiner* — Grant C Currens
(74) *Attorney, Agent, or Firm* — Kim IP Law Group LLC

(57) ABSTRACT

This invention disclosed herein relates generally to compositions comprising the cysteine protease ananain, a reducing agent and a buffer. Also disclosed generally herein are methods of stabilizing the cysteine protease, ananain while retaining protease activity, as well as methods of activating ananain zymogen for proteolysis.

18 Claims, 19 Drawing Sheets

Specification includes a Sequence Listing.

```
agctgcgatgagccgagcgacccgatgatgaaacaatttgaagagtggatggcggagtat
 S  C  D  E  P  S  D  P  M  M  K  Q  F  E  E  W  M  A  E  Y
ggccgtgtgtataaggataacgacgagaagatgctgcgtttccagattttcaaaaacaac
 G  R  V  Y  K  D  N  D  E  K  M  L  R  F  Q  I  F  K  N  N
gttaaccacatcgaaaccttcaacaaccgtaacggcaacagctacaccctgggtattaac
V  N  H  I  E  T  F  N  N  R  N  G  N  S  Y  T  L  G  I  N
cagttcaccgacatgaccaacaacgagtttgtggcgcaatataccggtctgagcctgccg
 Q  F  T  D  M  T  N  N  E  F  V  A  Q  Y  T  G  L  S  L  P
ctgaacatcaagcgtgaaccggtggttagcttcgacgatgtggacatcagcagcgtgccg
 L  N  I  K  R  E  P  V  V  S  F  D  D  V  D  I  S  S  V  P
cagagcattgactggcgtgatagcggcgcggtgaccagcgttaaaaaccaaggccgttgc
 Q  S  I  D  W  R  D  S  G  A  V  T  S  V  K  N  Q  G  R  C
ggtagctgctgggcgtttgcgagcattgcgaccgtggagagcatctacaagattaaacgt
 G  S  C  W  A  F  A  S  I  A  T  V  E  S  I  Y  K  I  K  R
ggcaacctggttagcctgagcgaacagcaagtgctggactgcgcggttagctacggttgc
 G  N  L  V  S  L  S  E  Q  Q  V  L  D  C  A  V  S  Y  G  C
aagggtggctggattaacaaagcgtatagctttatcattagcaacaagggcgttgcgagc
 K  G  G  W  I  N  K  A  Y  S  F  I  I  S  N  K  G  V  A  S
gcggcgatctacccgtataaggcggcgaaaggcacctgcaaaaccaacggtgtgccgaac
 A  A  I  Y  P  Y  K  A  A  K  G  T  C  K  T  N  G  V  P  N
agcgcgtacattacccgttacacctatgttcaacgtaacaacgagcgtaacatgatgtat
 S  A  Y  I  T  R  Y  T  Y  V  Q  R  N  N  E  R  N  M  M  Y
gcggtgagcaaccaaccgattgcggcggcgctggacgcgagcggcaacttccaacactac
 A  V  S  N  Q  P  I  A  A  A  L  D  A  S  G  N  F  Q  H  Y
aagcgtggtgtttttaccggtccgtgcggcacccgtctgaaccacgcgatcgtgatcatt
 K  R  G  V  F  T  G  P  C  G  T  R  L  N  H  A  I  V  I  I
ggttatggccaggatagcagcggtaagaaattctggatcgttcgtaacagctggggtgcg
 G  Y  G  Q  D  S  S  G  K  K  F  W  I  V  R  N  S  W  G  A
ggttggggtgaaggtggctacattcgtctggcgcgtgacgtgagcagcagcttcggcctg
 G  W  G  E  G  G  Y  I  R  L  A  R  D  V  S  S  S  F  G  L
tgcggtatcgcgatggacccgctgtatccgaccctgcaaagcggtccgagcgttgaggtt
  C  G  I  A  M  D  P  L  Y  P  T  L  Q  S  G  P  S  V  E  V
atc
 I
```

Figure 1

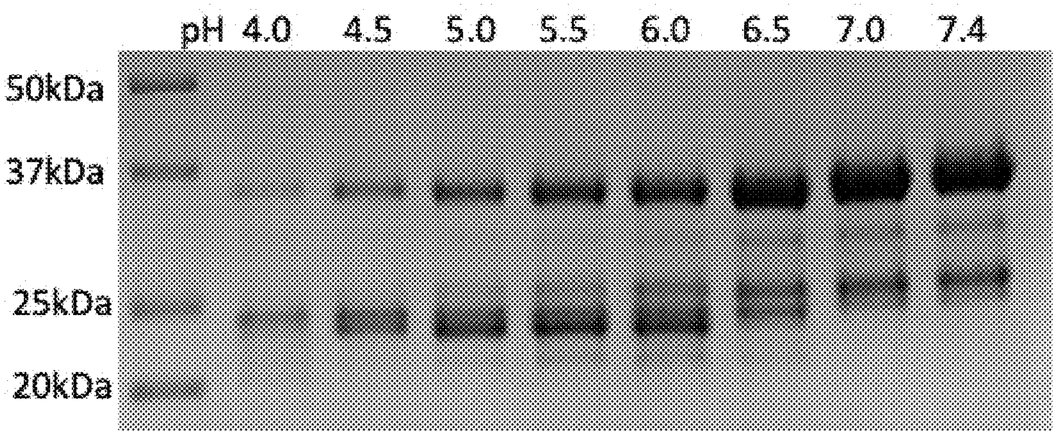

Figure 2

```
agcgcggacgagccgagcgacccgatgatgaagcgttttgaagagtggatggtggagtat
 S   A   D   E   P   S   D   P   M   M   K   R   F   E   E   W   M   V   E   Y
ggccgtgtgtataaagataatgacgagaagatgcgtcgtttccagattttcaaaaacaac
 G   R   V   Y   K   D   N   D   E   K   M   R   R   F   Q   I   F   K   N   N
gttaaccacatcgaaaccttcaacagccgtaacgaaaacagctacaccctgggtatcaac
 V   N   H   I   E   T   F   N   S   R   N   E   N   S   Y   T   L   G   I   N
cagttcaccgacatgaccaacaacgagtttattgcgcaatataccggtggcatcagccgt
 Q   F   T   D   M   T   N   N   E   F   I   A   Q   Y   T   G   G   I   S   R
ccgctgaacattgagcgtgaaccggtggttagcttcgacgatgtggacatcagcgcggtt
 P   L   N   I   E   R   E   P   V   V   S   F   D   D   V   D   I   S   A   V
ccgcagagcattgactggcgtgattacggtgcggtgaccagcgttaagaaccaaaacccg
 P   Q   S   I   D   W   R   D   Y   G   A   V   T   S   V   K   N   Q   N   P
tgcggtgcgtgctgggcgtttgcggcgatcgcgaccgttgaaagcatctacaagattaag
 C   G   A   C   W   A   F   A   A   I   A   T   V   E   S   I   Y   K   I   K
aaaggtattctggagccgctgagcgaacagcaagtgctggactgcgcgaagggttatggc
 K   G   I   L   E   P   L   S   E   Q   Q   V   L   D   C   A   K   G   Y   G
tgcaaaggtggctgggagtttcgtgcgttcgaatttatcattagcaacaagggtgtggcg
 C   K   G   G   W   E   F   R   A   F   E   F   I   I   S   N   K   G   V   A
agcggcgcgatctacccgtataaggcggcgaaaggcacctgcaaaaccaacggcgtgccg
 S   G   A   I   Y   P   Y   K   A   A   K   G   T   C   K   T   N   G   V   P
aacagcgcgtacattaccggttatgcgcgtgttccgcgtaacaacgagagcagcatgatg
 N   S   A   Y   I   T   G   Y   A   R   V   P   R   N   N   E   S   S   M   M
tacgcggtgagcaagcagccgatcaccgtggcggttgacgcgaacgcgaacttccaatac
 Y   A   V   S   K   Q   P   I   T   V   A   V   D   A   N   A   N   F   Q   Y
tataaaagcggcgtttttaacggtccgtgcggcaccagcctgaaccatgcggtgaccgcg
 Y   K   S   G   V   F   N   G   P   C   G   T   S   L   N   H   A   V   T   A
atcggttacggccaagatagcaacggtaagaaatattggattgttaagaacagctggggc
 I   G   Y   G   Q   D   S   N   G   K   K   Y   W   I   V   K   N   S   W   G
gcgcgttggggtgaagcgggctacatccgtatggcgcgtgacgtgagcagcagcagcggt
 A   R   W   G   E   A   G   Y   I   R   M   A   R   D   V   S   S   S   S   G
atttgcggcatcgcgattgatagcctgtatccgaccctggagagccgtgcgaacgtggaa
 I   C   G   I   A   I   D   S   L   Y   P   T   L   E   S   R   A   N   V   E
gcgatcaaaatggttagcgaaagccgcagcagcgtt
 A   I   K   M   V   S   E   S   R   S   S   V
```

Figure 42

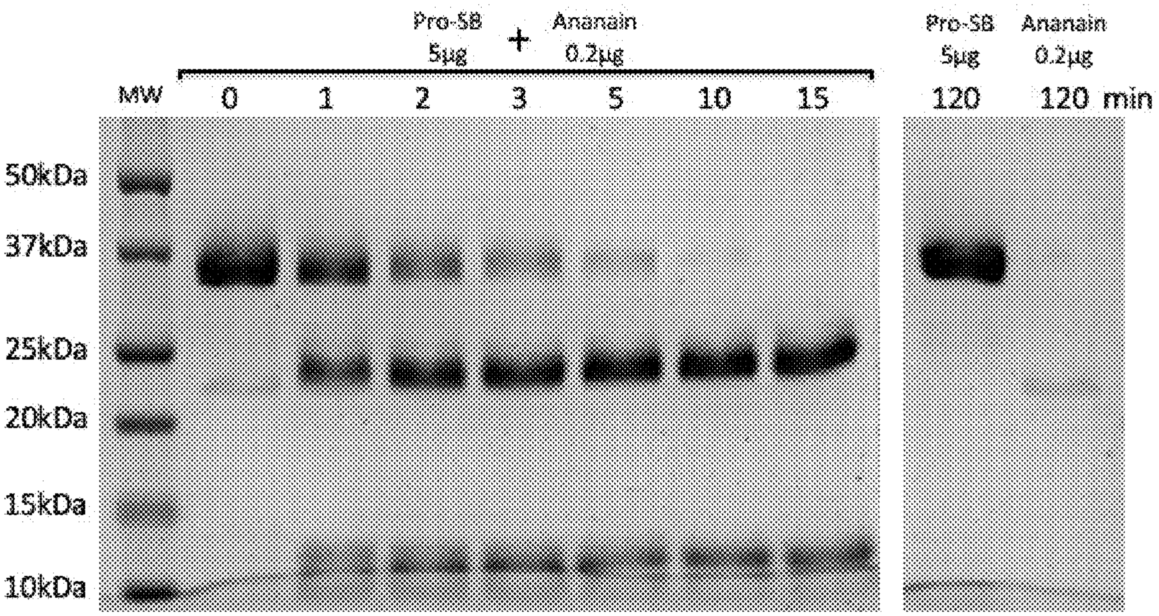

Figure 43

```
tcgccactcgcctcttgcggccaatcggatgctcacatgatgacgaggttcgaagattgg
 S  P  L  A  S  C  G  Q  S  D  A  H  M  M  T  R  F  E  D  W
atgagacaatatggccgagtttacgacagtgaagacgagaagtccctccgttttgagatc
 M  R  Q  Y  G  R  V  Y  D  S  E  D  E  K  S  L  R  F  E  I
tttaagaacaacgtgaaccatatcgaaaccttcaatagccgcaacgaaaactcgtacact
 F  K  N  N  V  N  H  I  E  T  F  N  S  R  N  E  N  S  Y  T
ctcggcattaatcaattcgctgatatgacaaatgaagaattcgttgcgcgatacgctggt
 L  G  I  N  Q  F  A  D  M  T  N  E  E  F  V  A  R  Y  A  G
acgttcttccctcaaaatattgaatcggagccaactgcatcgcttgaggacgtagacttg
 T  F  F  P  Q  N  I  E  S  E  P  T  A  S  L  E  D  V  D  L
tccaaactgcctgatagtattgattggaggcagaaaggtgccgtcacggaagtcaagaat
 S  K  L  P  D  S  I  D  W  R  Q  K  G  A  V  T  E  V  K  N
caaggcgaatgcggttcatgctgggcgttcagtgcagttgcgacagtagaagggctctac
 Q  G  E  C  G  S  C  W  A  F  S  A  V  A  T  V  E  G  L  Y
aagatcaaaaagggaaacttgttagatctatctgaacaagaagttttagactgcgccgac
 K  I  K  K  G  N  L  L  D  L  S  E  Q  E  V  L  D  C  A  D
agcgtcgagtgcataggtggttgggtgcagaatgcctacaaattcatcatatctaataaa
 S  V  E  C  I  G  G  W  V  Q  N  A  Y  K  F  I  I  S  N  K
ggtgtgacaaatgaaaagagctacccttatgtgggaaccaaaggcagttgcgccgcaaag
 G  V  T  N  E  K  S  Y  P  Y  V  G  T  K  G  S  C  A  A  K
ggcaaacccaacgtagcatatattactggttacgaatttctgcctgcgtttgacgaaggc
 G  K  P  N  V  A  Y  I  T  G  Y  E  F  L  P  A  F  D  E  G
accatgatggctgccgtggcgcagcaaccgataacttccgccgtcgatacgaaaaacaag
 T  M  M  A  A  V  A  Q  Q  P  I  T  S  A  V  D  T  K  N  K
aactttcagttttacaatggcggcgtgtttaaaggaccttgcgggacaaggattgaccac
 N  F  Q  F  Y  N  G  G  V  F  K  G  P  C  G  T  R  I  D  H
gccatcaccattgtagggtacgggaaagacagcagcggaacacagtattggttaattaag
 A  I  T  I  V  G  Y  G  K  D  S  S  G  T  Q  Y  W  L  I  K
aactcatggggcaaaacgtggggcgagagcgggtacttgaggctgcaaaagggctccgga
 N  S  W  G  K  T  W  G  E  S  G  Y  L  R  L  Q  K  G  S  G
acattacgcggagcatgtgggatcgcccagtatgtcctccgtccgcttctgaattcgaag
 T  L  R  G  A  C  G  I  A  Q  Y  V  L  R  P  L  L  N  S  K
gcaaccgcccaactctctgacacggggtctgatggtttaagttcgatc
 A  T  A  Q  L  S  D  T  G  S  D  G  L  S  S  I
```

Figure 46

PROTEASE COMPOSITION

CROSS-REFERENCE TO RELATED APPLICATIONS

This application is a U.S. national phase application under 35 U.S.C. § 371 of International Application No. PCT/IB2021/055237, filed Jun. 15, 2021, which claims the benefit of Australian Patent Application No. 2020901985, filed Jun. 16, 2020, the entire disclosures of which are hereby incorporated by reference in their entirety for all purposes.

FIELD OF THE INVENTION

This invention relates generally to a composition comprising the cysteine protease ananain, a reducing agent and a buffer, to methods of stabilizing ananain while retaining protease activity, and methods of activating ananain zymogen for proteolysis.

SEQUENCE LISTING

The instant application contains a Sequence Listing which has been submitted via EFSWeb and is hereby incorporated by reference in its entirety. Said ASCII copy, created on Jan. 22, 2026, is named 1369.0016-16US_ST25, and is 14,173 bytes in size.

BACKGROUND TO THE INVENTION

Ananain

Ananain (EC 3.4.22.31) is a plant cysteine protease in the papain superfamily of cysteine proteases. Ananain has a broad specificity for peptide bonds and catalyzes the hydrolysis of various proteins. Ananain is found in bromelain extract, a proteolytic extract obtained from the stems of pineapple (*Ananus comosus*). Ananain differs from other papain superfamily proteases in comprising a unique combination of acidic amino acids. Ananain is also considered to be an enzyme of considerable commercial importance due to strong proteolytic activity (Yongqing et al. 2019).

As a therapeutic, ananain-rich bromelain fractions have demonstrated utility as immunosuppressants, acting to inhibit the production of various cytokines including interleukin-2 (IL-2), IL-4, IL-6, tumor necrosis factor (TNF) and gamma interferon (INFγ) (WO2017/031299). Ananain-rich bromelain fractions have also been used as debriding agents (Orgill et al. 1996) and been suggested to block ERK-2 phosphorylation and the MAP kinase cascade, and CD4+ T cell proliferation (U.S. Pat. No. 9,963,777). Similar to other proteolytic enzymes (e.g., serine, aspartic and metalloproteases), the use of ananain as a therapeutic requires the prevention of unwanted protein degradation (including unwanted auto-proteolysis or self-degradation (Verma et al. 2016)).

Naturally occurring ananain from natural extracts of pineapple is produced by fractionation of bromelain extract and is known to be unstable, autolysing to constituent peptides and amino acids. In addition, the ananain comprised in fractions of bromelain extract lacks purity (Matagne et al. 2017). In contrast, recombinant ananain produced by in vitro expression in an appropriate host cell can be obtained and formulated into compositions of high purity. Such compositions suffer from an acknowledged lack of stability when formulated for physiological use; i.e., the active form of the enzyme is auto-proteolytic and undergoes a marked loss of activity over a relatively short time (i.e., a few hours). Additionally, freeze drying or alternate forms of formulating pure ananain result in irreversible denaturation of the enzyme such that when reconstituted, the enzyme preparation has lost significant activity.

The expression of an ananain zymogen (pro-ananain) overcomes the inherent instability of the enzyme, however such zymogen forms require activation under conditions of high ionic strength 50 mM, low pH (pH 4.0), and high temperature (55° C.) for 30-60 minutes. These conditions are inconsistent with in vivo use (Carter et al. 2000).

Accordingly, there is an unmet need in the art for compositions comprising pure and stable pro-ananain (i.e., separated from other proteases and/or other constituents), methods of making such compositions and methods of activating pro-ananain under physiologically compatible conditions to obtain mature ananain for various uses as described above.

It is an object of the invention to provide a composition of pure and stable pro-ananain (i.e., separated from other proteases and/or other active constituents), methods of making such compositions and methods of activating pro-ananain to obtain mature ananain that can go at least some way towards addressing this unmet need and/or to at least provide the public with a useful choice.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

In one aspect the invention relates to a composition comprising:

(a) recombinant pro-ananain
(b) a pharmaceutically acceptable buffer
(c) a pharmaceutically acceptable reducing agent, and
(d) sodium chloride (NaCl),
  wherein the concentration of the buffer is about 5 to about 30 mM,
  wherein the concentration of the reducing agent is about 10 to about 30 mM,
  wherein the concentration of the NaCl is about 140 to about 160 mM and,
  wherein the pH of the composition is about 5.0 to about 6.0.

In another aspect the invention relates to a method of making a composition comprising recombinant pro-ananain, the method comprising combining:

(a) recombinant pro-ananain with,
(b) a pharmaceutically acceptable buffer
(c) a pharmaceutically acceptable reducing agent, and
(d) sodium chloride (NaCl),
  wherein the concentration of the buffer is about 5 to about 30 mM,
  wherein the concentration of the reducing agent is about 10 to about 30 mM,
  wherein the concentration of the NaCl is about 140 to about 160 mM and,
  wherein the pH of the composition is about 5.0 to about 6.0.

In another aspect the invention relates to a method of providing a recombinant active ananain composition, the method comprising heating an aqueous composition of the invention to about 30° C. to about 44° C. for at least 5 min.

In another aspect the invention relates to method of providing a recombinant active ananain composition, the method comprising reconstituting a dry composition of the invention to form an aqueous composition and heating the aqueous composition to at least 30° C.

In another aspect the invention relates to an in vivo method of activating bromelain comprising (a) reconstituting a dry composition comprising at least 0.1% recombinant pro-ananain and >about 5% recombinant pro-bromelain and a physiological buffer in water to form an aqueous composition comprising about 4 to about 20 mM buffer, and (b), heating the reconstituted composition in vivo to about 37° C., wherein the reconstituted composition comprises a pH of about 5.0 to about 7.5.

In another aspect the invention relates to a method of activating bromelain comprising (a) reconstituting a dry composition comprising at least 0.1% recombinant pro-ananain and about >5% recombinant pro-bromelain and a physiological buffer in water to form an aqueous composition comprising about 4 to about 20 mM buffer, and (b), heating the aqueous composition in vitro to between about 30° C. and about 40° C. for about 5 to about 20 mins, wherein the reconstituted composition comprises a pH of between about 5 and about 7.5.

Other aspects of the invention may become apparent from the following description which is given by way of example only and with reference to the accompanying drawings.

BRIEF DESCRIPTION OF THE FIGURES

The invention will now be described by way of example only and with reference to the drawings in which:

FIG. 1—The gene and protein sequences of pro-ananain.

Shown in FIG. 1 are the primary amino acid (SEQ ID NO: 1) and nucleic acid (SEQ ID NO: 2) sequences of recombinant pro-ananain used in the work disclosed herein.

FIG. 2—Sodium dodecyl sulfate-polyacrylamide gel electrophoresis (SDS-PAGE) of pro-ananain activation in phosphate citrate buffer at varied pH values.

SDS-PAGE was applied to visualize active ananain resulting from the activation process at different pH values in phosphate-citrate buffer. Pro-ananain and active ananain are displayed as a 36 kDa and a 24 kDa band, respectively, in a 12.5% SDS-gel. Lane 1, molecule weight markers. Lanes 2-9, incubation at various pH values.

Figure 3:
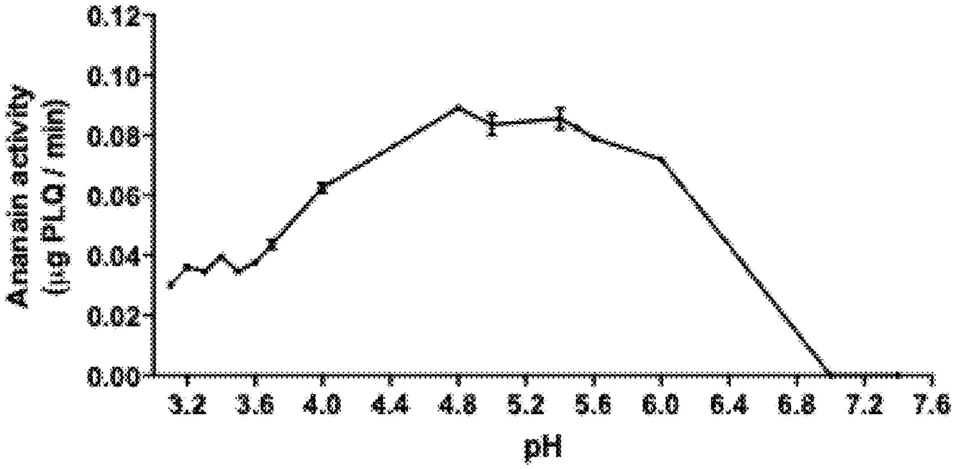

FIG. 3—Activity assay of pro-ananain activation in phosphate citrate buffer at varied pH values.

Graphic representation of the activity of mature ananain resulting from the activation process at different pH values in phosphate-citrate buffer. PLQ is the fluorescent tripeptidyl substrate: MeOC-GGG-PLQ-GG-DPA-KK-$NH_2$ (SEQ ID NO: 7). Cleavage at the core PLQ tripeptide tethered between the fluorescent MeOC donor group and the DPA quencher moiety releases the fluorescence of the MeOC donor group, which is detected by using a POLARstar fluorescent plate reader (BMG Labtech, Offenburg, Germany) with excitation and emission wavelengths of 320 nm and 420 nm, respectively. The initial rate of proteolysis of substrate is measured as the slope of the linear portion of the progressive curve and is converted to the unit of μg PLQ molecules per min.

Figure 4:
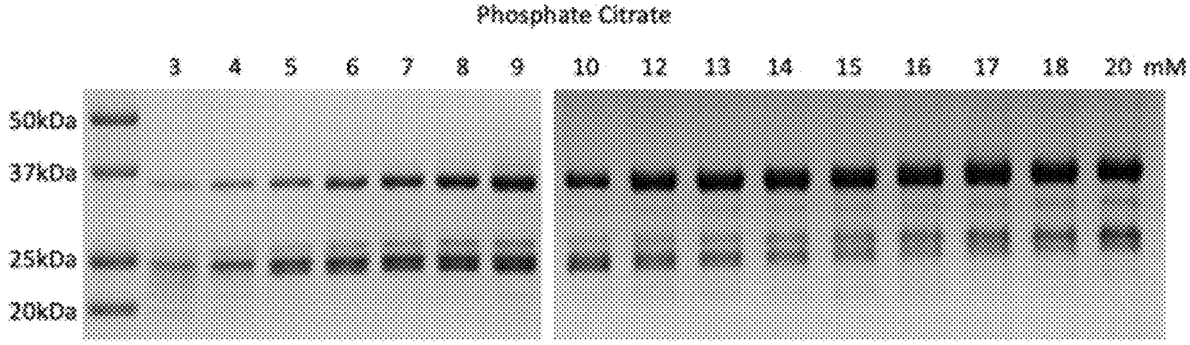

FIG. 4—SDS-PAGE of pro-ananain activation in varied concentrations of phosphate citrate buffer.

SDS-PAGE was applied to visualize active ananain resulting from the activation process in different concentrations of phosphate-citrate buffer. Pro-ananain and active ananain are displayed as a 36 kDa and a 24 kDa band, respectively, in a 12.5% SDS-gel. Lane 1, molecule weight markers. Lanes 2-17, incubation in various concentrations of phosphate citrate buffer.

Figure 5:
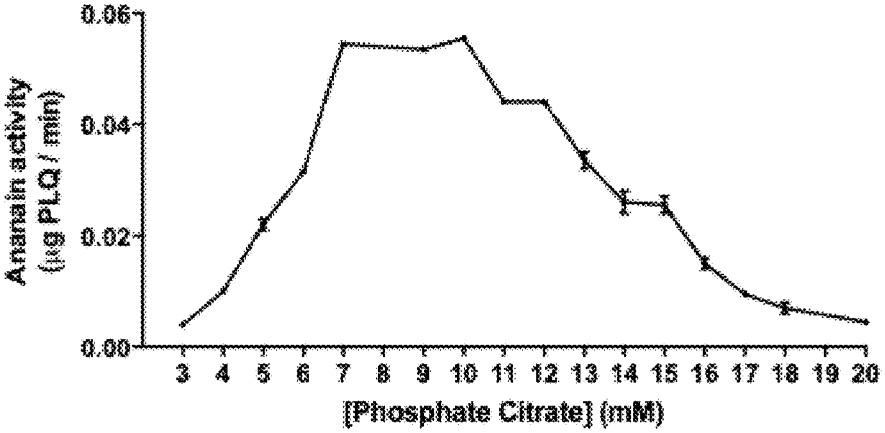

FIG. 5—Activity assay of pro-ananain activation in varied concentrations of phosphate citrate buffer.

Graphic representation of the activity of mature ananain resulting from the activation process in different concentrations of phosphate-citrate buffer. PLQ is the fluorescent tripeptidyl substrate: MeOC-GGG-PLQ-GG-DPA-KK-$NH_2$ (SEQ ID NO: 7). Cleavage at the core PLQ tripeptide tethered between the fluorescent MeOC donor group and the DPA quencher moiety releases the fluorescence of the MeOC donor group, which is detected by using a POLARstar fluorescent plate reader (BMG Labtech, Offenburg, Germany) with excitation and emission wavelengths of 320 nm and 420 nm, respectively. The initial rate of proteolysis of substrate is measured as the slope of the linear portion of the progressive curve and is converted to the unit of μg PLQ molecules per min.

Figure 6:
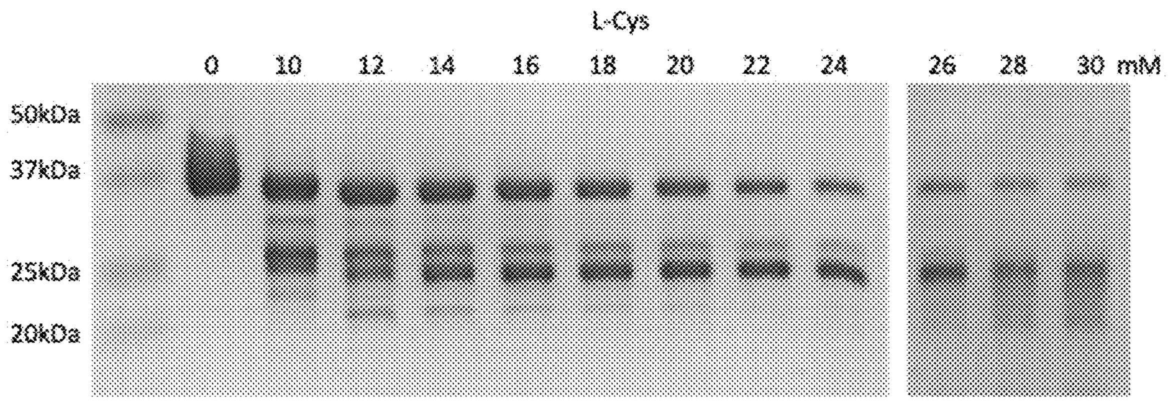

FIG. 6—SDS-PAGE of pro-ananain activation in varied concentrations of L-Cysteine (L-Cys) in phosphate citrate buffer.

SDS-PAGE was applied to visualize active ananain resulting from the activation process in different concentrations of L-Cys in phosphate citrate buffer. Pro-ananain and active ananain are displayed as a 36 kDa and a 24 kDa band, respectively, in a 12.5% SDS-gel. Lane 1, molecule weight markers. Lanes 2-13, incubation in various concentrations of L-Cys.

Figure 7:
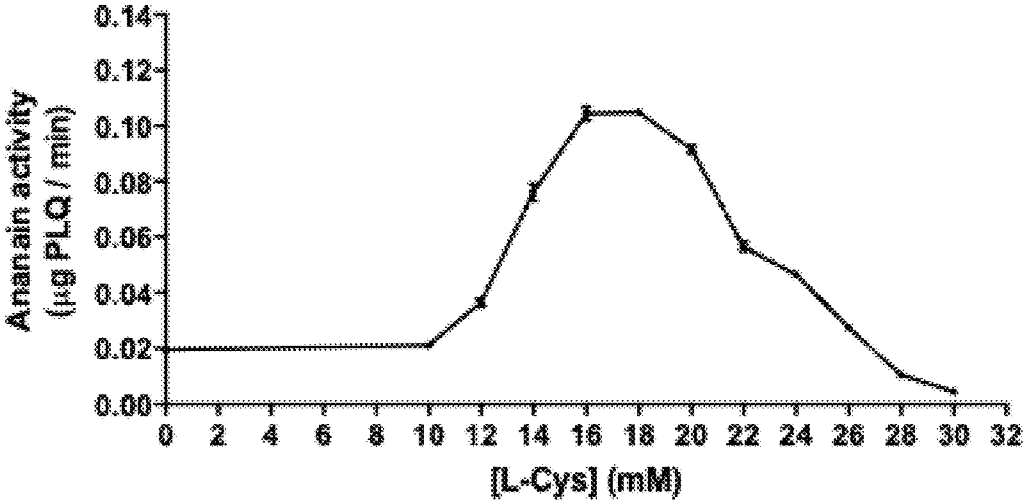

FIG. 7—Activity assay of pro-ananain activation in varied concentrations of L-Cys in phosphate citrate buffer.

Graphic representation of the activity of mature ananain resulting from the activation process in different concentrations of L-Cys in phosphate citrate buffer. PLQ is the fluorescent tripeptidyl substrate: MeOC-GGG-PLQ-GG-DPA-KK-$NH_2$ (SEQ ID NO: 7). Cleavage at the core PLQ tripeptide tethered between the fluorescent MeOC donor group and the DPA quencher moiety releases the fluorescence of the MeOC donor group, which is detected by using a POLARstar fluorescent plate reader (BMG Labtech, Offenburg, Germany) with excitation and emission wavelengths of 320 nm and 420 nm, respectively. The initial rate of proteolysis of substrate is measured as the slope of the linear portion of the progressive curve and is converted to the unit of μg PLQ molecules per min.

Figure 8:
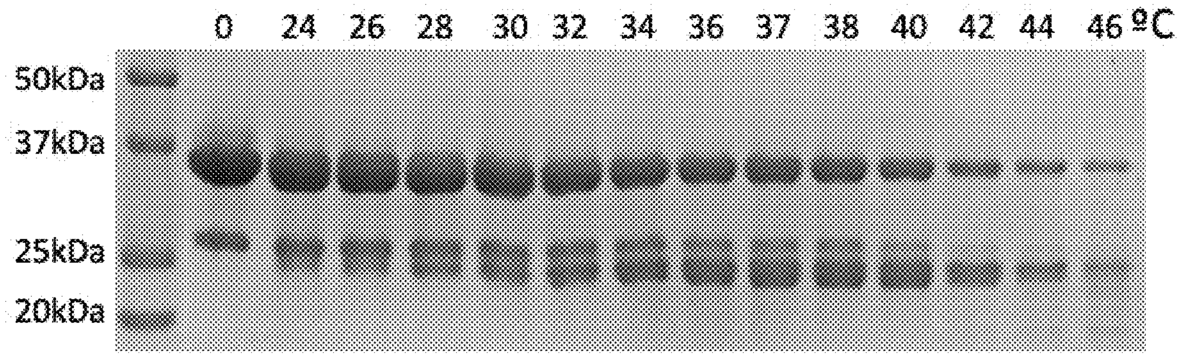

FIG. 8—SDS-PAGE of pro-ananain activation at varied temperatures in phosphate citrate buffer.

SDS-PAGE was applied to visualize active ananain resulting from the activation process at different temperatures between 0 and 46° C. in phosphate citrate buffer. Pro-ananain and active ananain are displayed as a 36 kDa and a 24 kDa band, respectively, in a 12.5% SDS-gel. Lane 1, molecule weight markers. Lanes 2-15, incubation at different temperatures.

Figure 9:
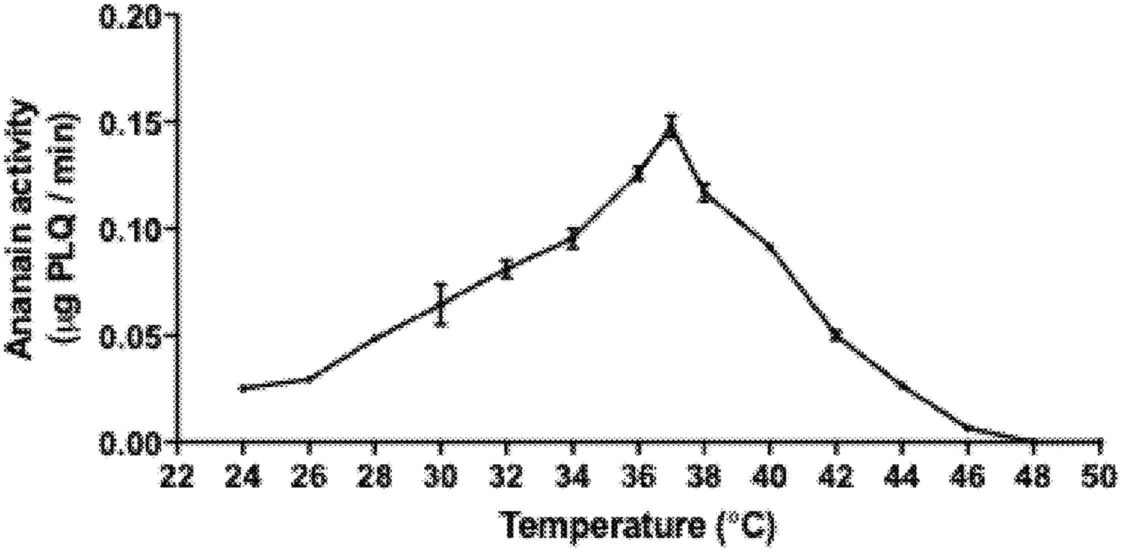

FIG. 9—Activity assay of pro-ananain activation at varied temperatures in phosphate citrate buffer.

Graphic representation of the activity of mature ananain resulting from the activation process at different temperatures between 0 and 50° C. in phosphate citrate buffer. PLQ is the fluorescent tripeptidyl substrate: MeOC-GGG-PLQ-GG-DPA-KK-$NH_2$ (SEQ ID NO: 7). Cleavage at the core PLQ tripeptide tethered between the fluorescent MeOC donor group and the DPA quencher moiety releases the fluorescence of the MeOC donor group, which is detected by using a POLARstar fluorescent plate reader (BMG Labtech, Offenburg, Germany) with excitation and emission wavelengths of 320 nm and 420 nm, respectively. The initial rate of proteolysis of substrate is measured as the slope of the linear portion of the progressive curve and is converted to the unit of μg PLQ molecules per min.

Figure 10:
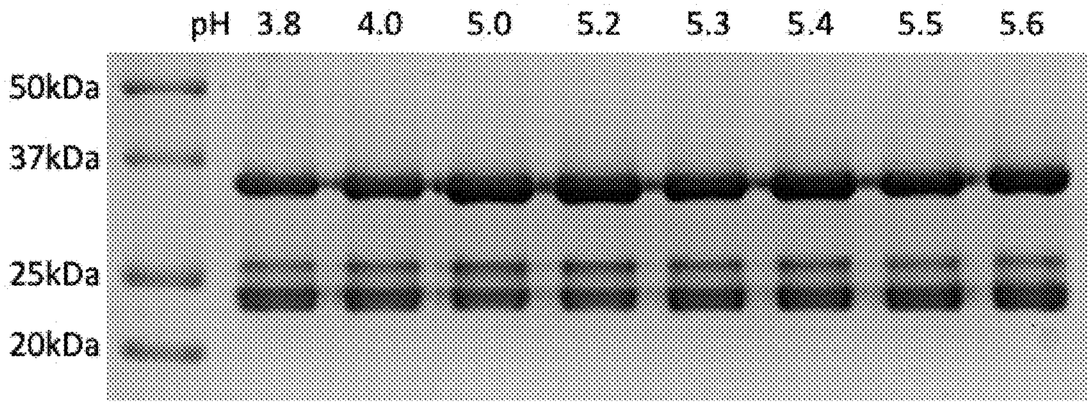

FIG. 10—SDS-PAGE of pro-ananain activation in sodium acetate buffer at varied pH values.

SDS-PAGE was applied to visualize active ananain resulting from the activation process at different pH values in sodium acetate buffer. Pro-ananain and active ananain are displayed as a 36 kDa and a 24 kDa band, respectively, in a 12.5% SDS-gel. Lane 1, molecule weight markers. Lanes 2-9, incubation at various pH values.

Figure 11:
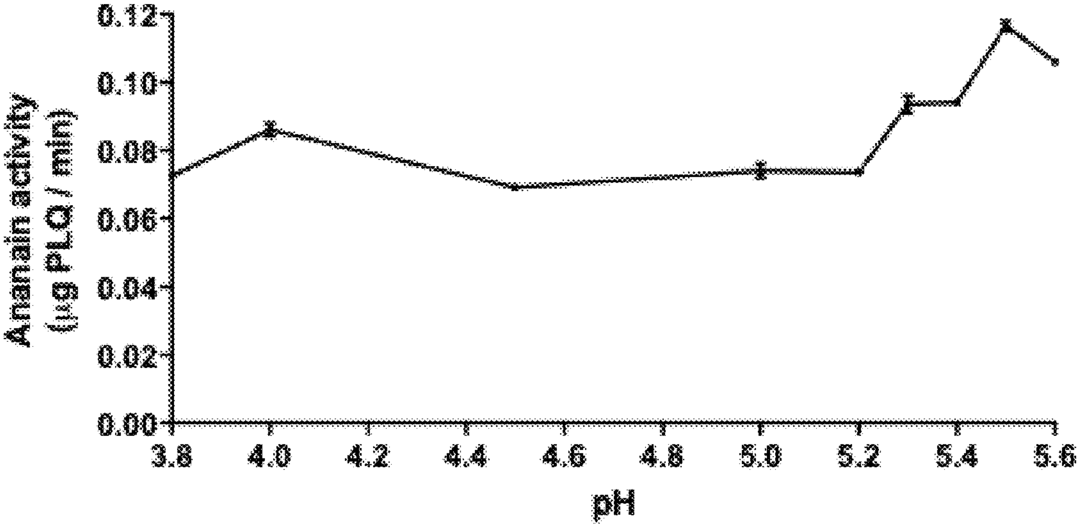

FIG. 11—Activity assay of pro-ananain activation in sodium acetate buffer at varied pH values.

Graphic representation of the activity of mature ananain resulting from the activation process at different pH values in sodium acetate buffer. PLQ is the fluorescent tripeptidyl substrate: MeOC-GGG-PLQ-GG-DPA-KK-$NH_2$ (SEQ ID NO: 7). Cleavage at the core PLQ tripeptide tethered between the fluorescent MeOC donor group and the DPA quencher moiety releases the fluorescence of the MeOC donor group, which is detected by using a POLARstar fluorescent plate reader (BMG Labtech, Offenburg, Germany) with excitation and emission wavelengths of 320 nm and 420 nm, respectively. The initial rate of proteolysis of substrate is measured as the slope of the linear portion of the progressive curve and is converted to the unit of μg PLQ molecules per min.

Figure 12:
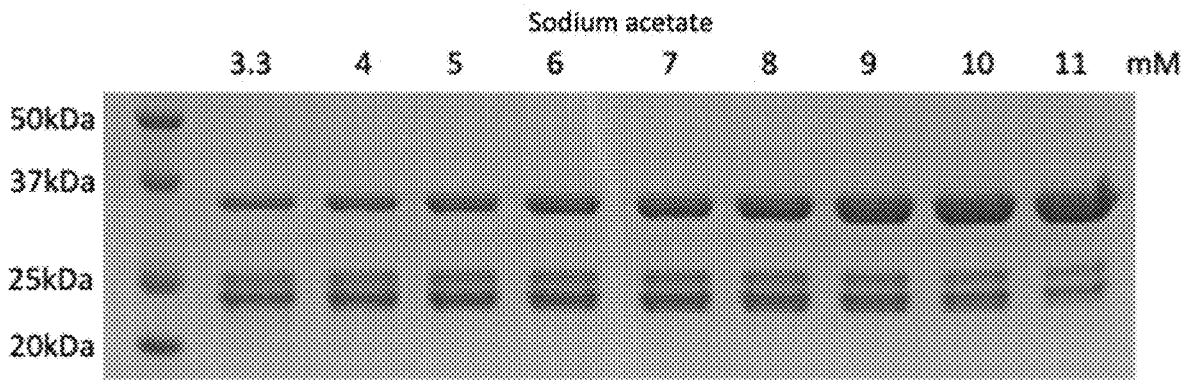

FIG. 12—SDS-PAGE of pro-ananain activation in varied concentrations of sodium acetate buffer.

SDS-PAGE was applied to visualize active ananain resulting from the activation process in different concentrations of sodium acetate buffer. Pro-ananain and active ananain are displayed as a 36 kDa and a 24 kDa band, respectively, in a 12.5% SDS-gel. Lane 1, molecule weight markers. Lanes 2-10, incubation in various concentrations of sodium acetate buffer.

Figure 13:
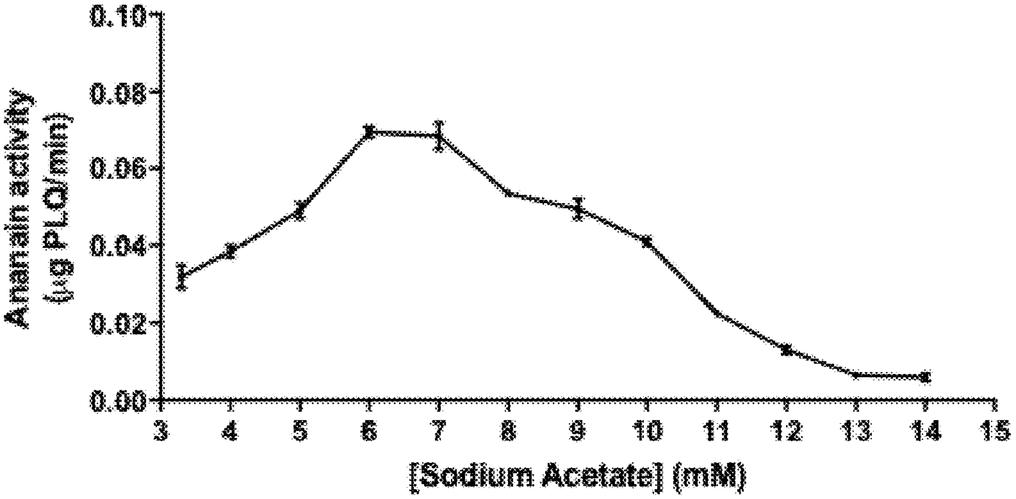

FIG. 13—Activity assay of pro-ananain activation in varied concentrations of sodium acetate buffer.

Graphic representation of the activity of mature ananain resulting from the activation process in different concentrations of sodium acetate buffer. PLQ is the fluorescent tripeptidyl substrate: MeOC-GGG-PLQ-GG-DPA-KK-$NH_2$ (SEQ ID NO: 7). Cleavage at the core PLQ tripeptide tethered between the fluorescent MeOC donor group and the DPA quencher moiety releases the fluorescence of the MeOC donor group, which is detected by using a POLARstar fluorescent plate reader (BMG Labtech, Offenburg, Germany) with excitation and emission wavelengths of 320 nm and 420 nm, respectively. The initial rate of proteolysis of substrate is measured as the slope of the linear portion of the progressive curve and is converted to the unit of μg PLQ molecules per min.

Figure 14:
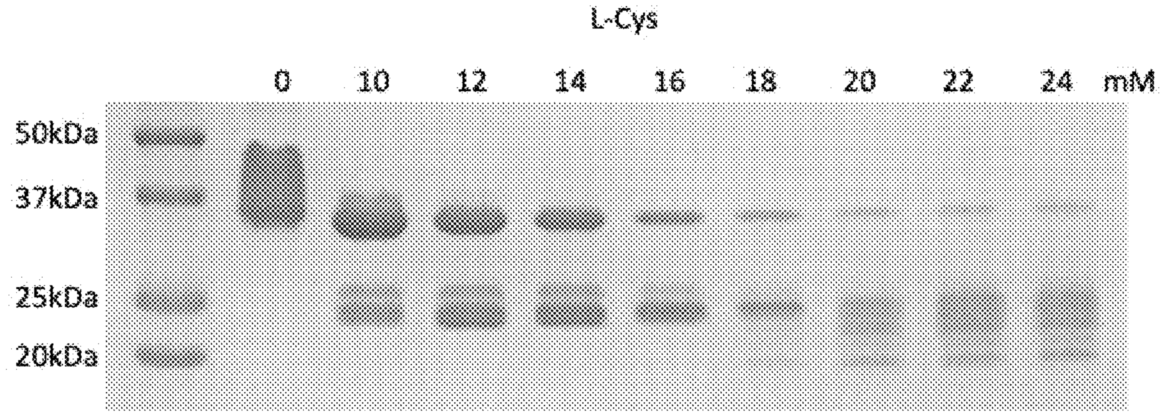

FIG. 14—SDS-PAGE of pro-ananain activation in varied concentrations of L-Cys in sodium acetate buffer.

SDS-PAGE was applied to visualize active ananain resulting from the activation process in different concentrations of L-Cys in sodium acetate buffer. Pro-ananain and active ananain are displayed as a 36 kDa and a 24 kDa band, respectively, in a 12.5% SDS-gel. Lane 1, molecule weight markers. Lanes 2-10, incubation in various concentrations of L-Cys.

Figure 15:
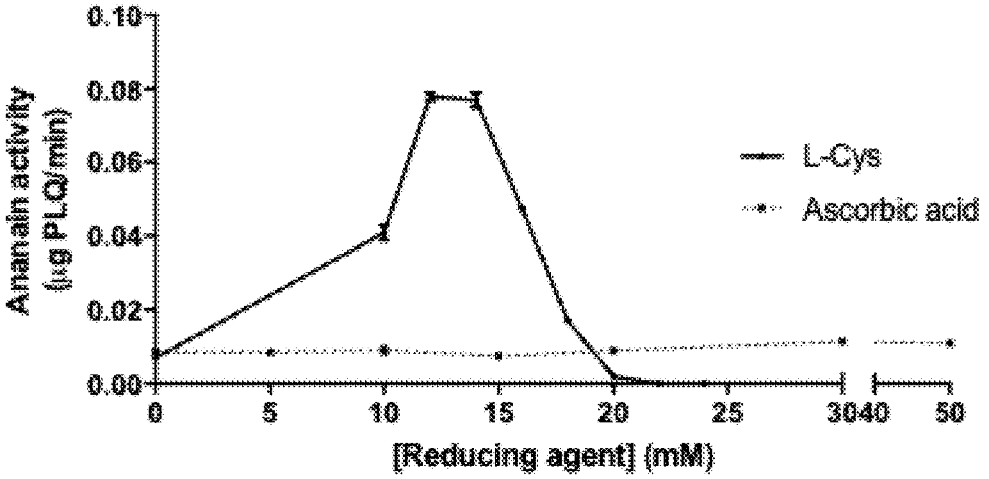

FIG. 15—Activity assay of pro-ananain activation in varied concentrations of reducing agent in sodium acetate buffer.

Graphic representation of the activity of mature ananain resulting from the activation process at varied concentrations of reducing agent: L-Cys or ascorbic acid in sodium acetate buffer. PLQ is the fluorescent tripeptidyl substrate: MeOC-GGG-PLQ-GG-DPA-KK-$NH_2$ (SEQ ID NO: 7). Cleavage at the core PLQ tripeptide tethered between the fluorescent MeOC donor group and the DPA quencher moiety releases the fluorescence of the MeOC donor group, which is detected by using a POLARstar fluorescent plate reader (BMG Labtech, Offenburg, Germany) with excitation and emission wavelengths of 320 nm and 420 nm, respectively. The initial rate of proteolysis of substrate is measured as the slope of the linear portion of the progressive curve and is converted to the unit of g PLQ molecules per min.

Figure 16:
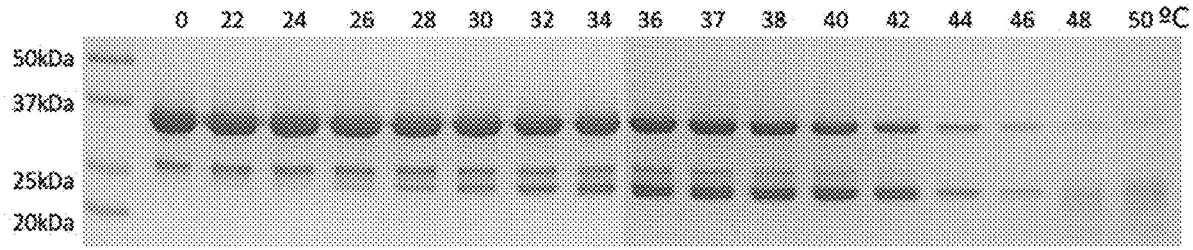

FIG. 16—SDS-PAGE of pro-ananain activation at varied temperatures in sodium acetate buffer.

SDS-PAGE was applied to visualize active ananain resulting from the activation process at different temperatures between 0 and 50° C. in sodium acetate buffer. Pro-ananain and active ananain are displayed as a 36 kDa and a 24 kDa band, respectively, in a 12.5% SDS-gel. Lane 1, molecule weight markers. Lanes 2-18, incubation at various temperatures.

Figure 17:
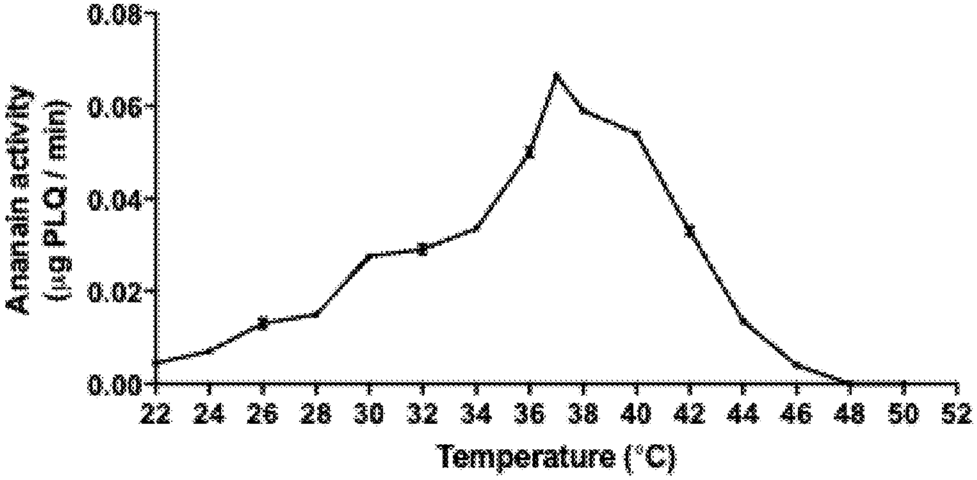

FIG. 17—Activity assay of pro-ananain activation at varied temperatures in sodium acetate buffer.

Graphic representation of the activity of mature ananain resulting from the activation process at different temperatures between 22 and 50° C. in sodium acetate buffer. PLQ is the fluorescent tripeptidyl substrate: MeOC-GGG-PLQ-GG-DPA-KK-$NH_2$ (SEQ ID NO: 7). Cleavage at the core PLQ tripeptide tethered between the fluorescent MeOC donor group and the DPA quencher moiety releases the fluorescence of the MeOC donor group, which is detected by using a POLARstar fluorescent plate reader (BMG Labtech, Offenburg, Germany) with excitation and emission wavelengths of 320 nm and 420 nm, respectively. The initial rate of proteolysis of substrate is measured as the slope of the linear portion of the progressive curve and is converted to the unit of μg PLQ molecules per min.

Figure 18:
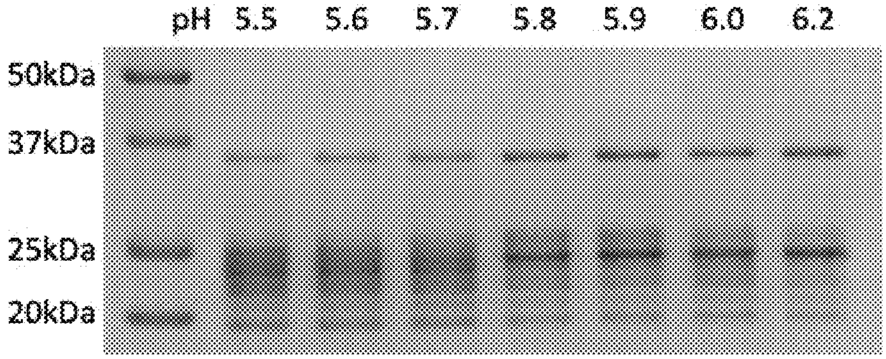

FIG. 18—SDS-PAGE of pro-ananain activation in 2-(N-morpholino)ethanesulfonic acid (MES) buffer at varied pH values.

SDS-PAGE was applied to visualize active ananain resulting from the activation process at different pH values in MES buffer. Pro-ananain and active ananain are displayed as a 36 kDa and a 24 kDa band, respectively, in a 12.5% SDS-gel. Lane 1, molecule weight markers. Lanes 2-8, incubation at various pH values.

Figure 19:
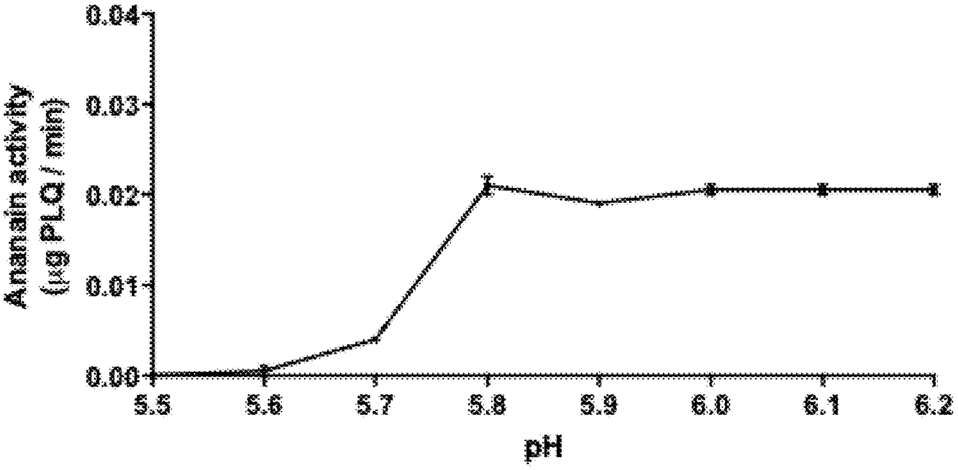

FIG. 19—Activity assay of pro-ananain activation in MES buffer at varied pH values.

Graphic representation of the activity of mature ananain resulting from the activation process at different pH values in MES buffer. PLQ is the fluorescent tripeptidyl substrate: MeOC-GGG-PLQ-GG-DPA-KK-$NH_2$ (SEQ ID NO: 7). Cleavage at the core PLQ tripeptide tethered between the fluorescent MeOC donor group and the DPA quencher moiety releases the fluorescence of the MeOC donor group, which is detected by using a POLARstar fluorescent plate reader (BMG Labtech, Offenburg, Germany) with excitation and emission wavelengths of 320 nm and 420 nm, respectively. The initial rate of proteolysis of substrate is measured as the slope of the linear portion of the progressive curve and is converted to the unit of μg PLQ molecules per min.

Figure 20:
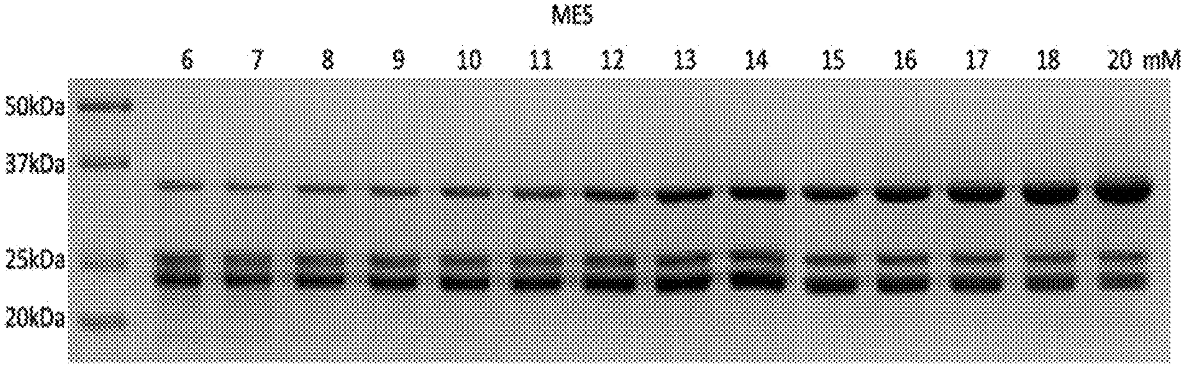

FIG. 20—The SDS-PAGE of pro-ananain activation in varied concentrations of MES buffer.

SDS-PAGE was applied to visualize active ananain resulting from the activation process in different concentrations of MES buffer. Pro-ananain and active ananain are displayed as a 36 kDa and a 24 kDa band, respectively, in a 12.5% SDS-gel. Lane 1, molecule weight markers. Lanes 2-15, incubation in various concentrations of MES buffer.

Figure 21:
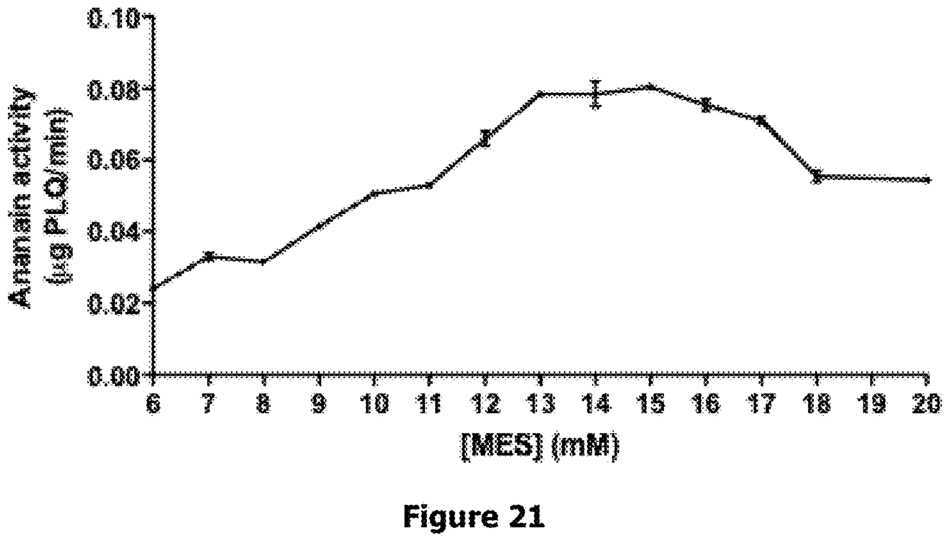

FIG. 21—Activity assay of pro-ananain activation in varied concentrations of MES.

Graphic representation of the activity of mature ananain resulting from the activation process in different concentrations of MES buffer. PLQ is the fluorescent tripeptidyl substrate: MeOC-GGG-PLQ-GG-DPA-KK-$NH_2$ (SEQ ID NO: 7). Cleavage at the core PLQ tripeptide tethered between the fluorescent MeOC donor group and the DPA quencher moiety releases the fluorescence of the MeOC donor group, which is detected by using a POLARstar fluorescent plate reader (BMG Labtech, Offenburg, Germany) with excitation and emission wavelengths of 320 nm and 420 nm, respectively. The initial rate of proteolysis of substrate is measured as the slope of the linear portion of the progressive curve and is converted to the unit of μg PLQ molecules per min.

Figure 22:
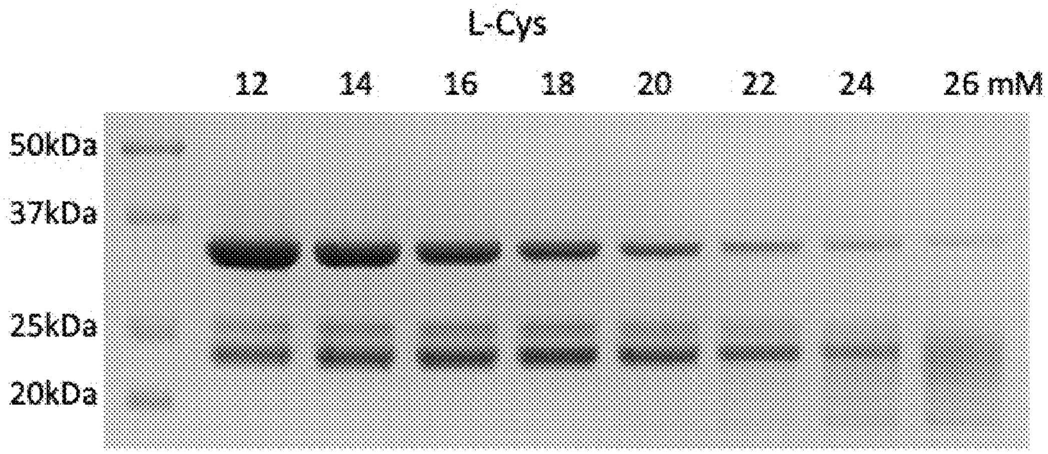

FIG. 22—SDS-PAGE of pro-ananain activation in varied concentrations of L-Cys in MES buffer.

SDS-PAGE was applied to visualize active ananain resulting from the activation process in different concentrations of L-Cys in MES buffer. Pro-ananain and active ananain are displayed as a 36 kDa and a 24 kDa band, respectively, in a 12.5% SDS-gel. Lane 1, molecule weight markers. Lanes 2-9, incubation at various concentrations of L-Cys in MES buffer.

Figure 23:
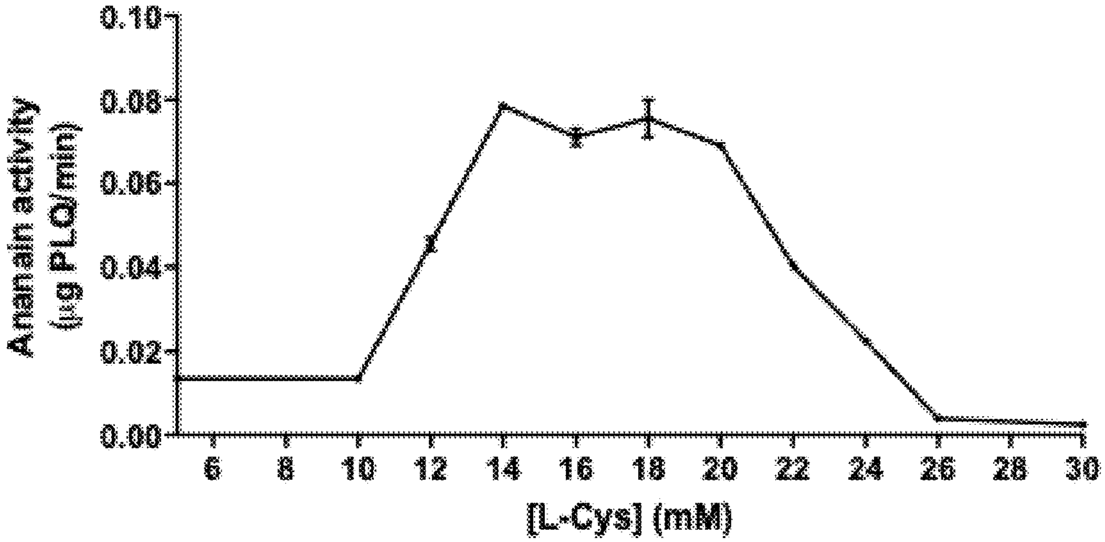

FIG. 23—Activity assay of pro-ananain activation in varied concentrations of L-Cys in an MES buffer.

Graphic representation of the activity of mature ananain resulting from the activation process in different concentrations of L-Cys in MES buffer. PLQ is the fluorescent tripeptidyl substrate: MeOC-GGG-PLQ-GG-DPA-KK-$NH_2$ (SEQ ID NO: 7). Cleavage at the core PLQ tripeptide tethered between the fluorescent MeOC donor group and the DPA quencher moiety releases the fluorescence of the MeOC donor group, which is detected by using a POLARstar fluorescent plate reader (BMG Labtech, Offenburg, Germany) with excitation and emission wavelengths of 320 nm and 420 nm, respectively. The initial rate of proteolysis of substrate is measured as the slope of the linear portion of the progressive curve and is converted to the unit of μg PLQ molecules per min.

Figure 24:
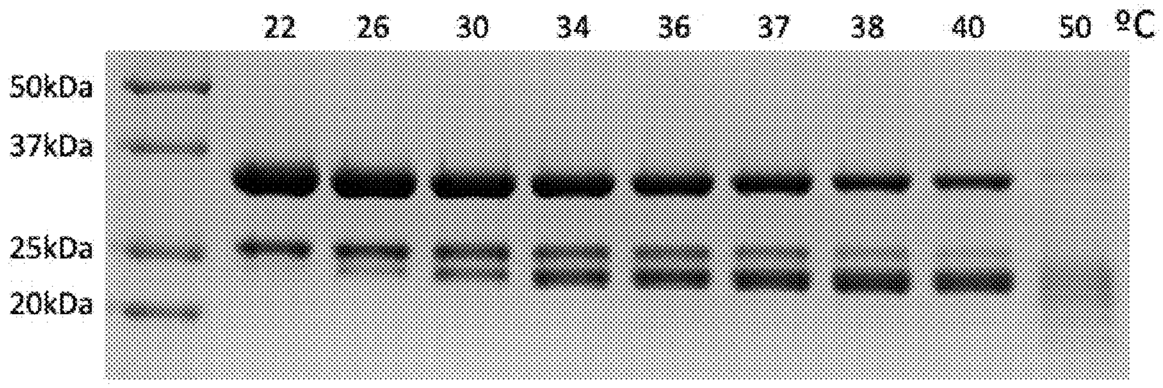

FIG. 24—SDS-PAGE of pro-ananain activation at varied temperatures in MES buffer.

SDS-PAGE was applied to visualize active ananain resulting from the activation process at different temperatures between 22 and 50° C. in MES buffer. Pro-ananain and active ananain are displayed as a 36 kDa and a 24 kDa band, respectively, in a 12.5% SDS-gel. Lane 1, molecule weight markers. Lanes 2-18, incubation at various temperatures.

Figure 25:
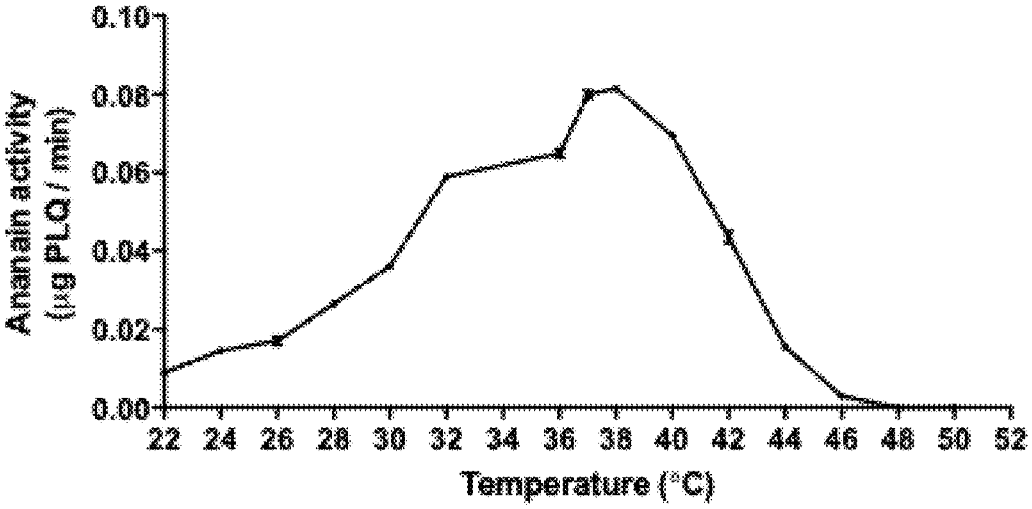

FIG. 25—Activity assay of pro-ananain activation at varied temperatures in MES buffer.

Graphic representation of the activity of mature ananain resulting from the activation process at different temperatures between 0 and 50° C. in MES buffer. PLQ is the fluorescent tripeptidyl substrate: MeOC-GGG-PLQ-GG-DPA-KK-$NH_2$ (SEQ ID NO: 7). Cleavage at the core PLQ tripeptide tethered between the fluorescent MeOC donor group and the DPA quencher moiety releases the fluorescence of the MeOC donor group, which is detected by using a POLARstar fluorescent plate reader (BMG Labtech, Offenburg, Germany) with excitation and emission wavelengths of 320 nm and 420 nm, respectively. The initial rate of proteolysis of substrate is measured as the slope of the linear portion of the progressive curve and is converted to the unit of μg PLQ molecules per min.

Figure 26:
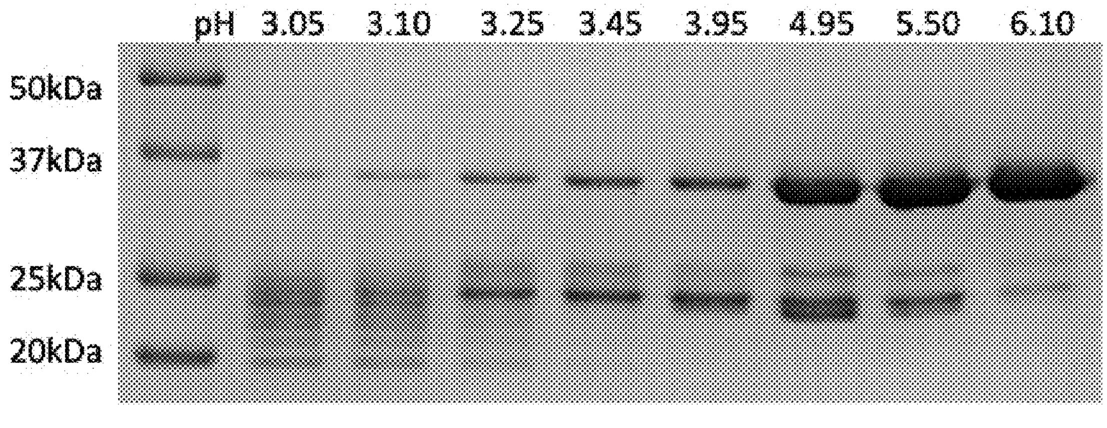

FIG. 26—SDS-PAGE of pro-ananain activation in sodium citrate buffer at varied pH values.

SDS-PAGE was applied to visualize active ananain resulting from the activation process at different pH values in sodium citrate buffer. Pro-ananain and active ananain are displayed as a 36 kDa and a 24 kDa band, respectively, in a 12.5% SDS-gel. Lane 1, molecule weight markers. Lanes 2-9, incubation at various pH values.

Figure 27:
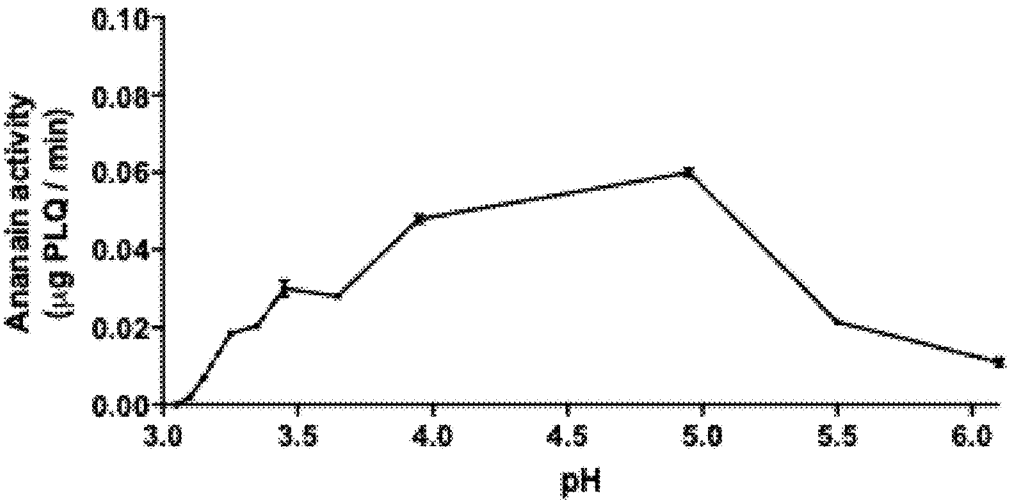

FIG. 27—Activity assay of pro-ananain activation in sodium citrate buffer at varied pH values.

Graphic representation of the activity of mature ananain resulting from the activation process at different pH values in sodium citrate buffer. PLQ is the fluorescent tripeptidyl substrate: MeOC-GGG-PLQ-GG-DPA-KK-$NH_2$ (SEQ ID NO: 7). Cleavage at the core PLQ tripeptide tethered between the fluorescent MeOC donor group and the DPA quencher moiety releases the fluorescence of the MeOC donor group, which is detected by using a POLARstar fluorescent plate reader (BMG Labtech, Offenburg, Germany) with excitation and emission wavelengths of 320 nm and 420 nm, respectively. The initial rate of proteolysis of substrate is measured as the slope of the linear portion of the progressive curve and is converted to the unit of μg PLQ molecules per min.

Figure 28:
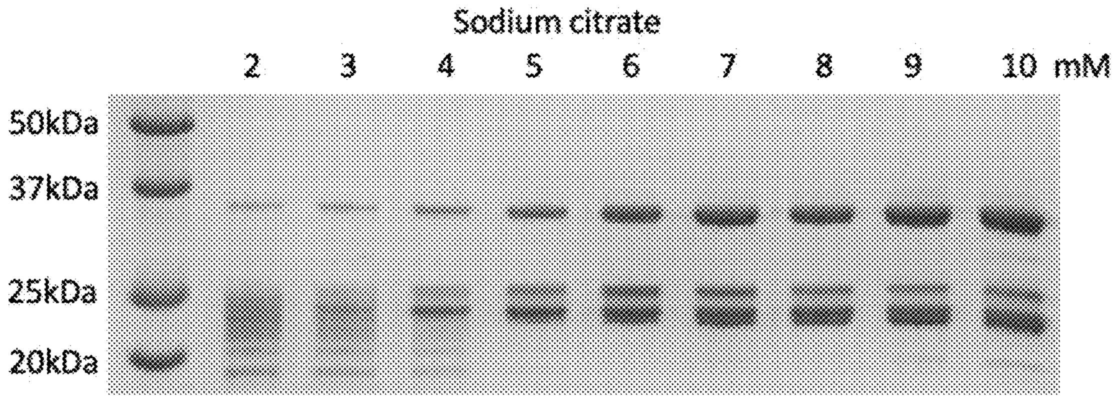

FIG. 28—SDS-PAGE of pro-ananain activation in varied concentrations of sodium citrate buffer.

SDS-PAGE was applied to visualize active ananain resulting from the activation process at different pH values in phosphate-citrate buffer. Pro-ananain and active ananain are displayed as a 36 kDa and a 24 kDa band, respectively, in a 12.5% SDS-gel. Lane 1, molecule weight markers. Lanes 2-10, incubation in various concentrations of sodium citrate buffer.

Figure 29:
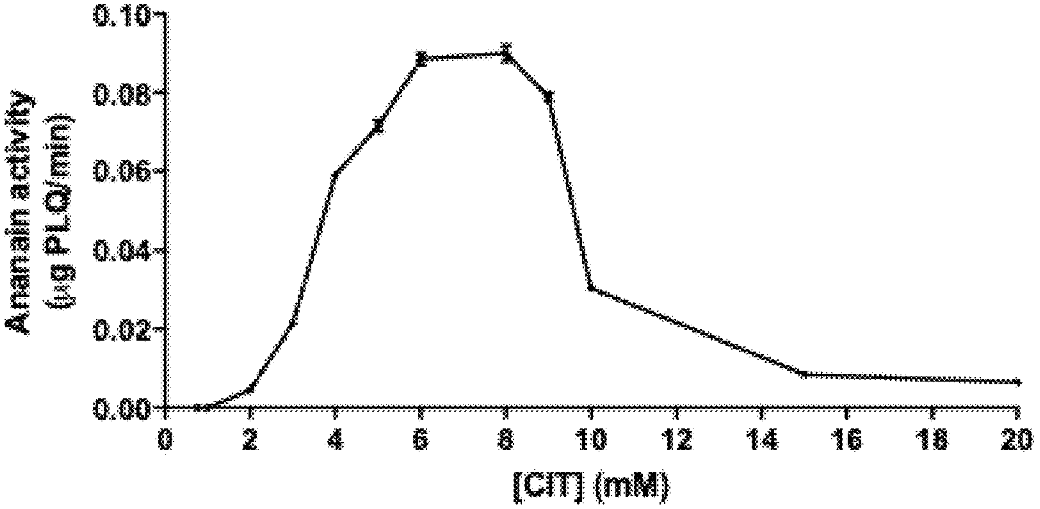

FIG. 29—Activity assay of pro-ananain activation in varied concentrations of sodium citrate buffer.

Graphic representation of the activity of mature ananain resulting from the activation process in different concentrations of sodium citrate buffer. PLQ is the fluorescent tripeptidyl substrate: MeOC-GGG-PLQ-GG-DPA-KK-$NH_2$ (SEQ ID NO: 7). Cleavage at the core PLQ tripeptide tethered between the fluorescent MeOC donor group and the DPA quencher moiety releases the fluorescence of the MeOC donor group, which is detected by using a POLARstar fluorescent plate reader (BMG Labtech, Offenburg, Germany) with excitation and emission wavelengths of 320 nm and 420 nm, respectively. The initial rate of proteolysis of substrate is measured as the slope of the linear portion of the progressive curve and is converted to the unit of μg PLQ molecules per min.

Figure 30:
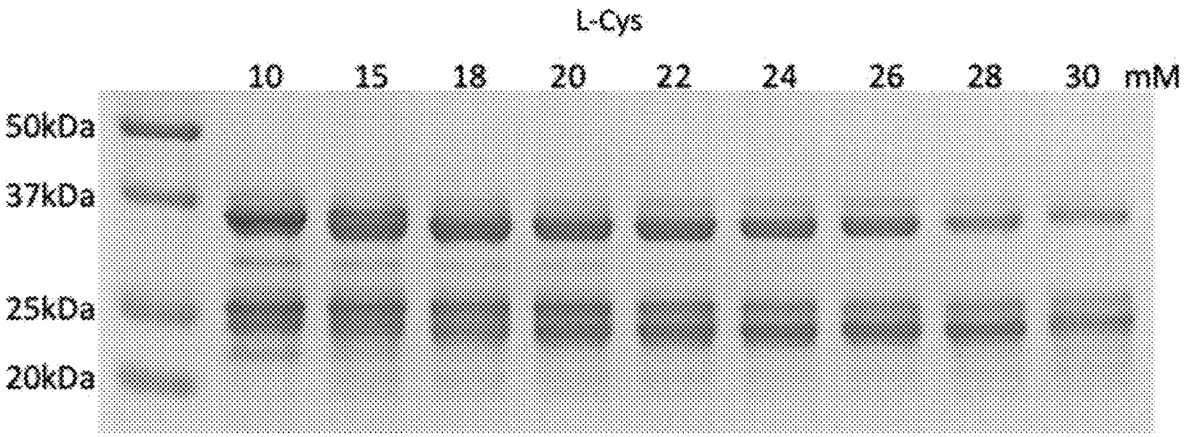

FIG. 30—SDS-PAGE of pro-ananain activation in varied concentrations of L-Cys in sodium citrate buffer.

SDS-PAGE was applied to visualize active ananain resulting from the activation process in different concentrations of L-Cys in sodium citrate buffer. Pro-ananain and active ananain are displayed as a 36 kDa and a 24 kDa band, respectively, in a 12.5% SDS-gel. Lane 1, molecule weight markers. Lanes 2-10, incubation in various concentrations of L-Cys.

Figure 31:
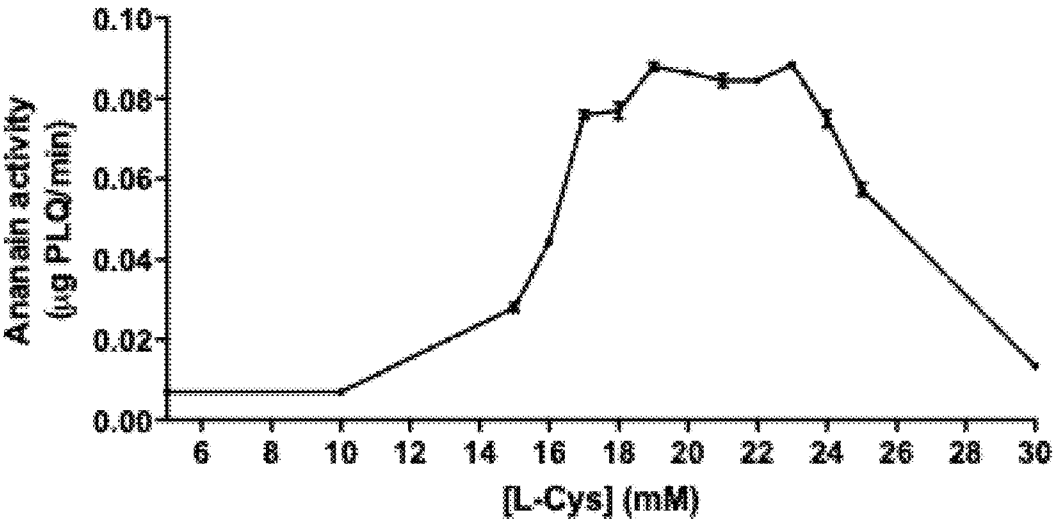

FIG. 31—Activity assay of pro-ananain activation in varied concentrations of L-Cys in sodium citrate buffer.

Graphic representation of the activity of mature ananain resulting from the activation process in different concentrations of L-Cys in sodium citrate buffer. PLQ is the fluorescent tripeptidyl substrate: MeOC-GGG-PLQ-GG-DPA-KK-$NH_2$ (SEQ ID NO: 7). Cleavage at the core PLQ tripeptide tethered between the fluorescent MeOC donor group and the DPA quencher moiety releases the fluorescence of the MeOC donor group, which is detected by using a POLARstar fluorescent plate reader (BMG Labtech, Offenburg, Germany) with excitation and emission wavelengths of 320 nm and 420 nm, respectively. The initial rate of proteolysis of substrate is measured as the slope of the linear portion of the progressive curve and is converted to the unit of μg PLQ molecules per min.

Figure 32:
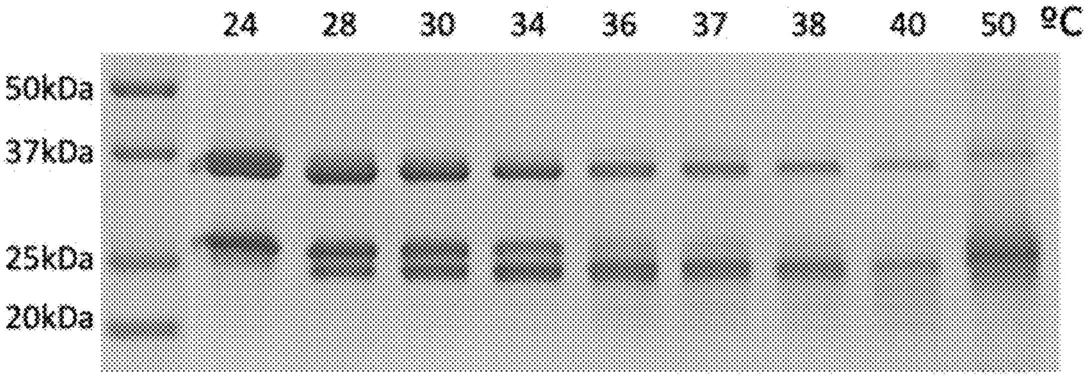

FIG. 32—SDS-PAGE of pro-ananain activation at varied temperatures in sodium citrate buffer.

SDS-PAGE was applied to visualize active ananain resulting from the activation process at different temperatures between 24 and 50° C. in sodium citrate buffer. Pro-ananain and active ananain are displayed as a 36 kDa and a 24 kDa band, respectively, in a 12.5% SDS-gel. Lane 1, molecule weight markers. Lanes 2-10, incubation at different temperatures.

Figure 33:
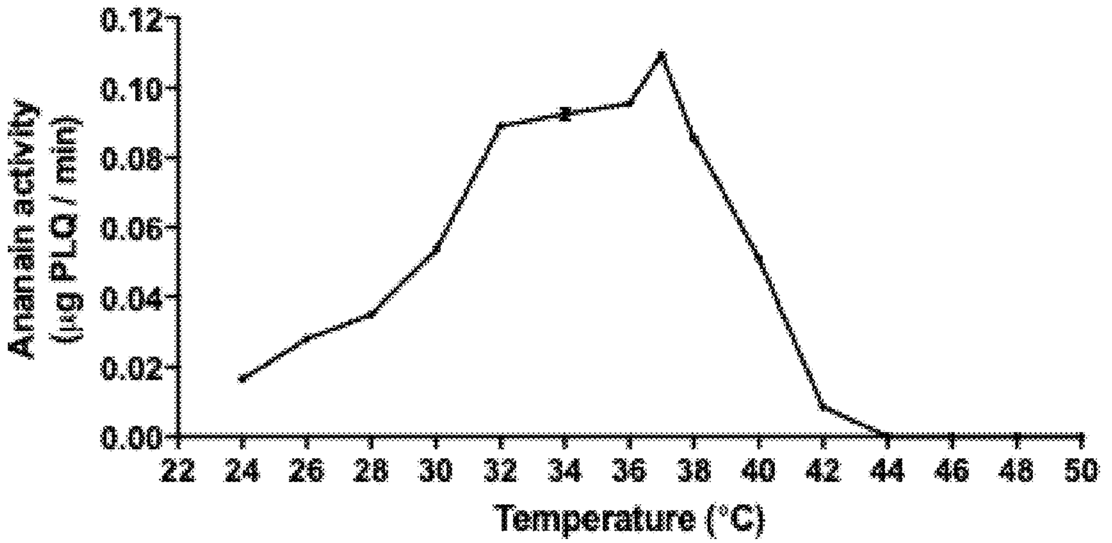

FIG. 33—Activity assay of pro-ananain activation at varied temperatures in sodium citrate buffer.

Graphic representation of the activity of mature ananain resulting from the activation process at different temperatures between 24 and 50° C. in sodium citrate buffer. PLQ is the fluorescent tripeptidyl substrate: MeOC-GGG-PLQ-GG-DPA-KK-$NH_2$ (SEQ ID NO: 7). Cleavage at the core PLQ tripeptide tethered between the fluorescent MeOC donor group and the DPA quencher moiety releases the fluorescence of the MeOC donor group, which is detected by using a POLARstar fluorescent plate reader (BMG Labtech, Offenburg, Germany) with excitation and emission wavelengths of 320 nm and 420 nm, respectively. The initial rate of proteolysis of substrate is measured as the slope of the linear portion of the progressive curve and is converted to the unit of μg PLQ molecules per min.

Figure 34:
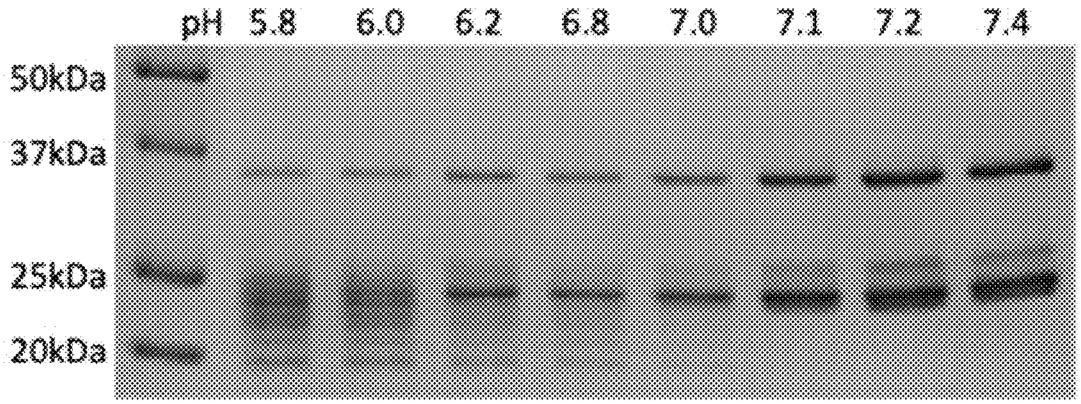

FIG. 34—SDS-PAGE of pro-ananain activation in phosphate buffered saline (PBS) buffer at varied pH values.

SDS-PAGE was applied to visualize active ananain resulting from the activation process at different pH values in PBS buffer. Pro-ananain and active ananain are displayed as a 36 kDa and a 24 kDa band, respectively, in a 12.5% SDS-gel. Lane 1, molecule weight markers. Lanes 2-9, incubation at various pH values.

Figure 35:
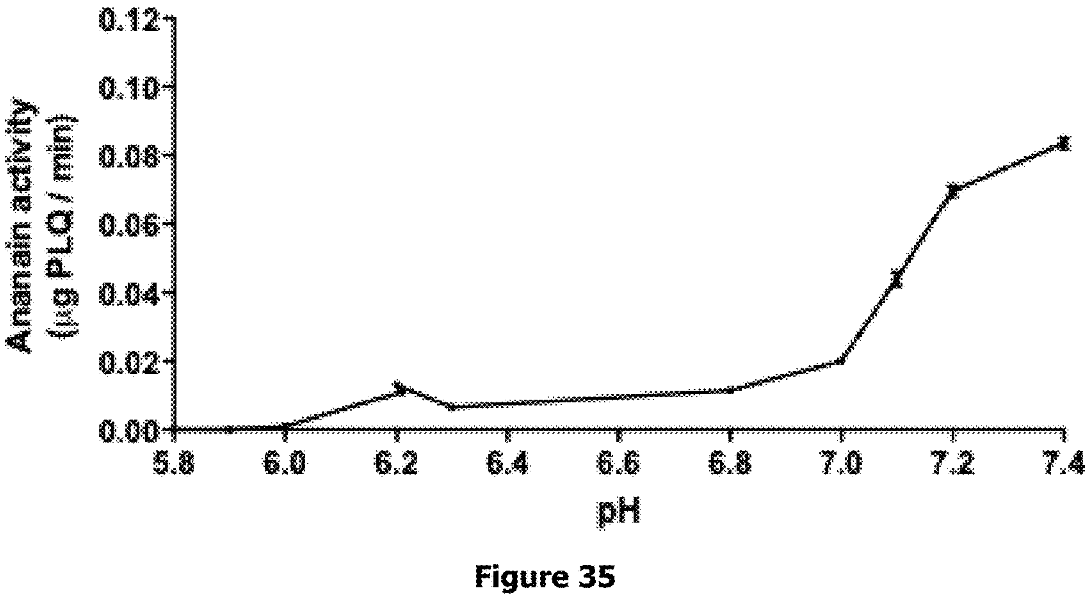

FIG. 35—Activity assay of pro-ananain activation in PBS buffer at varied pH values.

Graphic representation of the activity of mature ananain resulting from the activation process at different pH values in PBS buffer. PLQ is the fluorescent tripeptidyl substrate: MeOC-GGG-PLQ-GG-DPA-KK-$NH_2$ (SEQ ID NO: 7). Cleavage at the core PLQ tripeptide tethered between the fluorescent MeOC donor group and the DPA quencher moiety releases the fluorescence of the MeOC donor group, which is detected by using a POLARstar fluorescent plate reader (BMG Labtech, Offenburg, Germany) with excitation and emission wavelengths of 320 nm and 420 nm, respectively. The initial rate of proteolysis of substrate is measured as the slope of the linear portion of the progressive curve and is converted to the unit of μg PLQ molecules per min.

Figure 36:
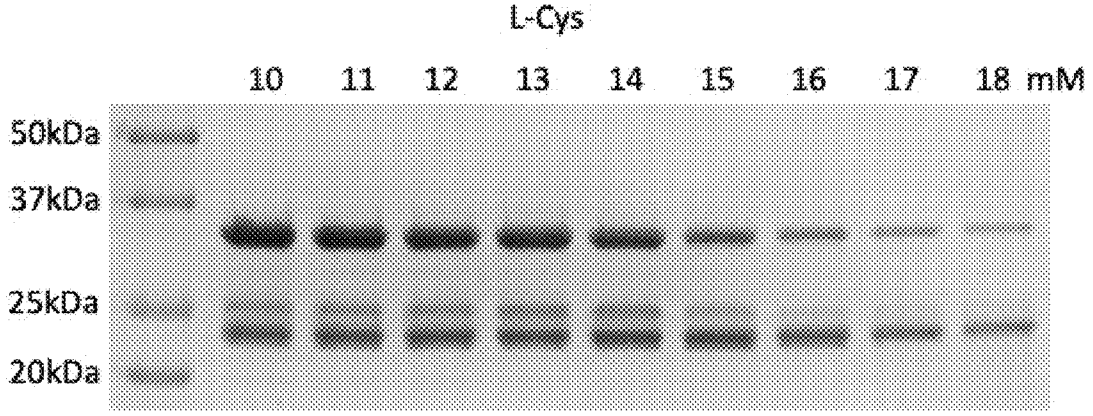

FIG. 36—SDS-PAGE of pro-ananain activation in varied concentrations of L-Cys in PBS buffer.

SDS-PAGE was applied to visualize active ananain resulting from the activation process in different concentrations of L-Cys in PBS buffer. Pro-ananain and active ananain are displayed as a 36 kDa and a 24 kDa band, respectively, in a 12.5% SDS-gel. Lane 1, molecule weight markers. Lanes 2-10, incubation in various concentrations of L-Cys.

Figure 37:
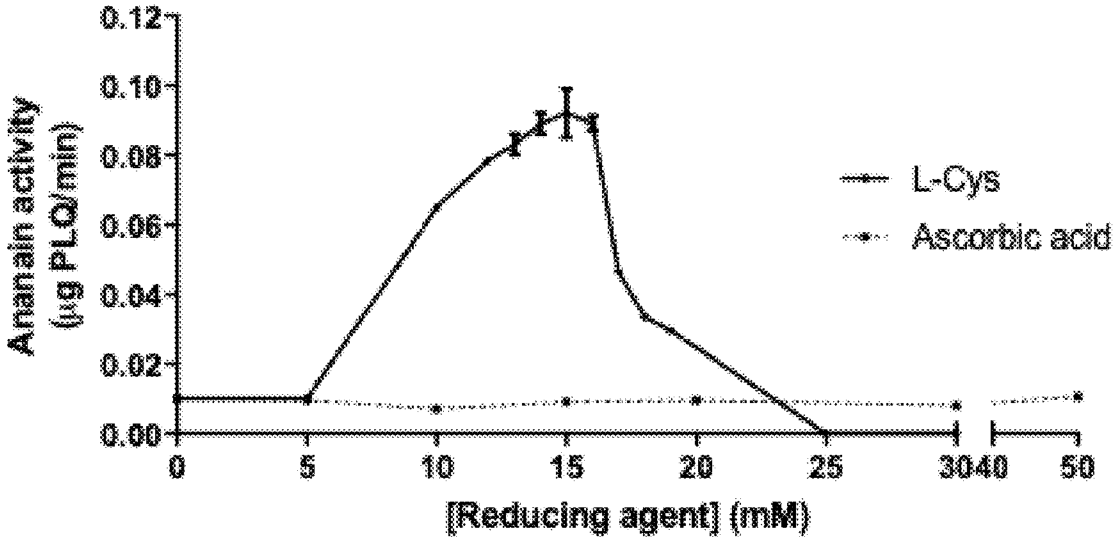

FIG. 37—Activity assay of pro-ananain activation in varied concentration of L-Cys or ascorbic acid in PBS buffer.

Graphic representation of the activity of mature ananain resulting from the activation process at varied concentrations of reducing agent: L-Cys or ascorbic acid in PBS buffer. PLQ is the fluorescent tripeptidyl substrate: MeOC-GGG-PLQ-GG-DPA-KK-$NH_2$ (SEQ ID NO: 7). Cleavage at the core PLQ tripeptide tethered between the fluorescent MeOC donor group and the DPA quencher moiety releases the fluorescence of the MeOC donor group, which is detected by using a POLARstar fluorescent plate reader (BMG Labtech, Offenburg, Germany) with excitation and emission wavelengths of 320 nm and 420 nm, respectively. The initial rate of proteolysis of substrate is measured as the slope of the linear portion of the progressive curve and is converted to the unit of μg PLQ molecules per min.

Figure 38:
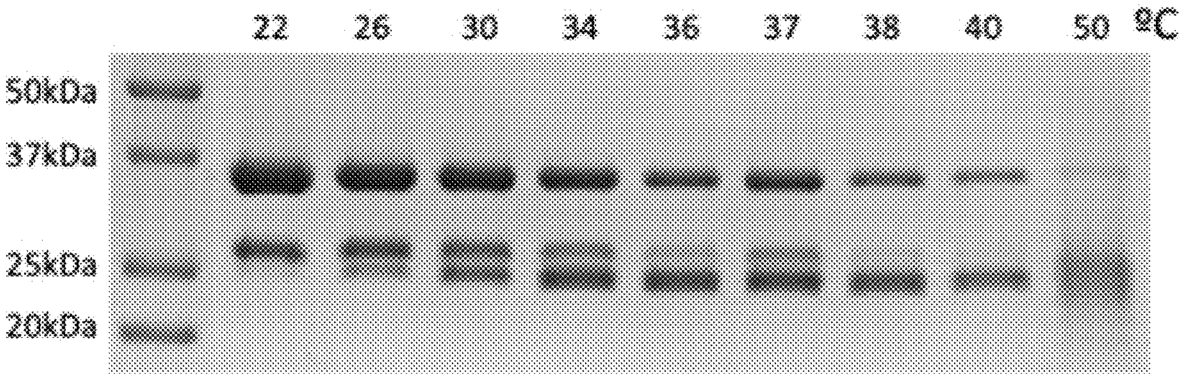

FIG. 38—SDS-PAGE of pro-ananain activation at varied temperatures in PBS buffer.

SDS-PAGE was applied to visualize active ananain resulting from the activation process at different temperatures between 22 and 50° C. in PBS buffer. Pro-ananain and active ananain are displayed as a 36 kDa and a 24 kDa band, respectively, in a 12.5% SDS-gel. Lane 1, molecule weight markers. Lanes 2-18, incubation at various temperatures.

Figure 39:
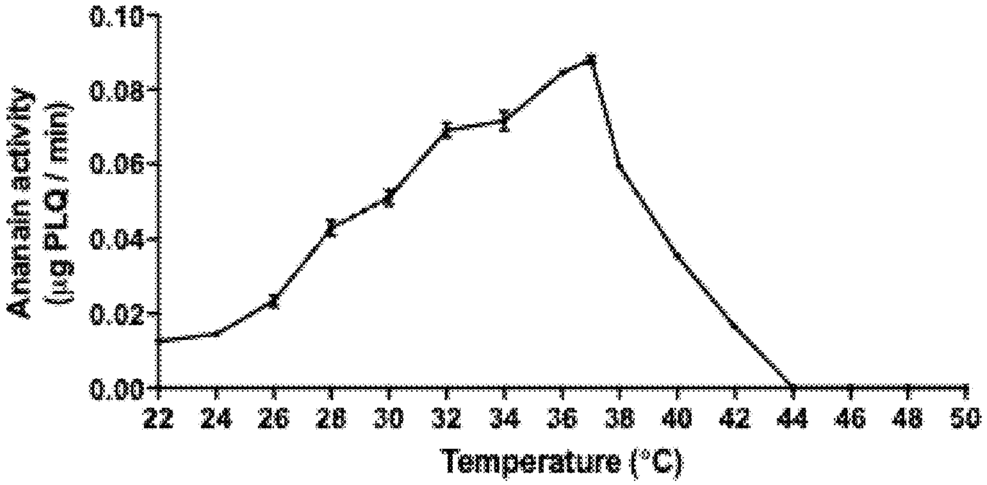

FIG. 39—Activity assay of pro-ananain activation at varied temperatures in PBS buffer.

Graphic representation of the activity of mature ananain resulting from the activation process at different temperatures between 22 and 50° C. in PBS buffer. PLQ is the fluorescent tripeptidyl substrate: MeOC-GGG-PLQ-GG-DPA-KK-$NH_2$ (SEQ ID NO: 7). Cleavage at the core PLQ tripeptide tethered between the fluorescent MeOC donor group and the DPA quencher moiety releases the fluorescence of the MeOC donor group, which is detected by using a POLARstar fluorescent plate reader (BMG Labtech, Offenburg, Germany) with excitation and emission wavelengths of 320 nm and 420 nm, respectively. The initial rate of proteolysis of substrate is measured as the slope of the linear portion of the progressive curve and is converted to the unit of μg PLQ molecules per min.

Figure 40:
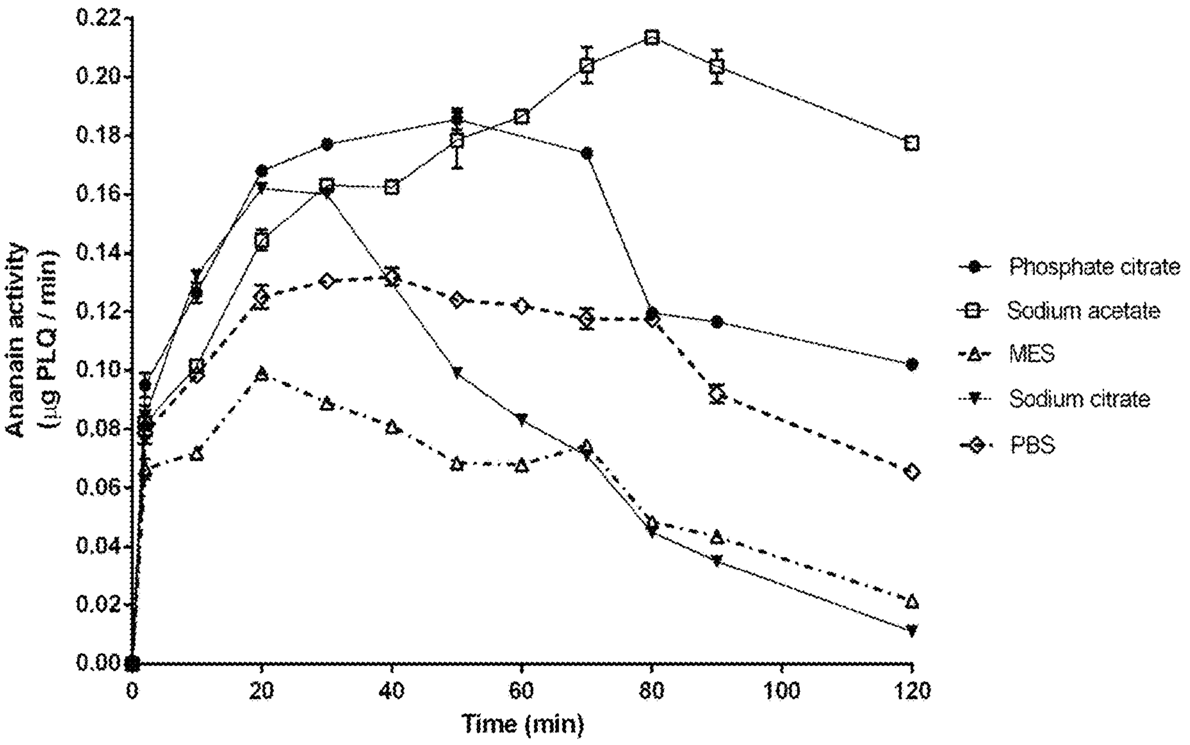

FIG. 40—Activity assay of water reconstituted pro-ananain formulations.

Five lyophilized pro-ananain formulations were resuspended with 0.5 ml water pre-warmed at 37° C. The solutions were incubated at 37° C. for 120 min for a time course examination of active ananain. PLQ is the fluorescent tripeptidyl substrate: MeOC-GGG-PLQ-GG-DPA-KK-$NH_2$ (SEQ ID NO: 7). Cleavage at the core PLQ tripeptide tethered between the fluorescent MeOC donor group and the DPA quencher moiety releases the fluorescence of the MeOC donor group, which is detected by using a POLARstar fluorescent plate reader (BMG Labtech, Offenburg, Germany) with excitation and emission wavelengths of 320 nm and 420 nm, respectively. The initial rate of proteolysis of substrate is measured as the slope of the linear portion of the progressive curve and is converted to the unit of g PLQ molecules per min.

Figure 41:
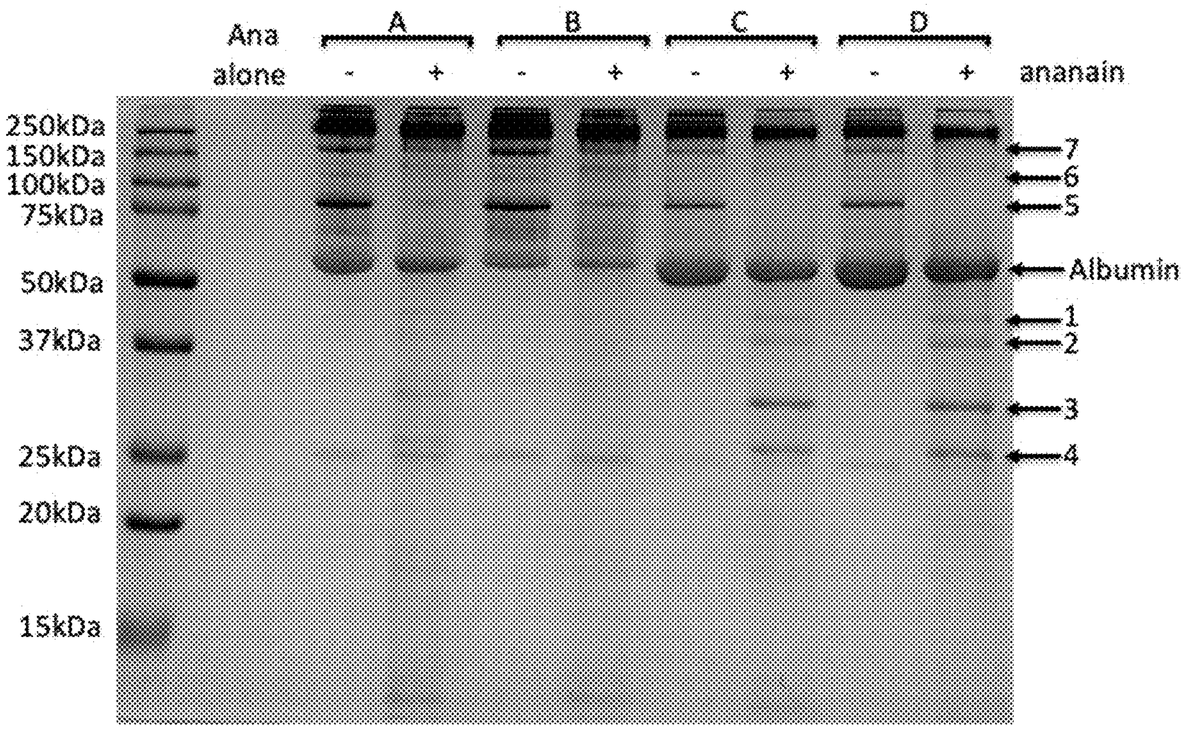

FIG. 41—The proteolytic activity of ananain against human plasma proteins.

SDS-PAGE was applied to visualize the proteolytic activity of ananain with human plasma proteins. Lane 1, molecule weight markers; Lane 2—ana alone—ananain only. A(−): Albumin-partially depleted human plasma, A(+): Albumin-partially depleted human plasma+ananain; B(−): Albumin-fully depleted human plasma, B(+) Albumin-fully depleted human plasma+ananain; C(−): Human plasma, C(+): Human plasma+ananain; D(−): Human serum, D(+) Human serum+ananain. The reaction was prepared in PBS (pH7.4), incubated at 37° C. for 15 min. Active ananain from the phosphate citrate pro-ananain formulation maintained its proteolytic activity against human plasma proteins at a >1:100 ratio within 15 min. The clear reduction of albumin in sample A, C and D in present of ananain indicates that albumin is a protein substrate for ananain. The cleavage results in fragments of varied molecular weights, including 1, 2, 3 and 4 as marked with arrows, which are not presented in sample B, confirming that the source of these fragments is albumin. Besides albumin, high molecular weight human proteins or complexes, marked as bands 5, 6 and 7 are also highly likely protein substrates for ananain.

FIG. 42—The amino acid (SEQ ID NO: 3) and nucleic acid (SEQ ID NO: 4) sequences of pro-stem bromelain (pro-SB) used herein.

FIG. 43—SDS-PAGE showing cleavage of pro-SB by active ananain.

40 μg of pro-SB was mixed with 1.6 μg of active ananain, in a final volume of 160 μl of AMT buffer, pH 5.0, with 12 mM L-Cys. The solutions were incubated at room temperature (RT) and at every designated time point of 0, 1, 2, 3, 5, 10 and 15 min (lanes 2-8), a 20 μl of solution was subjected to SDS-PAGE analysis, as described previously. As control, a sample with 5 μg of pro-SB (lane 9) and another with 0.2 μg of active ananain (lane 10) in 20 μl of AMT buffer with 12 mM L-Cys was respectively incubated at RT for 120 min. Lane 1=molecular weight markers.

Figure 44:
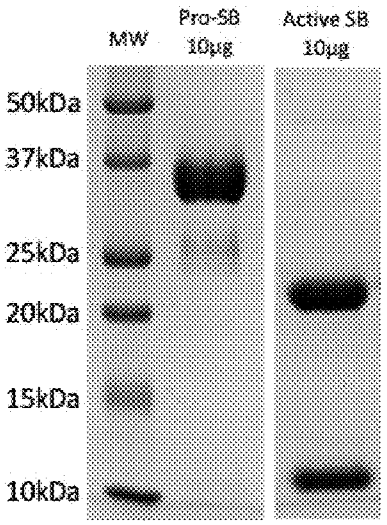

FIG. 44—SDS-PAGE showing cleavage of pro-SB by immobilized ananain.

2 mg of active ananain was immobilized in a 5 ml HiTrap™ NHS-Activated HP affinity column (GE Health, IL, USA). A 5 mg of pro-SB was resuspended in 5 ml AMT buffer, pH 5.0, with 12 mM L-Cys. The pro-SB was circulated through the ananain-immobilized column at RT for overnight. The collected activated SB was subject to SDS-PAGE analysis and was confirmed to be fully cleaved. Lane 1=molecular weight markers.

Figure 45:
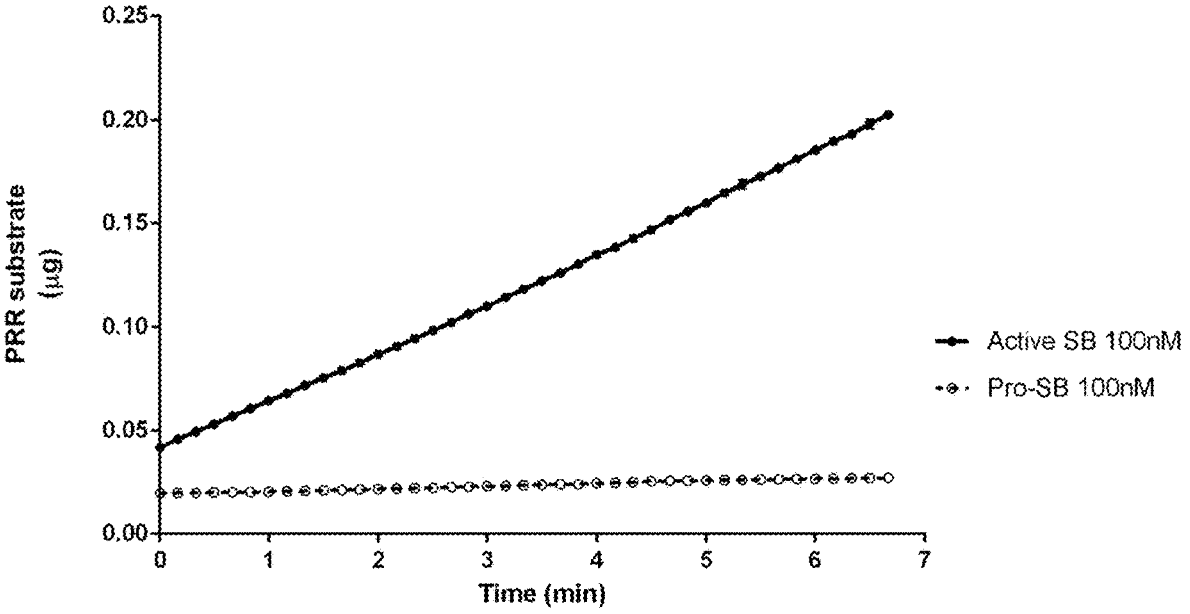

FIG. 45—Proteolytic activity of activated stem bromelain against PRR substrate The proteolytic activity of activated stem bromelain was assayed using the fluorescent tripeptidyl substrate, PRR, in the form of MeOC-GGG-PRR-GG-DPA-KK-$NH_2$ (SEQ ID NO: 8) (Mimotopes, Clayton, Australia). Following the activation process, 200 nM of activated SB was mixed with a final concentration of 25 μM of PRR in a final volume of 100 μl AAB. Cleavage at the core PRR tripeptide releases the fluorescence of the MeOC donor group, which is detected by using a POLARstar fluorescent plate reader, as described previously. Solid circles line=proteolysis due to active stem bromelain. Open circles=proteolysis due to pro-SB.

FIG. 46—The amino acid (SEQ ID NO: 5) and nucleic acid (SEQ ID NO: 6) sequences of pro-fruit bromelain (pro-FB) used herein.

Figure 47:
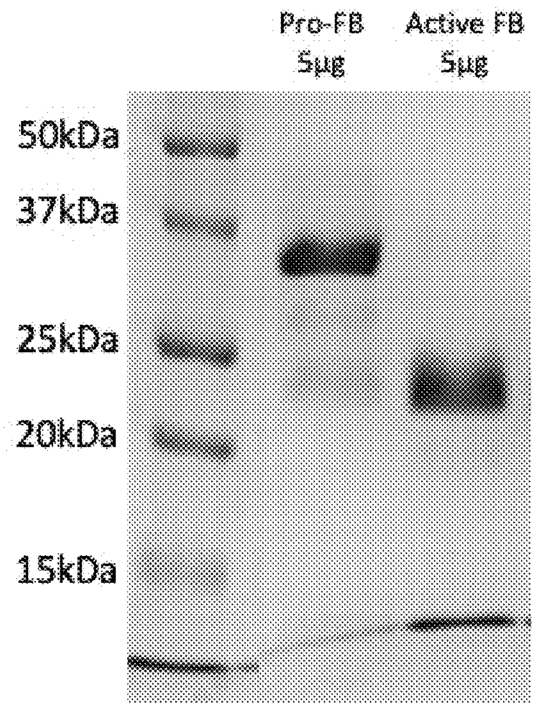

FIG. 47—SDS-PAGE showing cleavage of pro-FB by immobilized ananain.

2 mg of active ananain was immobilized in a 5 ml HiTrap™ NHS-Activated HP affinity column (GE Health, IL, USA). A 5 mg of pro-FB was resuspended in 5 ml AMT buffer, pH 5.0, with 12 mM L-Cys. The pro-FB was circulated through the ananain-immobilized column at RT for overnight. The collected activated FB was subject to SDS-PAGE analysis and was confirmed to be fully cleaved. Lane 1=molecular weight markers.

Figure 48:
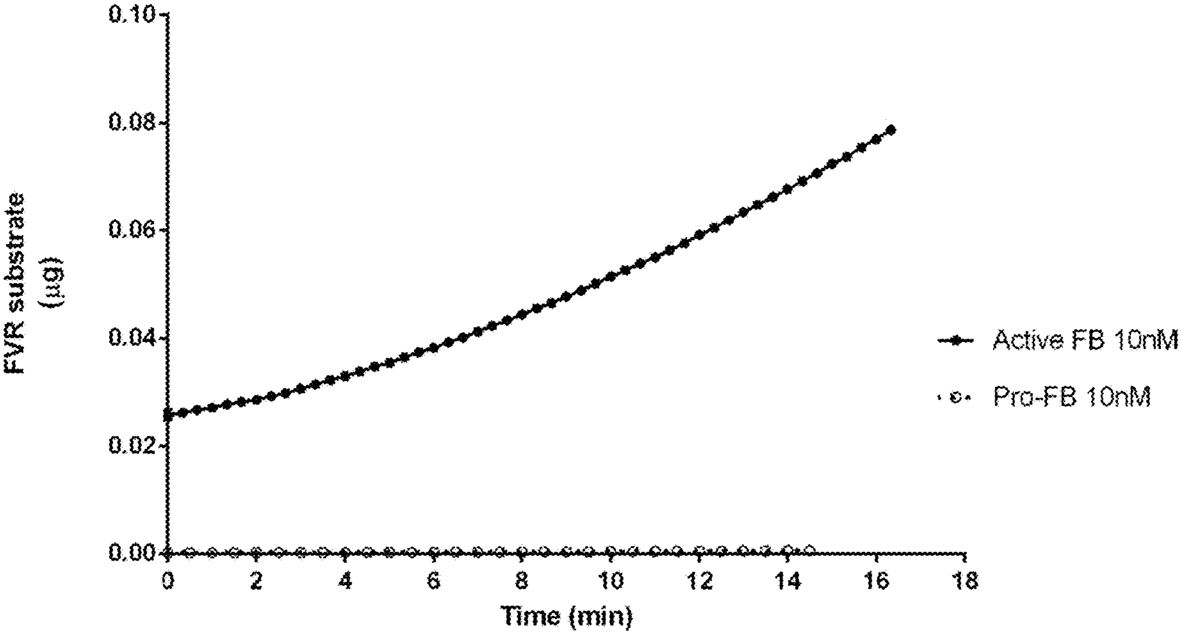

FIG. 48—Proteolytic activity of activated fruit bromelain against FVR-AMC-substrate.

Activity of activated fruit bromelain was measured using a fluorescent tripeptidyl substrate, FVR-7-amino-4-methylcoumarin (FVR-AMC). A 10 nM of activated FB was mixed with a final concentration of 50 μM of FVR-AMC in a final volume of 100 μl AAB buffer, pH 4.0. Cleavage of FVR-AMC releases the fluorescent AMC group, which is detected by using a POLARstar fluorescent plate reader, using excitation and emission wavelengths of 360 and 460 nm, respectively. Solid circles=proteolysis due to active fruit bromelain. Open circles=proteolysis due to pro-FB.

DETAILED DESCRIPTION OF THE INVENTION

Definitions

The following definitions are presented to better define the present invention and as a guide for those of ordinary skill in the art in the practice of the present invention.

Unless otherwise specified, all technical and scientific terms used herein are to be understood as having the same meanings as is understood by one of ordinary skill in the relevant art to which this disclosure pertains.

It is also believed that practice of the present invention can be performed using standard cell biology, microbiological, molecular biology, pharmacology and biochemistry protocols and procedures as known in the art, and as described, for example in numerous commonly available reference materials relevant in the art to which this disclosure pertains.

Examples of definitions of common terms in microbiology, molecular biology and biochemistry can be found in Methods for General and Molecular Microbiology, 3rd Edition, C. A. Reddy, et al. (eds.), ASM Press, (2008); Encyclopedia of Microbiology, 2nd ed., Joshua Lederburg, (ed.), Academic Press, (2000); Microbiology By Cliffs Notes, I. Edward Alcamo, Wiley, (1996); Dictionary of Microbiology and Molecular Biology, Singleton et al. (2d ed.) (1994); Biology of Microorganisms 11$^{th}$ ed., Brock et al., Pearson Prentice Hall, (2006); Genes IX, Benjamin Lewin, Jones & Bartlett Publishing, (2007); The Encyclopedia of Molecular Biology, Kendrew et al. (eds.), Blackwell Science Ltd., (1994) and Molecular Biology and Biotechnology: a Comprehensive Desk Reference, Robert A. Meyers (ed.), VCH Publishers, Inc., (1995).

The term "pro-ananain" as used herein means the non-proteolytic zymogen form of ananain. In some embodiments, pro-ananain comprises the amino acid sequence of SEQ ID NO: 1.

The terms "ananain" and "mature ananain" are used interchangeably herein and mean the proteolytic, activated ananain enzyme having the ability to catalyse proteolysis.

The term "pro-bromelain" as used herein means the non-proteolytic zymogen form of bromelain. In some embodiments, pro-bromelain is pro-stem bromelain. In some embodiments, pro-stem bromelain comprises the amino acid sequence of SEQ ID NO: 3. In some embodiments, pro-bromelain is pro-fruit bromelain. In some embodiments, pro-fruit bromelain comprises the amino acid sequence of SEQ ID NO: 5.

The terms "bromelain" and "mature bromelain" are used interchangeably herein and mean the proteolytic, activated bromelain enzyme having the ability to catalyse proteolysis.

The terms "recombinant pro-ananain" and "recombinant pro-bromelain" refer to polypeptides that are expressed in vitro from a polynucleotide sequence that is removed from sequences that surround it in its natural context and/or is recombined with sequences that are not present in its natural context. A "recombinant" pro-ananain or pro-bromelain polypeptide sequence is produced by translation from a "recombinant" polynucleotide sequence.

The term "a stable composition" as used herein means a composition, preferably a dry composition comprising pro-ananain or pro-bromelain or both that can be reconstituted as an aqueous composition comprising active ananain or active bromelain or both. In one embodiment a stable composition is a lyophilized composition as described herein, comprising a pharmaceutically acceptable buffer, NaCl, a pharmaceutically acceptable reducing agent and recombinant pro-ananain or recombinant pro-bromelain or both.

The term "about" when used in connection with a referenced numeric indication means the referenced numeric indication plus or minus up to 10% of that referenced numeric indication. For example, "about 100" means from 90 to 110 and "about six" means from 5.4 to 6.6.

The term "comprising" as used in this specification means "consisting at least in part of". When interpreting statements in this specification that include that term, the features, prefaced by that term in each statement, all need to be present but other features can also be present. Related terms such as "comprise" and "comprised" are to be interpreted in the same manner.

The term "consisting essentially of" as used herein means the specified materials or steps and those that do not materially affect the basic and novel characteristic(s) of the claimed invention.

The term "consisting of" as used herein means the specified materials or steps of the claimed invention, excluding any element, step, or ingredient not specified in the claim.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

DESCRIPTION

The core event in the activation of cysteine proteases is the cleavage at the peptide bond between the inhibitory sequence and the protease domain. Cleavage can be mediated by either the active site of a protease molecule itself (and subsequently toward other pro-enzyme molecules of the same kind known as 'auto-activation') or by a protease having a different identity ('trans-activation'). Protease activation also involves interfering with the molecular interactions between the inhibitory sequence and the protease domain. Such interactions usually involve strong hydrogen bonding, charge interaction and Van der Waal force among residues of both structures. Accordingly, the buffer conditions (type, concentration and pH value) of a protease solution are important as they affect the strength of such inhibitory interactions. Moreover, it is generally believed that a reducing agent is critical for the proteolytic activity of cysteine proteases, either for its contribution on preventing oxidation of the active Cys residue, and/or by affecting the overall secondary structure of the protein. What the inventors have surprisingly found is that for cysteine proteases undergoing auto-activation, such as pro-ananain, careful selection of the types of buffers and reducing agents and accurate determining the concentrations of the components, has enabled them to identify physiologically relevant conditions for the activation of pro-ananain, including the activation of pro-ananain that has been stabilized in a dry powder.

In this project, a number of physiologically relevant buffers (phosphate citrate, sodium acetate, MES, sodium citrate and PBS) and reducing agents (L-Cys and ascorbic acid) were selected for developing the activation formula of pro-ananain comprised in the compositions described herein. In order to maximise the applicability of the final formula for humans and animals, the concentrations of the buffer and reducing agent were brought to the minimal range, yet the activation of pro-ananain achieves the maximal range at physiological temperatures of humans. Further, the established pro-ananain formula substantially encompasses the physiological pH range of humans from weak acidic (pH 5) to neutral (pH 7.5). Moreover, the inventors have surprisingly found that a composition as described herein, comprising an activation formula of pro-ananain, can be lyophilized to provide a stable composition comprising pro-ananain. That stable composition can then be reconstituted with water to provide a composition as described herein, comprising active ananain. The inventors believe that the provision of a lyophilized form of a pro-ananain formula as described herein is a cost-effective means of delivering pure and stable pro-ananain with a long shelf-life. Following reconstitution in purified water, the water-reconstituted formula provides an easy and effective way to rapidly generate active ananain having sustained proteolytic activity. In addition, the inventors have surprisingly found that the trans-activation of pro-stem bromelain and pro-fruit bromelain can be mediated by active ananain and used this knowledge to develop an activation formula comprising both pro-stem and pro-fruit bromelain enzymes.

Based on the surprising findings detailed herein the inventors believe that formulations of pure, stable ananain and/or ananain+bromelain can be provided for various research and therapeutic purposes, particularly at physiologically relevant conditions and using pharmaceutically acceptable constituents.

Accordingly, in one aspect the invention relates to a composition comprising:

(a) recombinant pro-ananain
(b) a pharmaceutically acceptable buffer
(c) a pharmaceutically acceptable reducing agent, and
(d) sodium chloride (NaCl),
  wherein the concentration of the buffer is about 5 to about 30 mM,
  wherein the concentration of the reducing agent is about 10 to about 30 mM,
  wherein the concentration of the NaCl is about 140 to about 160 mM and,
  wherein the pH of the composition is about 5.0 to about 6.0.

In one embodiment the recombinant pro-ananain comprises a polypeptide comprising at least 70% amino acid identity to (SEQ ID NO: 1).

In one embodiment the recombinant pro-ananain comprises at least 75%, preferably 80%, 85%, 90%, 95%, preferably 99% amino acid identity to (SEQ ID NO: 1).

In one embodiment the recombinant pro-ananain comprises (SEQ ID NO: 1). In one embodiment the recombinant pro-ananain consists or consists essentially of (SEQ ID NO: 1).

In one embodiment the composition is an aqueous composition.

In one embodiment the composition comprises about 0.001 mg/mL to about 10 mg/mL recombinant pro-ananain. In one embodiment the composition comprises about 1 mg/mL recombinant pro-ananain.

In one embodiment the composition comprises about 0.001 mM to about 1 mM recombinant pro-ananain. In one embodiment the composition comprises about 0.027 mM pro-ananain.

In one embodiment the buffer is selected from the group consisting of phosphate-citrate, sodium acetate, sodium citrate and 2-(N-morpholino)ethanesulfonic acid (MES) buffers.

In one embodiment the buffer comprises citric acid.

In one embodiment the buffer comprises sodium hydrogen phosphate.

In one embodiment the buffer is phosphate-citrate.

In one embodiment the composition comprises about 5 mM to about 20 mM phosphate-citrate buffer.

In one embodiment the composition comprises about 5.5 mM to about 17 mM phosphate-citrate buffer.

In one embodiment the composition comprises about 6 mM to about 15 mM phosphate-citrate buffer.

In one embodiment the composition comprises about 6.5 mM to about 13 mM phosphate-citrate buffer.

In one embodiment the composition comprises about 7 mM to about 11 mM phosphate-citrate buffer.

In one embodiment the composition comprises about 7.5 mM to about 10 mM phosphate-citrate buffer.

In one embodiment the composition comprises about 8 mM to about 9 mM phosphate-citrate buffer.

In one embodiment the composition comprises about 8 mM phosphate-citrate buffer.

In one embodiment the composition comprises 5 mM to 20 mM phosphate-citrate buffer.

In one embodiment the composition comprises 5.5 mM to 17 mM phosphate-citrate buffer.

In one embodiment the composition comprises 6 mM to 15 mM phosphate-citrate buffer.

In one embodiment the composition comprises 6.5 mM to 13 mM phosphate-citrate buffer.

In one embodiment the composition comprises 7 mM to 11 mM phosphate-citrate buffer.

In one embodiment the composition comprises 7.5 mM to 10 mM phosphate-citrate buffer.

In one embodiment the composition comprises 8 mM to 9 mM phosphate-citrate buffer.

In one embodiment the composition comprises 8 mM phosphate-citrate buffer.

In one embodiment the buffer comprises an acid salt.

In one embodiment the acid salt is sodium citrate.

In one embodiment the composition comprises about 5 mM to about 20 mM sodium citrate buffer.

In one embodiment the composition comprises about 5.5 mM to about 17 mM sodium citrate buffer.

In one embodiment the composition comprises about 6 mM to about 15 mM sodium citrate buffer.

In one embodiment the composition comprises about 6.5 mM to about 13 mM sodium citrate buffer.

In one embodiment the composition comprises about 7 mM to about 11 mM sodium citrate buffer.

In one embodiment the composition comprises about 7.5 mM to about 10 mM sodium citrate buffer.

In one embodiment the composition comprises about 8 mM to about 9 mM sodium citrate buffer.

In one embodiment the composition comprises about 8 mM sodium citrate buffer.

In one embodiment the composition comprises 5 mM to 20 mM sodium citrate buffer.

In one embodiment the composition comprises 5.5 mM to 17 mM sodium citrate buffer.

In one embodiment the composition comprises 6 mM to 15 mM sodium citrate buffer.

In one embodiment the composition comprises 6.5 mM to 13 mM sodium citrate buffer.

In one embodiment the composition comprises 7 mM to 11 mM sodium citrate buffer.

In one embodiment the composition comprises 7.5 mM to 10 mM sodium citrate buffer.

In one embodiment the composition comprises 8 mM to 9 mM sodium citrate buffer.

In one embodiment the composition comprises 8 mM sodium citrate buffer.

In one embodiment the buffer is an acetate buffer.

In one embodiment the acetate buffer is sodium acetate.

In one embodiment the composition comprises about 3 mM to about 18 mM sodium acetate buffer.

In one embodiment the composition comprises about 3.5 mM to about 16 mM sodium acetate buffer.

In one embodiment the composition comprises about 4 mM to about 14 mM sodium acetate buffer.

In one embodiment the composition comprises about 4.5 mM to about 12 mM sodium acetate buffer.

In one embodiment the composition comprises about 5 mM to about 10 mM sodium acetate buffer.

In one embodiment the composition comprises about 5.5 mM to about 8 mM sodium acetate buffer.

In one embodiment the composition comprises about 6 mM to about 7 mM sodium acetate buffer.

In one embodiment the composition comprises about 6 mM sodium acetate buffer.

In one embodiment the composition comprises 3 mM to 18 mM sodium acetate buffer.

In one embodiment the composition comprises 3.5 mM to 16 mM sodium acetate buffer.

In one embodiment the composition comprises 4 mM to 14 mM sodium acetate buffer.

In one embodiment the composition comprises 4.5 mM to 12 mM sodium acetate buffer.

In one embodiment the composition comprises 5 mM to 10 mM sodium acetate buffer.

In one embodiment the composition comprises 5.5 mM to 8 mM sodium acetate buffer.

In one embodiment the composition comprises 6 mM to 7 mM sodium acetate buffer.

In one embodiment the composition comprises 6 mM sodium acetate buffer.

In one embodiment the buffer is 2-(N-morpholino)ethanesulfonic acid (MES).

In one embodiment the composition comprises about 5 mM to about 25 mM MES buffer.

In one embodiment the composition comprises about 7 mM to about 23 mM MES buffer.

In one embodiment the composition comprises about 9 mM to about 21 mM MES buffer.

In one embodiment the composition comprises about 11 mM to about 19 mM MES buffer.

In one embodiment the composition comprises about 13 mM to about 17 mM MES buffer.

In one embodiment the composition comprises about 14 mM to about 16 mM MES buffer.

In one embodiment the composition comprises about 15 mM MES buffer.

In one embodiment the composition comprises 5 mM to 25 mM MES buffer.

In one embodiment the composition comprises 7 mM to 23 mM MES buffer.

In one embodiment the composition comprises 9 mM to 21 mM MES buffer.

In one embodiment the composition comprises 11 mM to 19 mM MES buffer.

In one embodiment the composition comprises 13 mM to 17 mM MES buffer.

In one embodiment the composition comprises 14 mM to 16 mM MES buffer.

In one embodiment the composition comprises 15 mM MES buffer.

In one embodiment the buffer is phosphate buffered saline (PBS).

In one embodiment the reducing agent is L-cysteine (L-Cys).

In one embodiment the composition comprises about 8 mM phosphate citrate buffer and about 10 mM to about 30 mM L-Cys.

In one embodiment the composition comprises about 8 mM phosphate citrate buffer and about 11 mM to about 28 mM L-Cys.

In one embodiment the composition comprises about 8 mM phosphate citrate buffer and about 12 mM to about 26 mM L-Cys.

In one embodiment the composition comprises about 8 mM phosphate citrate buffer and about 13 mM to about 24 mM L-Cys.

In one embodiment the composition comprises about 8 mM phosphate citrate buffer and about 14 mM to about 22 mM L-Cys.

In one embodiment the composition comprises about 8 mM phosphate citrate buffer and about 15 mM to about 20 mM L-Cys.

In one embodiment the composition comprises about 8 mM phosphate citrate buffer and about 16 mM to about 18 mM L-Cys.

In one embodiment the composition comprises about 8 mM phosphate citrate buffer and about 17 mM L-Cys.

In one embodiment the composition comprises about 8 mM phosphate citrate buffer and about 16 mM L-Cys.

In one embodiment the composition comprises 8 mM phosphate citrate buffer and 10 mM to 30 mM L-Cys.

In one embodiment the composition comprises 8 mM phosphate citrate buffer and 11 mM to 28 mM L-Cys.

In one embodiment the composition comprises 8 mM phosphate citrate buffer and 12 mM to 26 mM L-Cys.

In one embodiment the composition comprises 8 mM phosphate citrate buffer and 13 mM to 24 mM L-Cys.

In one embodiment the composition comprises 8 mM phosphate citrate buffer and 14 mM to 22 mM L-Cys.

In one embodiment the composition comprises 8 mM phosphate citrate buffer and 15 mM to 20 mM L-Cys.

In one embodiment the composition comprises 8 mM phosphate citrate buffer and 16 mM to 18 mM L-Cys.

In one embodiment the composition comprises 8 mM phosphate citrate buffer and 17 mM L-Cys.

In one embodiment the composition comprises 8 mM phosphate citrate buffer and 16 mM L-Cys.

In one embodiment the composition comprises about 8 mM sodium citrate buffer and about 10 mM to about 30 mM L-Cys.

In one embodiment the composition comprises about 8 mM sodium citrate buffer and about 12 mM to about 29 mM L-Cys.

In one embodiment the composition comprises about 8 mM sodium citrate buffer and about 14 mM to about 28 mM L-Cys.

In one embodiment the composition comprises about 8 mM sodium citrate buffer and about 16 mM to about 27 mM L-Cys.

In one embodiment the composition comprises about 8 mM sodium citrate buffer and about 18 mM to about 26 mM L-Cys.

In one embodiment the composition comprises about 8 mM sodium citrate buffer and about 20 mM to about 24 mM L-Cys.

In one embodiment the composition comprises about 8 mM sodium citrate buffer and about 21 mM to about 23 mM L-Cys.

In one embodiment the composition comprises about 8 mM sodium citrate buffer and about 22 mM L-Cys.

In one embodiment the composition comprises 8 mM sodium citrate buffer and 10 mM to 30 mM L-Cys.

In one embodiment the composition comprises 8 mM sodium citrate buffer and 12 mM to 29 mM L-Cys.

In one embodiment the composition comprises 8 mM sodium citrate buffer and 14 mM to 28 mM L-Cys.

In one embodiment the composition comprises 8 mM sodium citrate buffer and 16 mM to 27 mM L-Cys.

In one embodiment the composition comprises 8 mM sodium citrate buffer and 18 mM to 26 mM L-Cys.

In one embodiment the composition comprises 8 mM sodium citrate buffer and 20 mM to 24 mM L-Cys.

In one embodiment the composition comprises 8 mM sodium citrate buffer and 21 mM to 23 mM L-Cys.

In one embodiment the composition comprises 8 mM sodium citrate buffer and 22 mM L-Cys.

In one embodiment the composition comprises about 6 mM sodium acetate buffer and about 5 mM to about 19 mM L-Cys.

In one embodiment the composition comprises about 6 mM sodium acetate buffer and about 6 mM to about 18 mM L-Cys.

In one embodiment the composition comprises about 6 mM sodium acetate buffer and about 7 mM to about 17 mM L-Cys.

In one embodiment the composition comprises about 6 mM sodium acetate buffer and about 8 mM to about 16 mM L-Cys.

In one embodiment the composition comprises about 6 mM sodium acetate buffer and about 9 mM to about 15 mM L-Cys.

In one embodiment the composition comprises about 6 mM sodium acetate buffer and about 10 mM to about 14 mM L-Cys.

In one embodiment the composition comprises about 6 mM sodium acetate buffer and about 11 mM to about 13 mM L-Cys.

In one embodiment the composition comprises about 6 mM sodium acetate buffer and about 12 mM L-Cys.

In one embodiment the composition comprises 6 mM sodium acetate buffer and 5 mM to 19 mM L-Cys.

In one embodiment the composition comprises 6 mM sodium acetate buffer and 6 mM to 18 mM L-Cys.

In one embodiment the composition comprises 6 mM sodium acetate buffer and 7 mM to 17 mM L-Cys.

In one embodiment the composition comprises 6 mM sodium acetate buffer and 8 mM to 16 mM L-Cys.

In one embodiment the composition comprises 6 mM sodium acetate buffer and 9 mM to 15 mM L-Cys.

In one embodiment the composition comprises 6 mM sodium acetate buffer and 10 mM to 14 mM L-Cys.

In one embodiment the composition comprises 6 mM sodium acetate buffer and 11 mM to 13 mM L-Cys.

In one embodiment the composition comprises 6 mM sodium acetate buffer and 12 mM L-Cys.

In one embodiment the composition comprises about 15 mM MES buffer and about 7 mM to about 21 mM L-Cys.

In one embodiment the composition comprises about 15 mM MES buffer and about 8 mM to about 20 mM L-Cys.

In one embodiment the composition comprises about 15 mM MES buffer and about 9 mM to about 19 mM L-Cys.

In one embodiment the composition comprises about 15 mM MES buffer and about 10 mM to about 18 mM L-Cys.

In one embodiment the composition comprises about 15 mM MES buffer and about 11 mM to about 17 mM L-Cys.

In one embodiment the composition comprises about 15 mM MES buffer and about 12 mM to about 16 mM L-Cys.

In one embodiment the composition comprises about 15 mM MES buffer and about 13 mM to about 15 mM L-Cys.

In one embodiment the composition comprises about 15 mM MES buffer and about 14 mM L-Cys.

In one embodiment the composition comprises 15 mM MES buffer and 7 mM to 21 mM L-Cys.

In one embodiment the composition comprises 15 mM MES buffer and 8 mM to 20 mM L-Cys.

In one embodiment the composition comprises 15 mM MES buffer and 9 mM to 19 mM L-Cys.

In one embodiment the composition comprises 15 mM MES buffer and 10 mM to 18 mM L-Cys.

In one embodiment the composition comprises 15 mM MES buffer and 11 mM to 17 mM L-Cys.

In one embodiment the composition comprises 15 mM MES buffer and 12 mM to 16 mM L-Cys.

In one embodiment the composition comprises 15 mM MES buffer and 13 mM to 15 mM L-Cys.

In one embodiment the composition comprises 15 mM MES buffer and 14 mM L-Cys.

In one embodiment the composition comprises PBS and about 8 mM to about 22 mM L-Cys.

In one embodiment the composition comprises PBS and about 9 mM to about 21 mM L-Cys.

In one embodiment the composition comprises PBS and about 10 mM to about 20 mM L-Cys.

In one embodiment the composition comprises PBS and about 11 mM to about 19 mM L-Cys.

In one embodiment the composition comprises PBS and about 12 mM to about 18 mM L-Cys.

In one embodiment the composition comprises PBS and about 13 mM to about 17 mM L-Cys.

In one embodiment the composition comprises PBS and about 14 mM to about 16 mM L-Cys.

In one embodiment the composition comprises PBS and about 15 mM L-Cys.

In one embodiment the composition comprises PBS and 8 mM to 22 mM L-Cys.

In one embodiment the composition comprises PBS and 9 mM to 21 mM L-Cys.

In one embodiment the composition comprises PBS and 10 mM to 20 mM L-Cys.

In one embodiment the composition comprises PBS and 11 mM to 19 mM L-Cys.

In one embodiment the composition comprises PBS and 12 mM to 18 mM L-Cys.

In one embodiment the composition comprises PBS and 13 mM to 17 mM L-Cys.

In one embodiment the composition comprises PBS and 14 mM to 16 mM L-Cys.

In one embodiment the composition comprises PBS and 15 mM L-Cys.

In one embodiment the composition comprises about 150 mM NaCl.

In one embodiment the composition comprises 140 mM to 160 mM NaCl.

In one embodiment the composition comprises 150 mM NaCl.

In one embodiment the composition has a pH of about 5.1 to about 5.9.

In one embodiment the composition has a pH of about 5.2 to about 5.8.

In one embodiment the composition has a pH of about 5.3 to about 5.7.

In one embodiment the composition has a pH of about 5.4 to about 5.6.

In one embodiment the composition has a pH of about 5.5.

In one embodiment the composition has a pH of 5.0 to 6.0

In one embodiment the composition has a pH of 5.1 to 5.9

In one embodiment the composition has a pH of 5.2 to 5.8.

In one embodiment the composition has a pH of 5.3 to 5.7.

In one embodiment the composition has a pH of 5.4 to 5.6

In one embodiment the composition has a pH of 5.5.

In one embodiment the composition is a dry composition.

In one embodiment the dry composition is a freeze-dried composition.

In one embodiment the dry composition is a lyophilized composition.

In one embodiment the dry composition is in the form of a powder.

In one embodiment the freeze-dried or lyophilized composition comprises about 0.001 to about 10 mg recombinant pro-ananain.

In one embodiment the composition further comprises (e) pro-bromelain. In one embodiment the pro-bromelain is at a ratio of pro-ananain:pro-bromelain of about 1:25 to about 1:50.

In one embodiment the pro-bromelain is recombinant pro-bromelain.

In one embodiment the pro-bromelain is stem pro-bromelain. In one embodiment the pro-bromelain is fruit pro-bromelain.

In one embodiment the composition consists essentially of (a), (b), (c) and (d) in any of the embodiments set out above. In one embodiment the composition consists essentially of (a), (b), (c), (d) and (e) in any of the embodiments set out above.

In one embodiment the composition consists of (a), (b), (c) and (d) in any of the embodiments set out above. In one embodiment the composition consists of (a), (b), (c), (d) and (e) in any of the embodiments set out above.

Methods

In another aspect the invention relates to a method of making a composition comprising recombinant pro-ananain, the method comprising combining:

(a) recombinant pro-ananain with (b) a pharmaceutically acceptable buffer (c) a pharmaceutically acceptable reducing agent, and (d) sodium chloride (NaCl), wherein the concentration of the buffer is about 5 to about 30 mM, wherein the concentration of the reducing agent is about 10 to about 30 mM, wherein the concentration of the NaCl is about 140 to about 160 mM and, wherein the pH of the composition is about 5.0 to about 6.0.

In one embodiment the recombinant pro-ananain comprises a polypeptide comprising at least 70% amino acid identity to (SEQ ID NO: 1).

In one embodiment the recombinant pro-ananain comprises at least 75%, preferably 80%, 85%, 90%, 95%, preferably 99% amino acid identity to (SEQ ID NO: 1).

In one embodiment the recombinant pro-ananain comprises (SEQ ID NO: 1). In one embodiment the recombinant pro-ananain consists or consists essentially of (SEQ ID NO: 1).

In one embodiment the composition is an aqueous composition.

In one embodiment the composition comprises about 0.001 to about 10 mg/mL recombinant pro-ananain. In one embodiment the composition comprises about 1.0 mg/mL recombinant pro-ananain.

In one embodiment the composition comprises about 0.001 mM to about 1 mM pro-ananain. In one embodiment the composition comprises about 0.027 mM pro-ananain.

In one embodiment the buffer is selected from the group consisting of phosphate-citrate, sodium acetate, sodium citrate and 2-(N-morpholino)ethanesulfonic acid (MES) buffers.

In one embodiment the buffer comprises citric acid.

In one embodiment the buffer comprises sodium hydrogen phosphate.

In one embodiment the buffer is phosphate-citrate.

In one embodiment the composition comprises about 5 mM to about 20 mM phosphate-citrate buffer.

In one embodiment the composition comprises about 5.5 mM to about 17 mM phosphate-citrate buffer.

In one embodiment the composition comprises about 6 mM to about 15 mM phosphate-citrate buffer.

In one embodiment the composition comprises about 6.5 mM to about 13 mM phosphate-citrate buffer.

In one embodiment the composition comprises about 7 mM to about 11 mM phosphate-citrate buffer.

In one embodiment the composition comprises about 7.5 mM to about 10 mM phosphate-citrate buffer.

In one embodiment the composition comprises about 8 mM to about 9 mM phosphate-citrate buffer.

In one embodiment the composition comprises about 8 mM phosphate-citrate buffer.

In one embodiment the composition comprises 5 mM to 20 mM phosphate-citrate buffer.

In one embodiment the composition comprises 5.5 mM to 17 mM phosphate-citrate buffer.

In one embodiment the composition comprises 6 mM to 15 mM phosphate-citrate buffer.

In one embodiment the composition comprises 6.5 mM to 13 mM phosphate-citrate buffer.

In one embodiment the composition comprises 7 mM to 11 mM phosphate-citrate buffer.

In one embodiment the composition comprises 7.5 mM to 10 mM phosphate-citrate buffer.

In one embodiment the composition comprises 8 mM to 9 mM phosphate-citrate buffer.

In one embodiment the composition comprises 8 mM phosphate-citrate buffer.

In one embodiment the buffer comprises an acid salt.

In one embodiment the acid salt is sodium citrate.

In one embodiment the composition comprises about 5 mM to about 20 mM sodium citrate buffer.

In one embodiment the composition comprises about 5.5 mM to about 17 mM sodium citrate buffer.

In one embodiment the composition comprises about 6 mM to about 15 mM sodium citrate buffer.

In one embodiment the composition comprises about 6.5 mM to about 13 mM sodium citrate buffer.

In one embodiment the composition comprises about 7 mM to about 11 mM sodium citrate buffer.

In one embodiment the composition comprises about 7.5 mM to about 10 mM sodium citrate buffer.

In one embodiment the composition comprises about 8 mM to about 9 mM sodium citrate buffer.

In one embodiment the composition comprises about 8 mM sodium citrate buffer.

In one embodiment the composition comprises 5 mM to 20 mM sodium citrate buffer.

In one embodiment the composition comprises 5.5 mM to 17 mM sodium citrate buffer.

In one embodiment the composition comprises 6 mM to 15 mM sodium citrate buffer.

In one embodiment the composition comprises 6.5 mM to 13 mM sodium citrate buffer.

In one embodiment the composition comprises 7 mM to 11 mM sodium citrate buffer.

In one embodiment the composition comprises 7.5 mM to 10 mM sodium citrate buffer.

In one embodiment the composition comprises 8 mM to 9 mM sodium citrate buffer.

In one embodiment the composition comprises 8 mM sodium citrate buffer.

In one embodiment the buffer is an acetate buffer.

In one embodiment the acetate buffer is sodium acetate.

In one embodiment the composition comprises about 3 mM to about 18 mM sodium acetate buffer.

In one embodiment the composition comprises about 3.5 mM to about 16 mM sodium acetate buffer.

In one embodiment the composition comprises about 4 mM to about 14 mM sodium acetate buffer.

In one embodiment the composition comprises about 4.5 mM to about 12 mM sodium acetate buffer.

In one embodiment the composition comprises about 5 mM to about 10 mM sodium acetate buffer.

In one embodiment the composition comprises about 5.5 mM to about 8 mM sodium acetate buffer.

In one embodiment the composition comprises about 6 mM to about 7 mM sodium acetate buffer.

In one embodiment the composition comprises about 6 mM sodium acetate buffer.

In one embodiment the composition comprises 3 mM to 18 mM sodium acetate buffer.

In one embodiment the composition comprises 3.5 mM to 16 mM sodium acetate buffer.

In one embodiment the composition comprises 4 mM to 14 mM sodium acetate buffer.

In one embodiment the composition comprises 4.5 mM to 12 mM sodium acetate buffer.

In one embodiment the composition comprises 5 mM to 10 mM sodium acetate buffer.

In one embodiment the composition comprises 5.5 mM to 8 mM sodium acetate buffer.

In one embodiment the composition comprises 6 mM to 7 mM sodium acetate buffer.

In one embodiment the composition comprises 6 mM sodium acetate buffer.

In one embodiment the buffer is 2-(N-morpholino)ethanesulfonic acid (MES).

In one embodiment the composition comprises about 5 mM to about 25 mM MES buffer.

In one embodiment the composition comprises about 7 mM to about 23 mM MES buffer.

In one embodiment the composition comprises about 9 mM to about 21 mM MES buffer.

In one embodiment the composition comprises about 11 mM to about 19 mM MES buffer.

In one embodiment the composition comprises about 13 mM to about 17 mM MES buffer.

In one embodiment the composition comprises about 14 mM to about 16 mM MES buffer.

In one embodiment the composition comprises about 15 mM MES buffer.

In one embodiment the composition comprises 5 mM to 25 mM MES buffer.

In one embodiment the composition comprises 7 mM to 23 mM MES buffer.

In one embodiment the composition comprises 9 mM to 21 mM MES buffer.

In one embodiment the composition comprises 11 mM to 19 mM MES buffer.

In one embodiment the composition comprises 13 mM to 17 mM MES buffer.

In one embodiment the composition comprises 14 mM to 16 mM MES buffer.

In one embodiment the composition comprises 15 mM MES buffer.

In one embodiment the buffer is phosphate buffered saline (PBS).

In one embodiment the reducing agent is L-cysteine (L-Cys).

In one embodiment the composition comprises about 8 mM phosphate citrate buffer and about 10 mM to about 30 mM L-Cys.

In one embodiment the composition comprises about 8 mM phosphate citrate buffer and about 11 mM to about 28 mM L-Cys.

In one embodiment the composition comprises about 8 mM phosphate citrate buffer and about 12 mM to about 26 mM L-Cys.

In one embodiment the composition comprises about 8 mM phosphate citrate buffer and about 13 mM to about 24 mM L-Cys.

In one embodiment the composition comprises about 8 mM phosphate citrate buffer and about 14 mM to about 22 mM L-Cys.

In one embodiment the composition comprises about 8 mM phosphate citrate buffer and about 15 mM to about 20 mM L-Cys.

In one embodiment the composition comprises about 8 mM phosphate citrate buffer and about 16 mM to about 18 mM L-Cys.

In one embodiment the composition comprises about 8 mM phosphate citrate buffer and about 17 mM L-Cys.

In one embodiment the composition comprises about 8 mM phosphate citrate buffer and about 16 mM L-Cys.

In one embodiment the composition comprises 8 mM phosphate citrate buffer and 10 mM to 30 mM L-Cys.

In one embodiment the composition comprises 8 mM phosphate citrate buffer and 11 mM to 28 mM L-Cys.

In one embodiment the composition comprises 8 mM phosphate citrate buffer and 12 mM to 26 mM L-Cys.

In one embodiment the composition comprises 8 mM phosphate citrate buffer and 13 mM to 24 mM L-Cys.

In one embodiment the composition comprises 8 mM phosphate citrate buffer and 14 mM to 22 mM L-Cys.

In one embodiment the composition comprises 8 mM phosphate citrate buffer and 15 mM to 20 mM L-Cys.

In one embodiment the composition comprises 8 mM phosphate citrate buffer and 16 mM to 18 mM L-Cys.

In one embodiment the composition comprises 8 mM phosphate citrate buffer and 17 mM L-Cys.

In one embodiment the composition comprises 8 mM phosphate citrate buffer and 16 mM L-Cys.

In one embodiment the composition comprises about 8 mM sodium citrate buffer and about 10 mM to about 30 mM L-Cys.

In one embodiment the composition comprises about 8 mM sodium citrate buffer and about 12 mM to about 29 mM L-Cys.

In one embodiment the composition comprises about 8 mM sodium citrate buffer and about 14 mM to about 28 mM L-Cys.

In one embodiment the composition comprises about 8 mM sodium citrate buffer and about 16 mM to about 27 mM L-Cys.

In one embodiment the composition comprises about 8 mM sodium citrate buffer and about 18 mM to about 26 mM L-Cys.

In one embodiment the composition comprises about 8 mM sodium citrate buffer and about 20 mM to about 24 mM L-Cys.

In one embodiment the composition comprises about 8 mM sodium citrate buffer and about 21 mM to about 23 mM L-Cys.

In one embodiment the composition comprises about 8 mM sodium citrate buffer and about 22 mM L-Cys.

In one embodiment the composition comprises 8 mM sodium citrate buffer and 10 mM to 30 mM L-Cys.

In one embodiment the composition comprises 8 mM sodium citrate buffer and 12 mM to 29 mM L-Cys.

In one embodiment the composition comprises 8 mM sodium citrate buffer and 14 mM to 28 mM L-Cys.

In one embodiment the composition comprises 8 mM sodium citrate buffer and 16 mM to 27 mM L-Cys.

In one embodiment the composition comprises 8 mM sodium citrate buffer and 18 mM to 26 mM L-Cys.

In one embodiment the composition comprises 8 mM sodium citrate buffer and 20 mM to 24 mM L-Cys.

In one embodiment the composition comprises 8 mM sodium citrate buffer and 21 mM to 23 mM L-Cys.

In one embodiment the composition comprises 8 mM sodium citrate buffer and 22 mM L-Cys.

In one embodiment the composition comprises about 6 mM sodium acetate buffer and about 5 mM to about 19 mM L-Cys.

In one embodiment the composition comprises about 6 mM sodium acetate buffer and about 6 mM to about 18 mM L-Cys.

In one embodiment the composition comprises about 6 mM sodium acetate buffer and about 7 mM to about 17 mM L-Cys.

In one embodiment the composition comprises about 6 mM sodium acetate buffer and about 8 mM to about 16 mM L-Cys.

In one embodiment the composition comprises about 6 mM sodium acetate buffer and about 9 mM to about 15 mM L-Cys.

In one embodiment the composition comprises about 6 mM sodium acetate buffer and about 10 mM to about 14 mM L-Cys.

In one embodiment the composition comprises about 6 mM sodium acetate buffer and about 11 mM to about 13 mM L-Cys.

In one embodiment the composition comprises about 6 mM sodium acetate buffer and about 12 mM L-Cys.

In one embodiment the composition comprises 6 mM sodium acetate buffer and 5 mM to 19 mM L-Cys.

In one embodiment the composition comprises 6 mM sodium acetate buffer and 6 mM to 18 mM L-Cys.

In one embodiment the composition comprises 6 mM sodium acetate buffer and 7 mM to 17 mM L-Cys.

In one embodiment the composition comprises 6 mM sodium acetate buffer and 8 mM to 16 mM L-Cys.

In one embodiment the composition comprises 6 mM sodium acetate buffer and 9 mM to 15 mM L-Cys.

In one embodiment the composition comprises 6 mM sodium acetate buffer and 10 mM to 14 mM L-Cys.

In one embodiment the composition comprises 6 mM sodium acetate buffer and 11 mM to 13 mM L-Cys.

In one embodiment the composition comprises 6 mM sodium acetate buffer and 12 mM L-Cys.

In one embodiment the composition comprises about 15 mM MES buffer and about 7 mM to about 21 mM L-Cys.

In one embodiment the composition comprises about 15 mM MES buffer and about 8 mM to about 20 mM L-Cys.

In one embodiment the composition comprises about 15 mM MES buffer and about 9 mM to about 19 mM L-Cys.

In one embodiment the composition comprises about 15 mM MES buffer and about 10 mM to about 18 mM L-Cys.

In one embodiment the composition comprises about 15 mM MES buffer and about 11 mM to about 17 mM L-Cys.

In one embodiment the composition comprises about 15 mM MES buffer and about 12 mM to about 16 mM L-Cys.

In one embodiment the composition comprises about 15 mM MES buffer and about 13 mM to about 15 mM L-Cys.

In one embodiment the composition comprises about 15 mM MES buffer and about 14 mM L-Cys.

In one embodiment the composition comprises 15 mM MES buffer and 7 mM to 21 mM L-Cys.

In one embodiment the composition comprises 15 mM MES buffer and 8 mM to 20 mM L-Cys.

In one embodiment the composition comprises 15 mM MES buffer and 9 mM to 19 mM L-Cys.

In one embodiment the composition comprises 15 mM MES buffer and 10 mM to 18 mM L-Cys.

In one embodiment the composition comprises 15 mM MES buffer and 11 mM to 17 mM L-Cys.

In one embodiment the composition comprises 15 mM MES buffer and 12 mM to 16 mM L-Cys.

In one embodiment the composition comprises 15 mM MES buffer and 13 mM to 15 mM L-Cys.

In one embodiment the composition comprises 15 mM MES buffer and 14 mM L-Cys.

In one embodiment the composition comprises PBS and about 8 mM to about 22 mM L-Cys.

In one embodiment the composition comprises PBS and about 9 mM to about 21 mM L-Cys.

In one embodiment the composition comprises PBS and about 10 mM to about 20 mM L-Cys.

In one embodiment the composition comprises PBS and about 11 mM to about 19 mM L-Cys.

In one embodiment the composition comprises PBS and about 12 mM to about 18 mM L-Cys.

In one embodiment the composition comprises PBS and about 13 mM to about 17 mM L-Cys.

In one embodiment the composition comprises PBS and about 14 mM to about 16 mM L-Cys.

In one embodiment the composition comprises PBS and about 15 mM L-Cys.

In one embodiment the composition comprises PBS and 8 mM to 22 mM L-Cys.

In one embodiment the composition comprises PBS and 9 mM to 21 mM L-Cys.

In one embodiment the composition comprises PBS and 10 mM to 20 mM L-Cys.

In one embodiment the composition comprises PBS and 11 mM to 19 mM L-Cys.

In one embodiment the composition comprises PBS and 12 mM to 18 mM L-Cys.

In one embodiment the composition comprises PBS and 13 mM to 17 mM L-Cys.

In one embodiment the composition comprises PBS and 14 mM to 16 mM L-Cys.

In one embodiment the composition comprises PBS and 15 mM L-Cys.

In one embodiment the composition comprises about 150 mM NaCl.

In one embodiment the composition comprises 140 mM to 160 mM NaCl.

In one embodiment the composition comprises 150 mM NaCl.

In one embodiment the composition has a pH of about 5.1 to about 5.9.

In one embodiment the composition has a pH of about 5.2 to about 5.8.

In one embodiment the composition has a pH of about 5.3 to about 5.7.

In one embodiment the composition has a pH of about 5.4 to about 5.6.

In one embodiment the composition has a pH of about 5.5.

In one embodiment the composition has a pH of 5.0 to 6.0

In one embodiment the composition has a pH of 5.1 to 5.9

In one embodiment the composition has a pH of 5.2 to 5.8.

In one embodiment the composition has a pH of 5.3 to 5.7.

In one embodiment the composition has a pH of 5.4 to 5.6

In one embodiment the composition has a pH of 5.5.

In one embodiment the composition further comprises (e) pro-bromelain. In one embodiment the pro-bromelain is at a ratio of pro-ananain:pro-bromelain of about 1:25 to about 1:50.

In one embodiment the pro-bromelain is recombinant pro-bromelain.

In one embodiment the pro-bromelain is stem pro-bromelain.

In one embodiment the pro-bromelain is fruit pro-bromelain.

In one embodiment the composition consists essentially of (a), (b), (c) and (d) in any of the embodiments set out above.

In one embodiment the composition consists essentially of (a), (b), (c), (d) and (e) in any of the embodiments set out above.

In one embodiment the composition consists of (a), (b), (c) and (d) in any of the embodiments set out above.

In one embodiment the composition consists of (a), (b), (c), (d) and (e) in any of the embodiments set out above.

In one embodiment the method comprises drying the composition after combining (a), (b) (c) and (d).

In one embodiment the method comprises drying the composition after combining (a), (b) (c), (d) and (e).

In one embodiment drying comprises freeze-drying the composition.

In one embodiment drying comprises lyophilizing the composition.

In one embodiment drying comprises sufficient drying to form a powder.

In one embodiment the dried composition is a stable composition.

In another aspect the invention relates to a method of providing a recombinant active ananain composition, the method comprising heating an aqueous composition of the invention to about 30° C. to about 44° C. for at least 5 min.

In one embodiment the aqueous composition is a dry composition of the invention that has been reconstituted in water or a buffer as described herein.

In one embodiment heating is in vitro.

In one embodiment heating is to at least 30° C., 31° C., 32° C., 33° C., 34° C., 35° C., 36° C., 37° C., 38° C., 39° C., 40° C., 41° C., 42° C., 43° C. or at least 44° C.

In one embodiment heating is to about 30° C., 31° C., 32° C., 33° C., 34° C., 35° C., 36° C., 37° C., 38° C., 39° C., 40° C., 41° C., 42° C., 43° C. or about 44° C.

In one embodiment heating is to 30° C., 31° C., 32° C., 33° C., 34° C., 35° C., 36° C., 37° C., 38° C., 39° C., 40° C., 41° C., 42° C., 43° C. or 44° C.

In one embodiment heating is to about 30.5° C. to about 43.5° C.

In one embodiment heating is to about 31° C. to about 43° C.

In one embodiment heating is to about 31.5° C. to about 42.5° C.

In one embodiment heating is to about 32° C. to about 42° C.

In one embodiment heating is to about 32.5° C. to about 41.5° C.

In one embodiment heating is to about 33° C. to about 41° C.

In one embodiment heating is to about 33.5° C. to about 40.5° C.

In one embodiment heating is to about 34° C. to about 40° C.

In one embodiment heating is to about 34.5° C. to about 39.5° C.

In one embodiment heating is to about 35° C. to about 39° C.

In one embodiment heating is to about 35.5° C. to about 38.5° C.

In one embodiment heating is to about 36° C. to about 38° C.

In one embodiment heating is to about 36.5° C. to about 37.5° C.

In one embodiment heating is to about 37° C.

In one embodiment heating to about 37° C. is heating in vivo in an animal.

In one embodiment the animal is a mammal. In one embodiment the mammal is a non-human mammal. In one embodiment the mammal is a human.

In one embodiment heating is to 30° C. to 44° C.

In one embodiment heating is to 30.5° C. to 43.5° C.

In one embodiment heating is to 31° C. to 43° C.

In one embodiment heating is to 31.5° C. to 42.5° C.

In one embodiment heating is to 32° C. to 42° C.

In one embodiment heating is to 32.5° C. to 41.5° C.

In one embodiment heating is to 33° C. to 41° C.

In one embodiment heating is to 33.5° C. to 40.5° C.

In one embodiment heating is to 34° C. to 40° C.

In one embodiment heating is to 34.5° C. to 39.5° C.

In one embodiment heating is to 35° C. to 39° C.

In one embodiment heating is to 35.5° C. to 38.5° C.

In one embodiment heating is to 36° C. to 38° C.

In one embodiment heating is to 36.5° C. to 37.5° C.

In one embodiment heating is to 37° C.

In one embodiment heating to 37° C. is heating in vivo in an animal.

In one embodiment the animal is a mammal. In one embodiment the mammal is a non-human mammal. In one embodiment the mammal is a human.

In one embodiment heating is for at least 6, 7, 8, 9, 10, 11, 12, 13, 14, 15, 16, 17, 18, 19, 20, 21, 22, 23, 24, 25, 26, 27, 28, 29 or 30 minutes.

In one embodiment heating is for about 5 to about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95 100, 110, 115, or 120 minutes.

In one embodiment heating is for 5 to 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95 100, 110, 115, or 120 minutes.

In one embodiment heating is for about 10 to about 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95 100, 110, 115, or 120 minutes.

In one embodiment heating is for 10 to 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95 100, 110, 115, or 120 minutes.

In one embodiment heating is for about 5 to about 30 minutes.

In one embodiment heating is for about 5 to about 25 minutes.

In one embodiment heating is for about 5 to about 20 minutes.

In one embodiment heating is for about 5 to about 15 minutes.

In one embodiment heating is for about 5 to about 10 minutes.

In one embodiment heating is for about 10 to about 30 minutes.

In one embodiment heating is for about 10 to about 25 minutes.

In one embodiment heating is for about 10 to about 20 minutes.

In one embodiment heating is for about 10 to about 15 minutes.

In one embodiment heating is for about 15 to about 30 minutes.

In one embodiment heating is for about 15 to about 25 minutes.

In one embodiment heating is for about 15 to about 20 minutes.

In one embodiment heating is for about 20 to about 30 minutes.

In one embodiment heating is for about 20 to about 25 minutes.

In one embodiment heating is for about 20 minutes.

In one embodiment heating is for about 25 minutes.

In one embodiment heating is for about 30 minutes.

In one embodiment heating is for 5 to 30 minutes.

In one embodiment heating is for 5 to 25 minutes.

In one embodiment heating is for 5 to 20 minutes.

In one embodiment heating is for 5 to 15 minutes.

In one embodiment heating is for 5 to 10 minutes.

In one embodiment heating is for 10 to 30 minutes.

In one embodiment heating is for 10 to 25 minutes.

In one embodiment heating is for 10 to 20 minutes.

In one embodiment heating is for 10 to 15 minutes.

In one embodiment heating is for 15 to 30 minutes.

In one embodiment heating is for 15 to 25 minutes.

In one embodiment heating is for 15 to 20 minutes.

In one embodiment heating is for 20 to 30 minutes.

In one embodiment heating is for 20 to 25 minutes.

In one embodiment heating is for 20 minutes.

In one embodiment heating is for 25 minutes.

In one embodiment heating is for 30 minutes.

In one embodiment heating in vitro is to between about 30° C. and about 40° C. for about 15 min.

In one embodiment heating in vitro is to between 30° C. and 40° C. for 15 min.

In one embodiment the aqueous composition comprises phosphate citrate or sodium acetate buffer and the pH of the aqueous composition after heating is about 5.0 to about 6.0.

In one embodiment the aqueous composition comprises phosphate citrate or sodium acetate buffer and the pH of the aqueous composition after heating is about 5.1 to about 5.9.

In one embodiment the aqueous composition comprises phosphate citrate or sodium acetate buffer and the pH of the aqueous composition after heating is about 5.2 to about 5.8.

In one embodiment the aqueous composition comprises phosphate citrate or sodium acetate buffer and the pH of the aqueous composition after heating is about 5.3 to about 5.7.

In one embodiment the aqueous composition comprises phosphate citrate or sodium acetate buffer and the pH of the aqueous composition after heating is about 5.4 to about 5.6.

In one embodiment the aqueous composition comprises phosphate citrate or sodium acetate buffer and the pH of the aqueous composition after heating is about 5.5.

In one embodiment the aqueous composition comprises phosphate citrate or sodium acetate buffer and the pH of the aqueous composition after heating is 5.0 to 6.0

In one embodiment the aqueous composition comprises phosphate citrate or sodium acetate buffer and the pH of the aqueous composition after heating is 5.1 to 5.9

In one embodiment the aqueous composition comprises phosphate citrate or sodium acetate buffer and the pH of the aqueous composition after heating is 5.2 to 5.8.

In one embodiment the aqueous composition comprises phosphate citrate or sodium acetate buffer and the pH of the aqueous composition after heating is 5.3 to 5.7.

In one embodiment the aqueous composition comprises phosphate citrate or sodium acetate buffer and the pH of the aqueous composition after heating is 5.4 to 5.6

In one embodiment the aqueous composition comprises phosphate citrate or sodium acetate buffer and the pH of the aqueous composition after heating is 5.5.

In one embodiment the aqueous composition comprises sodium citrate buffer and the pH of the aqueous composition after heating is about 4.5 to about 5.5.

In one embodiment the aqueous composition comprises sodium citrate buffer and the pH of the aqueous composition after heating is about 4.6 to about 5.4.

In one embodiment the aqueous composition comprises sodium citrate buffer and the pH of the aqueous composition after heating is about 4.7 to about 5.3.

In one embodiment the aqueous composition comprises sodium citrate buffer and the pH of the aqueous composition after heating is about 4.8 to about 5.2.

In one embodiment the aqueous composition comprises sodium citrate buffer and the pH of the aqueous composition after heating is about 4.9 to about 5.1.

In one embodiment the aqueous composition comprises sodium citrate buffer and the pH of the aqueous composition after heating is about 4.95.

In one embodiment the aqueous composition comprises sodium citrate buffer and the pH of the aqueous composition after heating is 4.5 to 5.5.

In one embodiment the aqueous composition comprises sodium citrate buffer and the pH of the aqueous composition after heating is 4.6 to 5.4.

In one embodiment the aqueous composition comprises sodium citrate buffer and the pH of the aqueous composition after heating is 4.7 to 5.3.

In one embodiment the aqueous composition comprises sodium citrate buffer and the pH of the aqueous composition after heating is 4.8 to 5.2.

In one embodiment the aqueous composition comprises sodium citrate buffer and the pH of the aqueous composition after heating is 4.9 to 5.1.

In one embodiment the aqueous composition comprises sodium citrate buffer and the pH of the aqueous composition after heating is 4.95.

In one embodiment the aqueous composition comprises PBS and the pH of the aqueous composition after heating is about 5.5 to about 6.5.

In one embodiment the aqueous composition comprises PBS and the pH of the aqueous composition after heating is about 5.6 to about 6.4.

In one embodiment the aqueous composition comprises PBS and the pH of the aqueous composition after heating is about 5.7 to about 6.3.

In one embodiment the aqueous composition comprises PBS and the pH of the aqueous composition after heating is about 5.8 to about 6.2.

In one embodiment the aqueous composition comprises PBS and the pH of the aqueous composition after heating is about 5.9 to about 6.1.

In one embodiment the aqueous composition comprises PBS and the pH of the aqueous composition after heating is about 6.

In one embodiment the aqueous composition comprises PBS and the pH of the aqueous composition after heating is 5.5 to 6.5.

In one embodiment the aqueous composition comprises PBS and the pH of the aqueous composition after heating is 5.6 to 6.4.

In one embodiment the aqueous composition comprises PBS and the pH of the aqueous composition after heating is 5.7 to 6.3.

In one embodiment the aqueous composition comprises PBS and the pH of the aqueous composition after heating is 5.8 to 6.2.

In one embodiment the aqueous composition comprises PBS and the pH of the aqueous composition after heating is 5.9 to 6.1.

In one embodiment the aqueous composition comprises PBS and the pH of the aqueous composition after heating is 6.

In one embodiment the aqueous composition comprises MES and the pH of the aqueous composition after heating is about 6.9 to about 7.9.

In one embodiment the aqueous composition comprises PBS and the pH of the aqueous composition after heating is about 7.0 to about 7.8.

In one embodiment the aqueous composition comprises PBS and the pH of the aqueous composition after heating is about 7.1 to about 7.7.

In one embodiment the aqueous composition comprises PBS and the pH of the aqueous composition after heating is about 7.2 to about 7.6.

In one embodiment the aqueous composition comprises PBS and the pH of the aqueous composition after heating is about 7.3 to about 7.5.

In one embodiment the aqueous composition comprises PBS and the pH of the aqueous composition after heating is about 7.4.

In one embodiment the aqueous composition comprises MES and the pH of the aqueous composition after heating is 6.9 to 7.9.

In one embodiment the aqueous composition comprises PBS and the pH of the aqueous composition after heating is 7.0 to 7.8.

In one embodiment the aqueous composition comprises PBS and the pH of the aqueous composition after heating is 7.1 to 7.7.

In one embodiment the aqueous composition comprises PBS and the pH of the aqueous composition after heating is 7.2 to 7.6.

In one embodiment the aqueous composition comprises PBS and the pH of the aqueous composition after heating is 7.3 to 7.5.

In one embodiment the aqueous composition comprises PBS and the pH of the aqueous composition after heating is 7.4.

In one embodiment the composition comprises active bromelain, preferably active stem bromelain or active fruit bromelain.

In another aspect the invention relates to method of providing a recombinant active ananain composition, the method comprising reconstituting a dry composition of the invention to form an aqueous composition and heating the aqueous composition to at least 30° C.

In one embodiment the dry composition is a freeze-dried composition.

In one embodiment the dry composition is a lyophilized composition.

In one embodiment the dry composition is a powder.

In one embodiment the dry composition is a stable composition.

In one embodiment reconstituting comprises combining a sufficient amount of the dry composition in a sufficient amount of water or buffer to achieve a final concentration of about 0.001 to about 10 mg/mL of recombinant pro-ananain in the aqueous composition.

In one embodiment the final concentration is about 1 mg/mL.

In one embodiment reconstituting is in a buffer as described herein for any other aspect of the invention.

In one embodiment the buffer is PBS.

In one embodiment reconstituting is in water.

In one embodiment heating is in vitro.

In one embodiment heating in vitro is to between about 30° C. and about 40° C. for about 5 to about 20 min, preferably about 10 to 15 min, preferably about 15 min.

In one embodiment heating in vitro is to between 30° C. and 40° C. for 5 to 20 min, preferably 10 to 15 min, preferably 15 min.

In one embodiment heating is to about 37° C. in vivo in an animal.

In one embodiment the animal is a mammal. In one embodiment the mammal is a non-human mammal. In one embodiment the mammal is a human.

In one embodiment the final concentration of recombinant active ananain in the aqueous composition after heating is about 000.1 mg/mL to about 10 mg/mL, preferably about 1.0 mg/mL.

Specifically contemplated as additional embodiments of the aspect of the invention directed to providing a recombinant active ananain composition comprising reconstituting a dry composition of the invention to form an aqueous composition and heating the aqueous composition to at least 30° C., are all of the embodiments set out herein related to the aspect of the invention that is a method of providing a recombinant active ananain composition comprising heating an aqueous composition of the invention to about 30° C. to about 44° C. for at least 5 min, particularly the embodiments related to heating, buffer and pH.

In another aspect the invention relates to a method of activating bromelain comprising (a) reconstituting a dry composition comprising at least 0.1% recombinant pro-ananain and >about 5% recombinant pro-bromelain and a physiological buffer in water to form an aqueous composition comprising about 4 to about 20 mM buffer, and (b), heating the reconstituted composition in vivo to about 37° C. wherein the reconstituted composition comprises a pH of about 5.0 to about 7.5.

In one embodiment the dry composition comprises about 0.1% to about 5% pro-ananain and >about 5% pro-bromelain.

In one embodiment the dry composition comprises about 0.1% pro-ananain and >5% pro-bromelain.

In one embodiment the pro-bromelain is pro-stem bromelain or pro-fruit bromelain, preferably pro-stem bromelain.

In one embodiment the recombinant pro-stem bromelain comprises a polypeptide comprising at least 70% amino acid identity to (SEQ ID NO: 3).

In one embodiment the recombinant pro-stem bromelain comprises at least 75%, preferably 80%, 85%, 90%, 95%, preferably 99% amino acid identity to (SEQ ID NO: 3).

In one embodiment the recombinant pro-stem bromelain comprises (SEQ ID NO: 3). In one embodiment the recombinant pro-stem bromelain consists or consists essentially of (SEQ ID NO: 3).

In one embodiment the recombinant pro-fruit bromelain comprises a polypeptide comprising at least 70% amino acid identity to (SEQ ID NO: 5).

In one embodiment the recombinant pro-fruit bromelain comprises at least 75%, preferably 80%, 85%, 90%, 95%, preferably 99% amino acid identity to (SEQ ID NO: 5).

In one embodiment the recombinant pro-fruit bromelain comprises (SEQ ID NO: 5). In one embodiment the recombinant pro-fruit bromelain consists or consists essentially of (SEQ ID NO: 5).

In one embodiment heating in vivo is heating in an animal. In one embodiment heating in the animal is to about 37° C.

In one embodiment heating in vivo comprises injecting the aqueous composition into the animal.

In one embodiment the animal is a mammal. In one embodiment the mammal is a non-human mammal. In one embodiment the mammal is a human.

Specifically contemplated as additional embodiments of the aspect of the invention related to an in vivo method of activating stem bromelain, are all of the embodiments set out herein related to the aspect of the invention that is a method of providing a recombinant active ananain composition comprising reconstituting a dry composition of the invention to form an aqueous composition and heating the aqueous composition to at least 30° C., including those embodiments contemplated in the aspect of the invention that is a method of providing a recombinant active ananain composition comprising heating an aqueous composition of the invention to about 30° C. to about 44° C. for at least 5 min, particularly the embodiments related to heating, buffer and pH.

In another aspect the invention relates to a method of activating bromelain comprising (a) reconstituting a dry composition comprising at least 0.1% recombinant pro-ananain and about >5% recombinant pro-bromelain and a physiological buffer in water to form an aqueous composition comprising about 4 to about 20 mM buffer, and (b), heating the aqueous composition in vitro to between about 30° C. and about 40° C. for about 5 to about 20 mins, wherein the reconstituted composition comprises a pH of between about 5 and about 7.5.

In one embodiment heating is for about 10 to about 15 min.

In one embodiment heating is for about 15 min.

In one embodiment the dry composition comprises about 0.1% to about 5% pro-ananain and >about 5% pro-bromelain.

In one embodiment the dry composition comprises 0.1% pro-ananain and >5% pro-bromelain.

In one embodiment the pro-bromelain is pro-stem bromelain or pro-fruit bromelain, preferably pro-stem bromelain.

In one embodiment heating in vivo is heating in an animal. In one embodiment heating in the animal is to about 37° C.

In one embodiment heating in vivo comprises injecting the aqueous composition into the animal.

In one embodiment the animal is a mammal. In one embodiment the mammal is a non-human mammal. In one embodiment the mammal is a human.

Specifically contemplated as additional embodiments of the aspect of the invention related to a method of activating bromelain, are all of the embodiments set out herein related to the aspects of the invention that are a method of providing a recombinant active ananain composition comprising heating an aqueous composition of the invention to about 30° C. to about 44° C. for at least 5 min and a method of providing a recombinant active ananain composition, the method comprising reconstituting a dry composition of the invention to form an aqueous composition and heating the aqueous composition to at least 30° C., particularly including the embodiments related to pro-bromelain, heating, buffer and pH.

The invention will now be illustrated in a non-limiting way by reference to the following examples.

1. EXAMPLES

Preparation of Pro-Ananain

Constructing Plasmid Vector for Pro-Ananain

The coding sequence of pro-ananain disclosed herein was developed based on UniProt P80884. It excludes the N-terminal signal sequence of 24 aa, and encodes for an inhibitory sequence of 98 aa (S25-S122 of SEQ ID NO: 2)), and the active cysteine protease sequence of 223 aa (V123-I345 of SEQ ID NO: 2), followed by a pair of stop codons. The coding sequence was optimized for *E. coli* expression by GeneScript (NJ, USA) using the OptimumGene™ algorithm, and was incorporated into a PUC57 vector with an NdeI and a BamHI restriction enzyme cleavage sites at the N- and C-terminus, respectively, by GeneScript.

The PUC57-pro-ananain construct was digested with NdeI and BamHI restriction enzymes to generate the genetic insert of pro-ananain, which was purified after running in a 0.8% agarose gel. The insert was then incorporated into a pET28a plasmid to produce the final pET28a-pro-ananain construct, which was amplified in *E. coli* strain DH5a (Thermo-Fisher, MA, USA). The amplified pET28a-pro-ananain construct was extracted using the Wizard DNA Purification kit (Promega, WI, USA), and the gene sequence of the construct was confirmed by Macrogen (Seoul, Korea) (FIG. 1).

Expression of Recombinant Pro-Ananain

The BL21(DE3)pLysS *E. coli* cells (Novagen, Darmstadt, Germany) were transformed with the pET28a-pro-ananain plasmid and were grown in 1 L of Luria-Bertani (LB) medium at 37° C. to an OD600 value of 0.6-0.8. The inclusion bodies of pro-ananain were induced with 0.1 mM of Isopropyl β-d-1-thiogalactopyranoside (IPTG) for 4 hr. The induced cells were harvested by centrifugation at 6,000 µg for 20 min and re-suspended in a buffer containing 50 mM tris(hydroxymethyl)aminomethane (Tris), 20 mM Ethylenediaminetetraacetic acid (EDTA), pH7.4. The inclusion bodies were released from the induced cells by sonication. After three washes in buffer containing 50 mM Tris, 20 mM EDTA with 1M Sodium Chloride (NaCl), the inclusion bodies were dissolved in 40 ml of 8M urea, 100 mM Tris, pH 8.3, with 2 mM Dithiothreitol (DTT). The concentration of unfolded pro-ananain in the inclusion bodies was estimated by sodium dodecyl sulfate-polyacrylamide gel electrophoresis (SDS-PAGE), using 12.5% SDS-gel and a Bovine serum albumin (BSA) standard as reference of concentration. The typical yield of unfolded pro-ananain was 150 mg/L of cell culture.

Refolding Recombinant Pro-Ananain and Protein Purification 150 mg of unfolded pro-ananain was diluted dropwise at 4° C. into 5 L of refolding buffer, containing 50 mM Tris, 500 mM L-Arginine, 300 mM NaCl at pH 9.0, with 3 mM reduced glutathione and 1 mM oxidised glutathione. The dilution was stirred at 4° C. for a further 48 hr. Refolded protein was then concentrated using the Vivaflow 200 Cross Flow Cassette (Sartorius, Goettingen, Germany). The concentrated protein was dialysed overnight in 15 L of 50 mM Tris 50 at pH 9.0 at 4° C.

The dialysed protein was loaded into a 5 ml HisTrap™ FastFlow column (GE Health). The bound protein was eluted using 20 mM to 500 mM imidazole at pH 9.0. The eluted protein was pooled and subjected to size-exclusion chromatography using a HiLoad™ 16/60 Superdex™ 75 column (GE Health, IL, USA) equilibrated with one of the five buffers:

(1) 10 mM Phosphate citrate, 150 mM NaCl, pH 5.5;
(2) 10 mM Sodium acetate, 150 mM NaCl, pH 5.5;
(3) 10 mM 2-(N-morpholino)ethanesulfonic acid (MES), 150 mM NaCl, pH 5.5;
(4) 10 mM Sodium citrate, 150 mM NaCl, pH 5.5;
(5) Phosphate-buffered saline (PBS), pH 7.4.

Typically, pro-ananain was eluted in the fractions peaked at around 63 ml for each of the buffers above, at a yield of 30-40 mg per refold.

Characterizing the Activation Conditions for Pro-Ananain

General Process for Activating Pro-Ananain

Pro-ananain was purified and concentrated to 5 mg/ml in buffers (1)-(5), respectively. The final concentration of pro-ananain in any activation reaction was set at 1 mg/ml (which is equal to 27 µM pro-ananain). The pH value of the final reaction mixture, the concentration of buffer, the concentration of reducing agent and the temperature were adjusted to the designated values for each individual reaction according to the experiment as set out in the following examples. The reaction mixture was set up ice-cold at 20 µl per reaction and then incubated for 20 min. at 37° C. or at the designated temperature.

SDS-PAGE was applied to visualize active ananain resulting from the activation process. After activation, a 10 µl of reaction mixture was sampled and immediately mixed with 100 mM iodoacetamide to stop the reaction. Pro-ananain and active ananain are displayed as a 36 kDa and a 24 kDa band, respectively, in a 12.5% SDS-gel. See example (1)-(5) below.

Proteolytic Activity Assay for the Activated Ananain

Proteolytic activity of activated ananain was measured using a fluorescent tripeptidyl substrate, PLQ, in the form of MeOC-GGG-PLQ-GG-DPA-KK-$NH_2$ (SEQ ID NO: 7) (Mimotopes, Clayton, Australia). Typically, following the activation process, a 1 μl sample of reaction mixture (started with 27 μM pro-ananain) was taken and immediately diluted to 2,700× (which gives 0-10 nM active ananain) with an activity assay buffer (AAB, 100 mM sodium acetate, 200 mM NaCl, 2 mM EDTA, pH5.5). The ananain dilution was mixed with an equal volume of 50 μM PLQ substrate in AAB to detect the proteolytic activity of ananain (maximum final concentration 5 nM). Cleavage at the core PLQ tripeptide tethered between the fluorescent MeOC donor group and the DPA quencher moiety releases the fluorescence of the MeOC donor group, which is detected by using a POLARstar fluorescent plate reader (BMG Labtech, Offenburg, Germany) with excitation and emission wavelengths of 320 nm and 420 nm, respectively. The initial rate of proteolysis of substrate is measured as the slope of the linear portion of the progressive curve and is converted to the unit of μg PLQ molecules per min. See example (1)-(5) below.

Example 1—Activation of Pro-Ananain in Phosphate-Citrate Buffer Impact of pH The reaction mixture was prepared ice-cold with 1 mg/ml pro-ananain at 20 μl per reaction, at a final concentration of 10 mM phosphate citrate, 150 mM NaCl and 20 mM freshly added L-Cysteine (L-Cys). The pH value of the reaction mixture was adjusted to the designated pH value of 3.1, 3.2, 3.3, 3.4, 3.5, 3.6, 3.7, 4.0, 4.5, 4.8, 5.0, 5.4, 5.5, 5.6, 6.0, 6.5, 7.0 and 7.4, respectively. The reaction mixtures were incubated at 37° C. for 20 min, followed by visualization of reaction products using SDS-PAGE (FIG. 2) and measurement of the proteolytic activity of activated ananain (FIG. 3) as described previously.

Within the pH range (2.6-7.6) for phosphate citrate, pro-ananain activation in the 10 mM phosphate citrate buffer prefers an acidic pH<6.0 (FIG. 2). At a higher pH value than 6.5, cleavage of pro-ananain does not occur at the correct activation site in the inhibitory sequence (confirmed by N-terminal sequencing, results not shown), resulting in a 26 kDa band and a weak band of 32 kDa. These cleavage products did not yield proteolytic activity of ananain (FIG. 3). The highest level of ananain proteolytic activity was observed in phosphate citrate buffer at pH 4.8-5.6 (FIG. 3). For convenience, pH 5.5 is suggested to be the optimal pH value for pro-ananain activation in phosphate citrate buffer.

Impact of the Concentration of Phosphate Citrate

The reaction mixture was prepared ice-cold with 1 mg/ml pro-ananain at 20 μl per reaction, at a final concentration of 150 mM NaCl and 20 mM freshly added L-Cys, with 3.0, 4.0, 5.0, 6.0, 7.0, 8.0, 9.0, 10.0, 11.0, 12.0, 13.0, 14.0, 15.0, 16.0, 17.0, 18.0 and 20.0 mM phosphate citrate, respectively, at pH 5.5. The reaction mixtures were incubated at 37° C. for 20 min, followed by visualization of reaction products using SDS-PAGE (FIG. 4) and measurement of the proteolytic activity of activated ananain (FIG. 5) as described previously.

The results from this assay show that the highest level of pro-ananain activation is observed at 7-10 mM phosphate citrate (FIGS. 4 and 5). For convenience, 8 mM phosphate citrate is used for phosphate citrate buffer.

Impact of the Concentration of L-Cys in Phosphate Citrate Buffer

The reaction mixture was prepared ice-cold with 1 mg/ml pro-ananain at 20 μl per reaction, at a final concentration of 8 mM phosphate citrate, 150 mM NaCl, pH 5.5, with freshly added L-Cys at a final of 0, 10, 12, 14, 16, 18, 20, 22, 24, 26, 28 and 30 mM, respectively. The reaction mixtures were incubated at 37° C. for 20 min, followed visualization of reaction products using SDS-PAGE (FIG. 6) and measurement of the proteolytic activity of activated ananain (FIG. 7) as described previously.

The results from the of pro-ananain activation show that without L-Cys, pro-ananain remained the zymogenic form (FIG. 6). This assay also illustrates that at a concentration of L-Cys higher than 22 mM, the active ananain in the phosphate citrate buffer became unstable and was further cleaved into fragments of lower molecular weights, which reflects a loss of ananain activity (FIG. 7). Based on the measurement of the proteolytic activity of activated ananain, the optimal concentration of L-Cys was set to 16 mM for the phosphate citrate buffer (FIG. 7).

Pro-Ananain Activation in Phosphate Citrate Buffer at Varied Temperature

The reaction mixture was prepared ice-cold with 1 mg/ml pro-ananain at 20 μl per reaction, at a final concentration of 8 mM phosphate citrate, 150 mM NaCl, pH 5.5, with freshly added L-Cys at a final of 16 mM. The reaction mixtures were incubated at 0, 24, 26, 28, 30, 32, 34, 36, 37, 38, 40, 42, 44, 46, 48 and 50° C. for 20 min, followed by visualization of reaction products using SDS-PAGE (FIG. 8) and measurement of the proteolytic activity of activated ananain (FIG. 9) as described previously.

High levels of pro-ananain activation and ananain proteolytic activity were observed between 36-40° C. with the highest levels of ananain activity being observed at 37° C. (FIGS. 8 and 9).

Example 2—Activation of Pro-Ananain in Sodium Acetate Buffer

Impact of pH

The reaction mixture was prepared ice-cold with 1 mg/ml pro-ananain at 20 μl per reaction, at a final concentration of 10 mM sodium acetate, 150 mM NaCl and 20 mM freshly added L-Cys. The pH value of the reaction mixture was adjusted to the designated pH value of 3.8, 4.0, 4.5, 5.0, 5.2, 5.3, 5.4, 5.5 and 5.6, respectively. The reaction mixtures were incubated at 37° C. for 20 min, followed by visualization of rection products by SDS-PAGE (FIG. 10) and measurement of the proteolytic activity of activated ananain (FIG. 11) as described previously.

The assay of pro-ananain activation revealed that within the pH range (3.7-5.6) for sodium acetate, pro-ananain activation in 10 mM sodium acetate buffer appeared to prefer pH>5.4 (FIG. 10). Ananain proteolytic activity at pH 5.5 in the sodium acetate buffer was the highest amongst all tested pH values (FIG. 11).

Impact of the Concentration of Sodium Acetate

The reaction mixture was prepared ice-cold with 1 mg/ml pro-ananain at 20 μl per reaction, at a final concentration of 150 mM NaCl and 20 mM freshly added L-Cys, with 3.3, 4.0, 5.0, 6.0, 7.0, 8.0, 9.0, 10.0, 11.0, 12.0, 13.0 and 14.0 mM sodium acetate, respectively, at pH 5.5. The reaction mixtures were incubated at 37° C. for 20 min, followed by visualization of reaction products by SDS-PAGE (FIG. 12)

and measurement of the proteolytic activity of activated ananain (FIG. 13) as described previously.

The highest levels of pro-ananain activation and ananain proteolytic activity were observed in 6-7 mM sodium acetate buffer (FIGS. 12 and 13). For convenience, 6 mM is used for the optimal concentration of sodium acetate buffer.

Impact of the Concentration of L-Cys in Sodium Acetate Buffer

The reaction mixture was prepared ice-cold with 1 mg/ml pro-ananain at 20 μl per reaction, at a final concentration of 6 mM sodium acetate, 150 mM NaCl, pH 5.5, with freshly added L-Cys at a final of 0, 10, 12, 14, 16, 18, 20, 22 and 24 mM, or freshly added ascorbic acid at a final of 0, 5, 10, 15, 20, 30 and 50 mM, respectively. The reaction mixtures were incubated at 37° C. for 20 min, followed by visualization of reaction products by SDS-PAGE (FIG. 14) and measurement of the proteolytic activity of activated ananain (FIG. 15) as described previously.

The results of the pro-ananain activation assay demonstrated that without L-Cys, pro-ananain remained the zymogenic form; i.e., remained inactive (FIG. 14). This assay also showed that at a concentration of L-Cys higher than 14 mM, the active ananain in the phosphate citrate buffer became unstable and was further cleaved into fragments of lower molecular weights, which reflect a loss of ananain proteolytic activity (FIG. 15). Based on the results of the activation assay, the optimal concentration of L-Cys was set to 12 mM for the sodium acetate buffer (FIG. 15). With the same experiment settings, ascorbic acid (up to 50 mM) failed to yield any increase of ananain activity in the activation mixture (FIG. 15).

Pro-Ananain Activation in Sodium Acetate Buffer at Varied Temperature

The reaction mixture was prepared ice-cold with 1 mg/ml pro-ananain at 20 μl per reaction, at a final concentration of 6 mM sodium acetate, 150 mM NaCl, pH 5.5, with freshly added L-Cys at a final of 12 mM. The reaction mixtures were incubated at 0, 22, 24, 26, 28, 30, 32, 34, 36, 37, 38, 40, 42, 44, 46, 48, and 50° C. for 20 min, followed by visualization of reaction products by SDS-PAGE (FIG. 16) and measurement of the proteolytic activity of activated ananain (FIG. 17) as described previously.

The highest activation of pro-ananain to active ananain observed in this assay was at 36-40° C. (FIG. 16). The result of the proteolytic activity assay confirmed that at 37° C., the activation of pro-ananain in the sodium acetate buffer gave the highest level of ananain activity (FIG. 17).

Example 3—Activation of Pro-Ananain in MES Buffer

Impact of pH

The reaction mixture was prepared ice-cold with 1 mg/ml pro-ananain at 20 μl per reaction, at a final concentration of 10 mM MES, 150 mM NaCl and 20 mM freshly added L-Cys. The pH value of the reaction mixture was adjusted to the designated pH value of 5.5, 5.6, 5.7, 5.8, 5.9, 6.0, 6.1 and 6.2, respectively. The reaction mixtures were incubated at 37° C. for 20 min, followed by visualization of reaction products by SDS-PAGE (FIG. 18) and measurement of the proteolytic activity of activated ananain (FIG. 19) as described previously.

The results of the pro-ananain activation assay demonstrated that within the pH range (5.5-6.2) for MES, pro-ananain activation in 10 mM MES buffer appeared to be an event of excessive cleavage (FIG. 18). The 24 kDa band of active ananain was relatively stable when pH>5.8. This agrees with the result of the ananain proteolytic activity assay (FIG. 19), that the activation of pro-ananain in MES at pH 5.8-6.2 yielded the highest ananain activity. Based on these results, pH 6.0 was used for further characterization of the MES conditions.

Impact of the Concentration of MES

The reaction mixture was prepared ice-cold with 1 mg/ml pro-ananain at 20 μl per reaction, at a final concentration of 150 mM NaCl and 20 mM freshly added L-Cys, with 6.0, 7.0, 8.0, 9.0, 10.0, 11.0, 12.0, 13.0, 14.0, 15.0, 16.0, 17.0, 18.0 and 20.0 mM MES, respectively, at pH 6.0. The reaction mixtures were incubated at 37° C. for 20 min, followed by visualization of reaction products by SDS-PAGE (FIG. 20) and measurement of the proteolytic activity of activated ananain (FIG. 21) as described previously.

The results of the pro-ananain activation and ananain proteolytic activity assays showed (FIGS. 20 and 21) that 13-16 mM MES yielded the highest level of pro-ananain activation. For convenience, 15 mM is used as the optimal concentration of MES buffer.

Impact of the Concentration of L-Cys in MES Buffer

The reaction mixture was prepared ice-cold with 1 mg/ml pro-ananain at 20 μl per reaction, at a final concentration of 15 mM MES, 150 mM NaCl, pH 6.0, with freshly added L-Cys at a final of 5, 10, 12, 14, 16, 18, 20, 22, 24, 26 and 30 mM, respectively. The reaction mixtures were incubated at 37° C. for 20 min, followed by visualization of reaction products by SDS-PAGE (FIG. 22) and measurement of the proteolytic activity of activated ananain (FIG. 23) as described previously.

The results from the pro-ananain activation assay showed that at a concentration of L-Cys higher than 20 mM, the active ananain in the MES buffer became unstable and was further cleaved into fragments of lower molecular weights (FIG. 22). This cleavage results in a loss of ananain proteolytic activity (FIG. 23). Based on the results of this assay, the optimal concentration of L-Cys was set to 14 mM for the MES buffer.

Pro-Ananain Activation in MES Buffer at Varied Temperature

The reaction mixture was prepared ice-cold with 1 mg/ml pro-ananain at 20 μl per reaction, at a final concentration of 15 mM MES, 150 mM NaCl, pH 6.0, with freshly added L-Cys at a final of 14 mM. The reaction mixtures were incubated at 22, 24, 26, 28, 30, 32, 34, 36, 37, 38, 40, 42, 44, 46, 48 and 50° C. for 20 min, followed by visualization of reaction products by SDS-PAGE (FIG. 24) and measurement of the proteolytic activity of activated ananain (FIG. 25) as described previously.

The results from this assay showed that in the MES buffer, at 37-40° C., the activation of pro-ananain yielded the highest level of active ananain (FIG. 24). The result of the proteolytic activity assay confirmed that at 37-38° C., the activation of pro-ananain in the MES buffer gave the highest level of ananain activity (FIG. 25).

Example 4—Activation of Pro-Ananain in Sodium Citrate Buffer

Impact of pH

The reaction mixture was prepared ice-cold with 1 mg/ml pro-ananain at 20 μl per reaction, at a final concentration of 10 mM sodium citrate, 150 mM NaCl and 20 mM freshly added L-Cys. The pH value of the reaction mixture was adjusted to the designated pH value of 3.05, 3.10, 3.15, 3.25, 3.35, 3.45, 3.65, 3.95, 4.95, 5.50 and 6.10, respectively. The reaction mixtures were incubated at 37° C. for 20 min, followed by visualization of reaction products by SDS-PAGE (FIG. 26) and measurement of the proteolytic activity of activated ananain (FIG. 27) as described previously.

The results from the pro-ananain activation assay showed that within the pH range (3.0-6.2) for sodium citrate, pro-ananain activation in 10 mM sodium citrate buffer appeared to be an event of excessive cleavage when pH<4 (FIG. 26). The 24 kDa band of active ananain was relatively stable at pH 4.95, although when the pH was >4.95, pro-ananain activation in sodium citrate buffer was poor. This observation agrees with the result of the ananain proteolytic activity assay (FIG. 27) that the activation of pro-ananain in sodium citrate at pH 4.95 yielded the highest ananain activity.

Impact of the Concentration of Sodium Citrate

The reaction mixture was prepared ice-cold with 1 mg/ml pro-ananain at 20 μl per reaction, at a final concentration of 150 mM NaCl and 20 mM freshly added L-Cys, with 1.0, 2.0, 3.0, 4.0, 5.0, 6.0, 7.0, 8.0, 9.0, 10.0, 15.0 and 20.0 mM sodium citrate, respectively, at pH 4.95. The reaction mixtures were incubated at 37° C. for 20 min, followed by visualization of reaction products by SDS-PAGE (FIG. 28) and measurement of the proteolytic activity of activated ananain (FIG. 29) as described previously.

The results from the pro-ananain activation and ananain proteolytic activity assays (FIGS. 28 and 29) showed that 6-8 mM sodium citrate yielded the highest level of pro-ananain activation. For convenience, 8 mM is used as the optimal concentration of sodium citrate buffer.

Impact of the Concentration of L-Cys in Sodium Citrate Buffer

The reaction mixture was prepared ice-cold with 1 mg/ml pro-ananain at 20 μl per reaction, at a final concentration of 8 mM sodium citrate, 150 mM NaCl, pH 4.95, with freshly added L-Cys at a final of 5, 10, 15, 16, 17, 18, 19, 20, 21, 22, 23, 24, 25 and 30 mM, respectively. The reaction mixtures were incubated at 37° C. for 20 min, followed by visualization of reaction products by SDS-PAGE (FIG. 30) and measurement of the proteolytic activity of activated ananain (FIG. 31) as described previously.

The results from the pro-ananain activation and ananain proteolytic activity assays (FIGS. 30 and 31) showed that pro-ananain activation in sodium citrate buffer prefers a concentration of L-Cys at 18-24 mM. For convenience, 22 mM was used as the optimal concentration of L-Cys for the sodium citrate buffer.

Pro-Ananain Activation in Sodium Citrate Buffer at Varied Temperature

The reaction mixture was prepared ice-cold with 1 mg/ml pro-ananain at 20 μl per reaction, at a final concentration of 8 mM sodium citrate, 150 mM NaCl, pH 4.95, with freshly added L-Cys at a final of 22 mM. The reaction mixtures were incubated at 24, 26, 28, 30, 32, 34, 36, 37, 38, 40, 42, 44, 46, 48 and 50° C. for 20 min, followed by visualization of reaction products by SDS-PAGE (FIG. 32) and measurement of the proteolytic activity of activated ananain (FIG. 33) as described previously..

The results from the pro-ananain activation assay showed (FIG. 32) that in the sodium citrate buffer, at 36-38° C., the activation of pro-ananain yielded the highest level of active ananain. The result of the proteolytic activity assay (FIG. 33) confirmed that at 37° C., the activation of pro-ananain in the sodium citrate buffer gave the highest level of ananain activity.

Example 5—Activation of Pro-Ananain in Phosphate Buffered Saline (PBS) Buffer

Impact of pH

The reaction mixture was prepared ice-cold with 1 mg/ml pro-ananain at 20 μl per reaction, in PBS buffer with 20 mM freshly added L-Cys. The pH value of the reaction mixture was adjusted to the designated pH value of 5.80, 5.90, 6.00, 6.20, 6.30, 6.80, 7.00, 7.10, 7.20 and 7.40, respectively. The reaction mixtures were incubated at 37° C. for 20 min, followed by visualization of reaction products by SDS-PAGE (FIG. 34) and measurement of the proteolytic activity of activated ananain (FIG. 35) as described previously.

The pH range of PBS buffer is wide, from weak acidic pH 5.8 to alkalic pH 8.0, including neutral pH, which resembles the pH of human circulatory environment. Therefore, pro-ananain activation in PBS at pH 5.8-7.4 was examined. The results from the pro-ananain activation assay showed that at weak acidic pH 5.8-7.0, pro-ananain activation appeared to be an event of excessive cleavage (FIG. 34). The 24 kDa band of active ananain was relatively stable at pH 7.4 in the test. This result agrees with the result of the ananain proteolytic activity assay (FIG. 35), that the activation of pro-ananain in PBS at pH 7.4 yielded the highest ananain activity.

Impact of the Concentration of L-Cys or Ascorbic Acid in PBS Buffer

The reaction mixture was prepared ice-cold with 1 mg/ml pro-ananain at 20 μl per reaction, in PBS buffer, pH 7.4, with freshly added L-Cys at a final of 0, 5, 10, 11, 12, 13, 14, 15, 16, 17, 18, 19, 25 and 30 mM, or freshly added ascorbic acid at a final of 0, 5, 10, 15, 20, 30 and 50 mM, respectively. The reaction mixtures were incubated at 37° C. for 20 min, followed by visualization of reaction products by SDS-PAGE (FIG. 36) and measurement of the proteolytic activity of activated ananain (FIG. 37) as described previously.

The results from the pro-ananain activation and ananain proteolytic activity assays showed that pro-ananain activation in PBS buffer prefers a concentration of L-Cys at 14-16 mM (FIGS. 36 and 37). For convenience, 15 mM was used as the optimal concentration of L-Cys for PBS buffer. With the same experiment settings, ascorbic acid (up to 50 mM) failed to yield any increase of ananain activity in the activation mixture (FIG. 37).

Pro-Ananain Activation in PBS Buffer at Varied Temperature

The reaction mixture was prepared ice-cold with 1 mg/ml pro-ananain at 20 μl per reaction, PBS buffer, pH 7.4, with freshly added L-Cys at a final of 15 mM. The reaction mixtures were incubated at 22, 24, 26, 28, 30, 32, 34, 36, 37, 38, 40, 42, 44, 46, 48 and 50° C. for 20 min, followed by visualization of reaction products by SDS-PAGE (FIG. 38) and measurement of the proteolytic activity of activated ananain (FIG. 39) as described previously.

The result of the pro-ananain activation assay shows that in PBS buffer, at 36-38° C., the activation of pro-ananain yielded the highest level of active ananain (FIG. 38). The result of the proteolytic activity assay confirmed that at 37° C., the activation of pro-ananain in PBS buffer gave the highest level of ananain activity (FIG. 39).

Example 6—Production of Lyophilized Pro-Ananain Formulations

Lyophilization of Pro-Ananain with Activation Buffers

Recombinant pro-ananain was expressed, unfolded and refolded as described previously. Following the ion-exchange process with a HisTrap™ FastFlow column (GE Health), the recombinant protein was gel-filtrated using a HiLoad™ 16/60 SuperdeX™ 75 column (GE Health) equilibrated with one of the five buffers:

(A) 8 mM Phosphate citrate, 150 mM NaCl, pH 5.5;
(B) 6 mM Sodium acetate, 150 mM NaCl, pH 5.5;
(C) 15 mM 2-(N-morpholino)ethanesulfonic acid (MES), 150 mM NaCl, pH 6.0;
(D) 8 mM Sodium citrate, 150 mM NaCl, pH 4.95;
(E) Phosphate-buffered saline (PBS), pH 7.4.

Pro-ananain in buffer (A)-(E) was adjusted to 1 mg/ml with freshly added L-Cys at a final concentration of 16 mM for buffer (A), 12 mM for buffer (B), 14 mM for buffer (C), 22 mM for buffer (D) and 15 mM for buffer (E), at 4° C., respectively. The mixture was aliquoted into glass vials at 0.5 ml per vial, which was immediately snap frozen in liquid nitrogen. The frozen mixture was subjected to freeze-dry by using a John Morris Alpha 1-2 LDplus Freeze Dryer (NSW, Australia).

Validation of Activation Ofthe Pro-Ananain Formulations

The five lyophilized pro-ananain formulations were resuspended with 0.5 ml water pre-warmed at 37° C. The solutions were incubated at 37° C. for 120 min for a time course examination of active ananain. At every designated time point of 1, 10, 20, 30, 40, 50, 60, 70, 80, 90 and 120 min, a 1 μl of solution was taken to measure proteolytic activity using the PLQ assay described previously.

TABLE 1

Ananain activity of the water reconstituted pro-ananain formulations.

| Formulation | Optimal pH | Maximum activity μg PLQ/min | Maximum activity time | Half-life |
|---|---|---|---|---|
| Phosphate citrate | 5.5 | 0.186 | 50 min | >120 min |
| Sodium acetate | 5.5 | 0.214 | 80 min | >120 min |
| MES | 6.0 | 0.099 | 20 min | 70-80 min |
| Sodium citrate | 4.95 | 0.162 | 20 min | 60 min |
| PBS | 7.4 | 0.132 | 40 min | 120 min |

A summary of ananain activity is shown in Table 1. The results of the ananain proteolytic activity assay (FIG. 40 and Table 1) confirmed the activation of pro-ananain in all five formulations.

Within the first 60 min of activation, the phosphate citrate formulation yielded the highest level of ananain activity, indicating that the phosphate citrate formulation is effective for generating active ananain in a fast manner.

The sodium acetate formulation yielded a lower ananain activity than the phosphate citrate formulation in the first 60 min of activation. However, the phosphate citrate formulation allowed for a continuous increase of ananain activity up to 80 min of activation (FIG. 40). The highest level of ananain proteolytic activity observed amongst all formulations was in the phosphate citrate formulation at 80 min (FIG. 40). Ananain proteolytic activity in the sodium acetate formulation 2 hr after activation process was also higher than the activity observed in the other formulations, indicating that active ananain is the most stable in sodium acetate buffer.

The PBS formulation described herein is particularly advantageous and is likely safe for human use as all of the components of PBS buffer and its neutral pH 7.4 resemble components and the pH found in human circulatory systems. The activation of pro-ananain in the PBS formulation reached a relatively high level of ananain activity at 20 min of activation (FIG. 40). The proteolytic activity of ananain was maintained up to 80 min of activation (FIG. 40).

The sodium citrate formulation yielded similar ananain activity to the phosphate citrate formulation during the first 20 min of activation. However, the proteolytic activity of activated ananain in this formulation quickly dropped after 20 min (FIG. 40). Also observed with the sodium citrate formulation was a decrease in half-life to a half of maximum within 60 min, indicating that active ananain was not stable in the sodium citrate formulation (FIG. 40).

Amongst the five formulations, the MES formulation was the poorest for both ananain activity and stability of ananain.

Example 7—Proteolytic Activity of Ananain Against Human Plasma Proteins

Validation of ananain Activity with Human Plasma Proteins

A vial of lyophilized pro-ananain formulation in phosphate citrate was resuspended with 0.5 ml of 37° C. pre-warmed water and incubated at 37° C. for 20 min for activation of pro-ananain. A 0.18 μg of the activated formulation was mixed with 20 μg of human proteins from:

A. Albumin-partially depleted human plasma;
B. Albumin-fully depleted human plasma;
C. Human plasma;
D. Human serum.

The reaction was prepared in PBS (pH7.4), incubated at 37° C. for 15 min, followed by visualization of reaction products by SDS-PAGE in a 12.5% SDS-gel.

It is a general concern with proteases such as ananain, that in the human circulatory environment, there will be inhibition of proteolytic activity with an attendant loss of function. To demonstrate that ananain can remain active under the conditions found in the human circulatory system, we assayed the proteolytic activity of ananain against human plasma proteins using a phosphate citrate formulation as described herein. The results of this assay showed that that active ananain from the phosphate citrate pro-ananain formulation maintained its proteolytic activity against human plasma proteins at a >1:100 ratio within 15 min (FIG. 41). The clear reduction of albumin in sample A, C and D in the presence of ananain indicates that albumin is a protein substrate for ananain. The cleavage of albumin by ananain results in fragments of varied molecular weights, including fragments in bands 1, 2, 3 and 4 as marked with arrows (FIG. 41). These fragments are not present in sample B, confirming that the source of these fragments is albumin. Besides albumin, high molecular weight human proteins or complexes, bands 5, 6 and 7 as marked with arrows, are also highly likely protein substrates for ananain.

Example 8—a Water-Reconstituted Formulation Generating Active Stem Bromelain

Preparation of Recombinant Pro-Stem Bromelain

Constructing Plasmid Vector for Pro-Stem Bromelain

The coding sequence of recombinant pro-stem bromelain (SB) ((SEQ ID NO: 4) used herein is developed based on UniProt 023799. (SEQ ID NO: 4) excludes the coding sequence for the N-terminal signal sequence of 24 aa, and encodes for an inhibitory sequence of 99 aa (S25-A123 of (SEQ ID NO: 3)) and the active cysteine protease sequence of 233 aa (V124-V356 of (SEQ ID NO: 3)), terminating with a pair of stop codons. The coding sequence was optimized for E co//expression by GeneScript (NJ, USA) using the OptimumGene™ algorithm, and was incorporated into a PUC57 vector with NdeI and BamHI restriction enzyme cleavage sites at the N- and C-terminus, respectively, by GeneScript.

The PUC57-pro-SB construct was digested with NdeI and BamHI restriction enzymes to generate the genetic insert of pro-SB, which was purified after running in a 0.8% agarose gel. The insert was then incorporated into a pET28a plasmid to produce the final pET28a-pro-SB construct, which was amplified in the DH5a *E. coli* strain (Thermo-Fisher, MA, USA). The amplified pET28a-pro-SB construct was extracted using the Wizard DNA Purification kit (Promega, WI, USA), and the gene sequence of the construct was confirmed by Macrogen (Seoul, Korea) (FIG. 42).

Expression, Refolding and Purification of Recombinant Pro-Sb

The method is similar to that for ananain (Refer to previous sessions in the ananain document). The purified pro-SB protein was subjected to size-exclusion chromatography using a HiLoad™ 16/60 Superdex™ 75 column (GE Health) equilibrated with the AMT buffer containing 100 mM sodium acetate, 100 mM MES, 200 mM Tris, 4 mM EDTA and 200 mM NaCl, pH 5.0.

Preparation of Recombinant Pro-Ananain

Recombinant pro-ananain was prepared as previously described herein. The purified pro-ananain protein was subjected to size-exclusion chromatography using a HiLoad™ 16/60 Superdex™ 75 column equilibrated with a buffer containing 6 mM sodium acetate, 150 mM NaCl, pH 5.5.

Activation of Recombinant Pro-Ananain

The concentration of pro-ananain was adjusted to 1 mg/ml in a buffer containing 6 mM sodium acetate, 150 mM NaCl, pH 5.5, with a final concentration of 12 mM L-Cys. The mixture was incubated at 37° C. for 120 min.

The Activation of Pro-SB

In order to examine the cleavage of pro-SB by active ananain, a 40 μg of pro-SB was mixed with 1.6 μg of active ananain, in a final volume of 160 μl of AMT buffer, pH 5.0, with 12 mM L-Cys. The solutions were incubated at room temperature (RT) and at every designated time point of 0, 1, 2, 3, 5, 10 and 15 min, a 20 μl of solution was subjected to SDS-PAGE analysis, as described previously. As control, a sample with 5 μg of pro-SB and another with 0.2 μg of active ananain in 20 μl of AMT buffer with 12 mM L-Cys was respectively incubated at RT for 120 min. The result of SDS-PAGE is shown in FIG. 43.

The results of the above assay demonstrated that, under the experimental setting, neither pro-SB nor active ananain alone were subject to self-cleavage or degradation upon prolonged incubation to 2 hours (FIG. 43). However, mixing active ananain and pro-SB at a weight ratio of 1:25 led to a complete cleavage of pro-SB within 10 min, resulting in two fragments of 24 and 12 kDa, respectively (FIG. 43).

Activity Assay for the Activated Stem Bromelain

In order to demonstrate the proteolytic activity of activated SB without interfering by ananain, 2 mg of active ananain was immobilized in a 5 ml HiTrap™ NHS-Activated HP affinity column (GE Health, IL, USA). 5 mg of pro-SB was resuspended in 5 ml AMT buffer, pH 5.0, with 12 mM L-Cys. The pro-SB was circulated through the ananain-immobilized column at RT for overnight. The collected activated SB was subject to SDS-PAGE analysis and was confirmed to be fully activated (FIG. 44).

Proteolytic activity of SB was measured using a fluorescent tripeptidyl substrate, PRR, in the form of MeOC-GGG-PRR-GG-DPA-KK-$NH_2$ (SEQ ID NO: 8) (Mimotopes, Clayton, Australia). Typically, following the activation process, 100 nM of activated SB was mixed with a final concentration of 25 μM of PRR in a final volume of 100 μl AAB. Cleavage at the core PRR tripeptide releases the fluorescence of the MeOC donor group, which is detected by using a POLARstar fluorescent plate reader, as described previously. The initial rate of proteolysis of PRR by 100 nM active SB was measured as the slope of the linear portion of the progressive curve and determined to be about 0.024 μg PRR molecules per min, whilst the cleavage of PRR by 100 nM Pro-SB was negligible (FIG. 45).

Example 9—a Water-Reconstituted Formulation Generating Active Fruit Bromelain

Preparation of Recombinant Pro-Fruit Bromelain

Constructing Plasmid Vector for Pro-Fruit Bromelain

The coding sequence of pro-fruit bromelain (FB) disclosed herein (SEQ ID NO: 6) was developed based on NCBI Reference Sequence XP_020089244.1. The coding sequence excludes the nucleotides coding for the N-terminal signal sequence of 25 aa. The pro-FB-coding region encodes for an inhibitory sequence of 101 aa (S26-S126 of (SEQ ID NO: 5)) and the active cysteine protease sequence of 235 aa (K127-I361 of (SEQ ID NO: 5)), and is terminated by a stop codon. NdeI and an EcoRI restriction enzyme cleavage sites were added at the N- and C-terminus of the coding region, respectively. The coding sequence was optimized for *E. coli* expression and purchased from GeneScript NJ, USA), and was incorporated into a pET28a vector. The gene sequence of the construct was confirmed by Macrogen (Seoul, Korea) (FIG. 46).

Expression, Refolding and Purification of Recombinant pro-fb

The method is similar to that for ananain (Refer to previous sessions in the ananain document). The purified pro-FB protein was subjected to size-exclusion chromatography using a HiLoad™ 16/60 Superdex™ 75 column (GE Health) equilibrated with the AMT buffer containing 100 mM sodium acetate, 100 mM MES, 200 mM Tris, 4 mM EDTA and 200 mM NaCl, pH 5.0.

Preparation of Recombinant Pro-Ananain

Recombinant pro-ananain was prepared as previously described herein. The purified pro-ananain protein was subjected to size-exclusion chromatography using a HiLoad™ 16/60 Superdex™ 75 column equilibrated with a buffer containing 6 mM sodium acetate, 150 mM NaCl, pH 5.5.

Activation of Recombinant Pro-Ananain

The concentration of pro-ananain was adjusted to 1 mg/ml in a buffer containing 6 mM sodium acetate, 150 mM NaCl, pH 5.5, with a final concentration of 12 mM L-Cys. The mixture was incubated at 37° C. for 120 min.

The Activation of Pro-FB 2 mg of active ananain was immobilized in a 5 ml HiTrap™ NHS-Activated HP affinity column (GE Health, IL, USA). 5 mg of pro-FB was resuspended in 5 ml AMT buffer, pH 5.0, with 12 mM L-Cys. The pro-FB was circulated through the ananain-immobilized column at RT for overnight. The collected activated FB was subject to SDS-PAGE analysis and was confirmed to be fully activated (FIG. 47).

Activity Assay for the Activated Fruit Bromelain

Activity of FB was measured using a fluorescent tripeptidyl substrate, FVR-7-amino-4-methylcoumarin (FVR-AMC). Typically, following the activation process, 10 nM of activated FB was mixed with a final concentration of 50 μM of FVR-AMC in a final volume of 100 μl AAB buffer, pH 4.0. Cleavage of FVR-AMC releases the fluorescent AMC group, which is detected by using a POLARstar fluorescent plate reader, using excitation and emission wavelengths of 360 and 460 nm, respectively. The initial rate of proteolysis of FVR-AMC by 10 nM active FB was estimated to be around 0.048 μM FVR-AMC per min (or 0.0033 μg FVR-AMC per 100 μl per min) whilst pro-FB did not cleave FVR-AMC at all.

CONCLUSIONS

Disclosed herein is the inventor's development of a pure and stable composition for the major cysteine proteases, ananain, stem bromelain and fruit bromelain, from *Ananus comosus*. The compositions described herein utilize recombinantly produced proteases in their inactive pro-enzyme form which enables stable formulation for prolonged storage. This approach not only avoids the technical difficulties in protein separation, activity discrimination and enzyme quantification when using natural proteases from the pineapple plants, but also provides a useful tool for future development of combinations of different pineapple proteases at particular ratios designed to achieve specific outcomes; e.g., based on the different proteolytic functions of these proteases. Also described herein are the conditions for the auto-activation of pro-ananain and the trans-activation of pro-stem bromelain/pro-fruit bromelain by ananain. These activation conditions have been optimised to physiological conditions for human and animal use. The inventor's work also described herein further provides a powder form of stabilized inactive enzymes in an activation formula. The formulated products can effectively avoid unnecessary enzyme activation/degradation due to temperature changes in storage, transport and handling. A water-reconstituted formula of pro-ananain comprised in a composition as described herein has proved to be an easy and effective way to achieve the fast activation and lasting proteolytic activity of ananain.

Amino Acid and Nucleic Acid Sequences

```
Pro-ananain AA Sequence
                                          (SEQ ID NO: 1)
SCDEPSDPMMKQFEEWMAEYGRVYKDNDEKMLRFQIFKNNVNHIETFNN

RNGNSYTLGINQFTDMTNNEFVAQYTGLSLPLNIKREPVVSFDDVDISS

VPQSIDWRDSGAVTSVKNQGRCGSCWAFASIATVESIYKIKRGNLVSLS

EQQVLDCAVSYGCKGGWINKAYSFIISNKGVASAATYPYKAAKGTCKTN

GVPNSAYITRYTYVQRNNERNMMYAVSNQPIAAALDASGNFQHYKRGVF

TGPCGTRLNHAIVIIGYGQDSSGKKFWIVRNSWGAGWGEGGYIRLARDV

SSSFGLCGIAMDPLYPTLQSGPSVEVI

Pro-ananain Gene Sequence
                                          (SEQ ID NO: 2)
AGCTGCGATGAGCCGAGCGACCCGATGATGAAACAATTTGAAGAGTGGA

TGGCGGAGTATGGCCGTGTGTATAAGGATAACGACGAGAAGATGCTGCG

TTTCCAGATTTTCAAAAACAACGTTAACCACATCGAAACCTTCAACAAC

CGTAACGGCAACAGCTACACCCTGGGTATTAACCAGTTCACCGACATGA

CCAACAACGAGTTTGTGGCGCAATATACCGGTCTGAGCCTGCCGCTGAA

CATCAAGCGTGAACCGGTGGTTAGCTTCGACGATGTGGACATCAGCAGC

GTGCCGCAGAGCATTGACTGGCGTGATAGCGGCGCGGTGACCAGCGTTA
```

-continued

```
AAAACCAAGGCCGTTGCGGTAGCTGCTGGGCGTTTGCGAGCATTGCGAC

CGTGGAGAGCATCTACAAGATTAAACGTGGCAACCTGGTTAGCCTGAGC

GAACAGCAAGTGCTGGACTGCGCGGTTAGCTACGGTTGCAAGGGTGGCT

GGATTAACAAAGCGTATAGCTTTATCATTAGCAACAAGGGCGTTGCGAG

CGCGGCGATCTACCCGTATAAGGCGGCGAAAGGCACCTGCAAAACCAAC

GGTGTGCCGAACAGCGCGTACATTACCCGTTACACCTATGTTCAACGTA

ACAACGAGCGTAACATGATGTATGCGGTGAGCAACCAACCGATTGCGGC

GGCGCTGGACGCGAGCGGCAACTTCCAACACTACAAGCGTGGTGTTTTT

ACCGGTCCGTGCGGCACCCGTCTGAACCACGCGATCGTGATCATTGGTT

ATGGCCAGGATAGCAGCGGTAAGAAATTCTGGATCGTTCGTAACAGCTG

GGGTGCGGGTTGGGGTGAAGGTGGCTACATTCGTCTGGCGCGTGACGTG

AGCAGCAGCTTCGGCCTGTGCGGTATCGCGATGGACCCGCTGTATCCGA

CCCTGCAAAGCGGTCCGAGCGTTGAGGTTATC

Pro-stem bromelain AA Sequence
                                          (SEQ ID NO: 3)
SADEPSDPMMKRFEEWMVEYGRVYKDNDEKMRRFQIFKNNVNHIETENS

RNENSYTLGINQFTDMTNNEFIAQYTGGISRPLNIEREPVVSFDDVDIS

AVPQSIDWRDYGAVTSVKNQNPCGACWAFAAIATVESIYKIKKGILEPL

SEQQVLDCAKGYGCKGGWEFRAFEFIISNKGVASGAIYPYKAAKGTCKT

NGVPNSAYITGYARVPRNNESSMMYAVSKQPITVAVDANANFQYYKSGV

FNGPCGTSLNHAVTAIGYGQDSNGKKYWIVKNSWGARWGEAGYIRMARD

VSSSSGICGIAIDSLYPTLESRANVEAIKMVSESRSSV

Pro-stem bromelain Gene Sequence
                                          (SEQ ID NO: 4)
AGCGCGGACGAGCCGAGCGACCCGATGATGAAGCGTTTTGAAGAGTGGA

TGGTGGAGTATGGCCGTGTGTATAAAGATAATGACGAGAAGATGCGTCG

TTTCCAGATTTTCAAAAACAACGTTAACCACATCGAAACCTTCAACAGC

CGTAACGAAAACAGCTACACCCTGGGTATCAACCAGTTCACCGACATGA

CCAACAACGAGTTTATTGCGCAATATACCGGTGGCATCAGCCGTCCGCT

GAACATTGAGCGTGAACCGGTGGTTAGCTTCGACGATGTGGACATCAGC

GCGGTTCCGCAGAGCATTGACTGGCGTGATTACGGTGCGGTGACCAGCG

TTAAGAACCAAAACCCGTGCGGTGCGTGCTGGGCGTTTGCGGCGATCGC

GACCGTTGAAAGCATCTACAAGATTAAGAAAGGTATTCTGGAGCCGCTG

AGCGAACAGCAAGTGCTGGACTGCGCGAAGGGTTATGGCTGCAAAGGTG

GCTGGGAGTTTCGTGCGTTCGAATTTATCATTAGCAACAAGGGTGTGGC

GAGCGGCGCGATCTACCCGTATAAGGCGGCGAAAGGCACCTGCAAAACC

AACGGCGTGCCGAACAGCGCGTACATTACCGGTTATGCGCGTGTTCCGC

GTAACAACGAGAGCAGCATGATGTACGCGGTGAGCAAGCAGCCGATCAC

CGTGGCGGTTGACGCGAACGCGAACTTCCAATACTATAAAAGCGGCGTT

TTTAACGGTCCGTGCGGCACCAGCCTGAACCATGCGGTGACCGCGATCG

GTTACGGCCAAGATAGCAACGGTAAGAAATATTGGATTGTTAAGAACAG

CTGGGGCGCGCGTTGGGGTGAAGCGGGCTACATCCGTATGGCGCGTGAC

GTGAGCAGCAGCAGCGGTATTTGCGGCATCGCGATTGATAGCCTGTATC
```

-continued

CGACCCTGGAGAGCCGTGCGAACGTGGAAGCGATCAAAATGGTTAGCGA

AAGCCGCAGCAGCGTT

Pro-fruit bromelain AA Sequence (SEQ ID NO: 5)

SPLASCGOSDAHMMTRFEDWMRQYGRVYDSEDEKSLRFEIFKNNVNHIE

TENSRNENSYTLGINQFADMTNEEFVARYAGTFFPQNIESEPTASLEDV

DLSKLPDSIDWRQKGAVTEVKNQGECGSCWAFSAVATVEGLYKIKKGNL

LDLSEQEVLDCADSVECIGGWVQNAYKFIISNKGVTNEKSYPYVGTKGS

CAAKGKPNVAYITGYEFLPAFDEGTMMAAVAQQPITSAVDTKNKNFQFY

NGGVFKGPCGTRIDHAITIVGYGKDSSGTQYWLIKNSWGKTWGESGYLR

LQKGSGTLRGACGIAQYVLRPLLNSKATAQLSDTGSDGLSSI

Pro-fruit bromelain Gene Sequence (SEQ ID NO: 6)

TCGCCACTCGCCTCTTGCGGCCAATCGGATGCTCACATGATGACGAGGT

TCGAAGATTGGATGAGACAATATGGCCGAGTTTACGACAGTGAAGACGA

GAAGTCCCTCCGTTTTGAGATCTTTAAGAACAACGTGAACCATATCGAA

ACCTTCAATAGCCGCAACGAAAACTCGTACACTCTCGGCATTAATCAAT

TCGCTGATATGACAAATGAAGAATTCGTTGCGCGATACGCTGGTACGTT

CTTCCCTCAAAATATTGAATCGGAGCCAACTGCATCGCTTGAGGACGTA

GACTTGTCCAAACTGCCTGATAGTATTGATTGGAGGCAGAAAGGTGCCG

TCACGGAAGTCAAGAATCAAGGCGAATGCGGTTCATGCTGGGCGTTCAG

TGCAGTTGCGACAGTAGAAGGGCTCTACAAGATCAAAAAGGGAAACTTG

TTAGATCTATCTGAACAAGAAGTTTTAGACTGCGCCGACAGCGTCGAGT

GCATAGGTGGTTGGGTGCAGAATGCCTACAAATTCATCATATCTAATAA

AGGTGTGACAAATGAAAAGAGCTACCCTTATGTGGGAACCAAAGGCAGT

-continued

TGCGCCGCAAAGGGCAAACCCAACGTAGCATATATTACTGGTTACGAAT

TTCTGCCTGCGTTTGACGAAGGCACCATGATGGCTGCCGTGGCGCAGCA

ACCGATAACTTCCGCCGTCGATACGAAAAACAAGAACTTTCAGTTTTAC

AATGGCGGCGTGTTTAAAGGACCTTGCGGGACAAGGATTGACCACGCCA

TCACCATTGTAGGGTACGGGAAAGACAGCAGCGGAACACAGTATTGGTT

AATTAAGAACTCATGGGGCAAAACGTGGGGCGAGAGCGGGTACTTGAGG

CTGCAAAAGGGCTCCGGAACATTACGCGGAGCATGTGGGATCGCCCAGT

ATGTCCTCCGTCCGCTTCTGAATTCGAAGGCAACCGCCCAACTCTCTGA

CACGGGGTCTGATGGTTTAAGTTCGATC

REFERENCES

Yongqing T, Wilmann P G, Pan J, West M L, Brown T J, Mynott T, Pike R N, Wijeyewickrema L C (2019) Determination of the Crystal Structure and Substrate Specificity of Ananain. *Biochimie.* 166:194-202.

Orgill D P, Liu P Y, Ritterbush L S, Skrabut E M, Samuels J A, Shames S L (1996) Debridement of Porcine Burns With a Highly Purified, Ananain-Based Cysteine Protease Preparation. *J Burn Care Rehabil*. July-August 1996; 17(4):311-22.

Verma S, Dixit R, Pandey K C. (2016) Cysteine Proteases: Modes of Activation and Future Prospects as Pharmacological Targets. *Front Pharmacol.* 7:107.

Matagne A, Bolle L, El Mahyaoui R, Baeyens-Volant D, Azarkan M. (2017) The proteolytic system of pineapple stems revisited: Purification and characterization of multiple catalytically active forms. *Phytochemistry* 138:29-51.

Carter, C. E., Marriage, H., Goodenough, P. W. (2000) Mutagenesis and Kinetic Studies of a Plant Cysteine Proteinase with an Unusual Arrangement of Acidic Amino Acids in and around the Active Site. *Biochemistry* 39, 36, 11005-11013.

What we claim is:

1. A composition comprising:

(a) recombinant pro-ananain (b) a pharmaceutically acceptable buffer (c) a pharmaceutically acceptable reducing agent, and (d) sodium chloride (NaCl), wherein the concentration of the buffer is about 5 to about 30 mM, wherein the concentration of the reducing agent is about 10 to about 30 mM, wherein the concentration of the NaCl is about 140 to about 160 mM and wherein the pH of the composition is about 5.0 to about 6.0.

2. The composition of claim 1 wherein the recombinant pro-ananain comprises a polypeptide comprising at least 70% amino acid identity to SEQ ID NO: 1.

3. The composition of claim 1 wherein the recombinant pro-ananain comprises SEQ ID NO: 1.

4. The composition of claim 1 wherein the buffer is selected from the group consisting of phosphate-citrate, sodium acetate, sodium citrate and 2-(N-morpholino)ethanesulfonic acid (MES) buffers.

5. The composition of claim 4 wherein the buffer is phosphate-citrate at a concentration of about 5 mM to about 20 mM.

6. The composition of claim 1 wherein the reducing agent is L-cysteine (L-Cys).

7. The composition of claim 6 comprising about 8 mM phosphate-citrate buffer and about 10 mM to about 30 mM L-Cys.

8. The composition of claim 1 wherein the buffer is phosphate buffered saline (PBS) and wherein the composition comprises about 8 mM to about 22 mM L-Cys, preferably about 15 mM L-Cys.

9. The composition of claim 1 comprising about 150 mM NaCl.

10. The composition of claim 1 having a pH of about 5.1 to about 5.9.

11. The composition of claim 1 that is an aqueous composition.

12. The composition of claim 1 that is a dry composition.

13. The composition of claim 12 that is a lyophilized composition.

14. The composition of claim 1 that further comprises (e) pro-bromelain.

15. The composition of claim 14 wherein the pro-bromelain is at a ratio of pro-ananain:pro-bromelain of about 1:25 to about 1:50.

16. A method of providing a recombinant active ananain composition, the method comprising heating an aqueous composition as defined in claim 11 to about 30° C. to about 44° C. for at least 5 min.

17. The method of claim 16 wherein the aqueous composition is a lyophilized dry composition that has been reconstituted in water or buffer.

18. The method of claim 16 wherein heating is for about 5 min to about 30 min.

* * * * *

SEQUENCE LISTING

```
<160> NUMBER OF SEQ ID NOS: 8

<210> SEQ ID NO 1
<211> LENGTH: 321
<212> TYPE: PRT
<213> ORGANISM: Artificial Sequence
<220> FEATURE:
<223> OTHER INFORMATION: The sequence is artificially synthesized

<400> SEQUENCE: 1

Ser Cys Asp Glu Pro Ser Asp Pro Met Met Lys Gln Phe Glu Glu Trp
1               5                   10                  15

Met Ala Glu Tyr Gly Arg Val Tyr Lys Asp Asn Asp Glu Lys Met Leu
            20                  25                  30

Arg Phe Gln Ile Phe Lys Asn Asn Val Asn His Ile Glu Thr Phe Asn
        35                  40                  45

Asn Arg Asn Gly Asn Ser Tyr Thr Leu Gly Ile Asn Gln Phe Thr Asp
    50                  55                  60

Met Thr Asn Asn Glu Phe Val Ala Gln Tyr Thr Gly Leu Ser Leu Pro
65                  70                  75                  80

Leu Asn Ile Lys Arg Glu Pro Val Val Ser Phe Asp Asp Val Asp Ile
```

```
                85                  90                  95

Ser Ser Val Pro Gln Ser Ile Asp Trp Arg Asp Ser Gly Ala Val Thr
            100                 105                 110

Ser Val Lys Asn Gln Gly Arg Cys Gly Ser Cys Trp Ala Phe Ala Ser
        115                 120                 125

Ile Ala Thr Val Glu Ser Ile Tyr Lys Ile Lys Arg Gly Asn Leu Val
    130                 135                 140

Ser Leu Ser Glu Gln Gln Val Leu Asp Cys Ala Val Ser Tyr Gly Cys
145                 150                 155                 160

Lys Gly Gly Trp Ile Asn Lys Ala Tyr Ser Phe Ile Ile Ser Asn Lys
                165                 170                 175

Gly Val Ala Ser Ala Ala Ile Tyr Pro Tyr Lys Ala Ala Lys Gly Thr
            180                 185                 190

Cys Lys Thr Asn Gly Val Pro Asn Ser Ala Tyr Ile Thr Arg Tyr Thr
        195                 200                 205

Tyr Val Gln Arg Asn Asn Glu Arg Asn Met Met Tyr Ala Val Ser Asn
    210                 215                 220

Gln Pro Ile Ala Ala Ala Leu Asp Ala Ser Gly Asn Phe Gln His Tyr
225                 230                 235                 240

Lys Arg Gly Val Phe Thr Gly Pro Cys Gly Thr Arg Leu Asn His Ala
                245                 250                 255

Ile Val Ile Ile Gly Tyr Gly Gln Asp Ser Ser Gly Lys Lys Phe Trp
            260                 265                 270

Ile Val Arg Asn Ser Trp Gly Ala Gly Trp Gly Glu Gly Gly Tyr Ile
        275                 280                 285

Arg Leu Ala Arg Asp Val Ser Ser Ser Phe Gly Leu Cys Gly Ile Ala
    290                 295                 300

Met Asp Pro Leu Tyr Pro Thr Leu Gln Ser Gly Pro Ser Val Glu Val
305                 310                 315                 320

Ile


<210> SEQ ID NO 2
<211> LENGTH: 963
<212> TYPE: DNA
<213> ORGANISM: Artificial Sequence
<220> FEATURE:
<223> OTHER INFORMATION: The sequence is artificially synthesized

<400> SEQUENCE: 2

agctgcgatg agccgagcga cccgatgatg aaacaatttg aagagtggat ggcggagtat      60

ggccgtgtgt ataaggataa cgacgagaag atgctgcgtt tccagatttt caaaaacaac     120

gttaaccaca tcgaaacctt caacaaccgt aacggcaaca gctacaccct gggtattaac     180

cagttcaccg acatgaccaa caacgagttt gtggcgcaat ataccggtct gagcctgccg     240

ctgaacatca agcgtgaacc ggtggttagc ttcgacgatg tggacatcag cagcgtgccg     300

cagagcattg actggcgtga tagcggcgcg gtgaccagcg ttaaaaacca aggccgttgc     360

ggtagctgct gggcgtttgc gagcattgcg accgtggaga gcatctacaa gattaaacgt     420

ggcaacctgg ttagcctgag cgaacagcaa gtgctggact gcgcggttag ctacggttgc     480

aagggtggct ggattaacaa agcgtatagc tttatcatta gcaacaaggg cgttgcgagc     540

gcggcgatct acccgtataa ggcggcgaaa ggcacctgca aaaccaacgg tgtgccgaac     600

agcgcgtaca ttacccgtta cacctatgtt caacgtaaca acgagcgtaa catgatgtat     660

gcggtgagca accaaccgat tgcggcggcg ctggacgcga gcggcaactt ccaacactac     720
```

```
aagcgtggtg tttttaccgg tccgtgcggc acccgtctga accacgcgat cgtgatcatt    780

ggttatggcc aggatagcag cggtaagaaa ttctggatcg ttcgtaacag ctggggtgcg    840

ggttggggtg aaggtggcta cattcgtctg gcgcgtgacg tgagcagcag cttcggcctg    900

tgcggtatcg cgatggaccc gctgtatccg accctgcaaa gcggtccgag cgttgaggtt    960

atc                                                                  963


<210> SEQ ID NO 3
<211> LENGTH: 332
<212> TYPE: PRT
<213> ORGANISM: Artificial Sequence
<220> FEATURE:
<223> OTHER INFORMATION: The sequence is artificially synthesized

<400> SEQUENCE: 3

Ser Ala Asp Glu Pro Ser Asp Pro Met Met Lys Arg Phe Glu Glu Trp
1               5                   10                  15

Met Val Glu Tyr Gly Arg Val Tyr Lys Asp Asn Asp Glu Lys Met Arg
            20                  25                  30

Arg Phe Gln Ile Phe Lys Asn Asn Val Asn His Ile Glu Thr Phe Asn
        35                  40                  45

Ser Arg Asn Glu Asn Ser Tyr Thr Leu Gly Ile Asn Gln Phe Thr Asp
    50                  55                  60

Met Thr Asn Asn Glu Phe Ile Ala Gln Tyr Thr Gly Gly Ile Ser Arg
65                  70                  75                  80

Pro Leu Asn Ile Glu Arg Glu Pro Val Val Ser Phe Asp Asp Val Asp
                85                  90                  95

Ile Ser Ala Val Pro Gln Ser Ile Asp Trp Arg Asp Tyr Gly Ala Val
            100                 105                 110

Thr Ser Val Lys Asn Gln Asn Pro Cys Gly Ala Cys Trp Ala Phe Ala
        115                 120                 125

Ala Ile Ala Thr Val Glu Ser Ile Tyr Lys Ile Lys Lys Gly Ile Leu
    130                 135                 140

Glu Pro Leu Ser Glu Gln Gln Val Leu Asp Cys Ala Lys Gly Tyr Gly
145                 150                 155                 160

Cys Lys Gly Gly Trp Glu Phe Arg Ala Phe Glu Phe Ile Ile Ser Asn
                165                 170                 175

Lys Gly Val Ala Ser Gly Ala Ile Tyr Pro Tyr Lys Ala Ala Lys Gly
            180                 185                 190

Thr Cys Lys Thr Asn Gly Val Pro Asn Ser Ala Tyr Ile Thr Gly Tyr
        195                 200                 205

Ala Arg Val Pro Arg Asn Asn Glu Ser Ser Met Met Tyr Ala Val Ser
    210                 215                 220

Lys Gln Pro Ile Thr Val Ala Val Asp Ala Asn Ala Asn Phe Gln Tyr
225                 230                 235                 240

Tyr Lys Ser Gly Val Phe Asn Gly Pro Cys Gly Thr Ser Leu Asn His
                245                 250                 255

Ala Val Thr Ala Ile Gly Tyr Gly Gln Asp Ser Asn Gly Lys Lys Tyr
            260                 265                 270

Trp Ile Val Lys Asn Ser Trp Gly Ala Arg Trp Gly Glu Ala Gly Tyr
        275                 280                 285

Ile Arg Met Ala Arg Asp Val Ser Ser Ser Ser Gly Ile Cys Gly Ile
    290                 295                 300

Ala Ile Asp Ser Leu Tyr Pro Thr Leu Glu Ser Arg Ala Asn Val Glu
```

305 310 315 320

Ala Ile Lys Met Val Ser Glu Ser Arg Ser Ser Val
325 330

<210> SEQ ID NO 4
<211> LENGTH: 996
<212> TYPE: DNA
<213> ORGANISM: Artificial Sequence
<220> FEATURE:
<223> OTHER INFORMATION: The sequence is artificially synthesized

<400> SEQUENCE: 4
agcgcggacg agccgagcga cccgatgatg aagcgttttg aagagtggat ggtggagtat 60
ggccgtgtgt ataaagataa tgacgagaag atgcgtcgtt tccagatttt caaaaacaac 120
gttaaccaca tcgaaacctt caacagccgt aacgaaaaca gctacaccct gggtatcaac 180
cagttcaccg acatgaccaa caacgagttt attgcgcaat ataccggtgg catcagccgt 240
ccgctgaaca ttgagcgtga accggtggtt agcttcgacg atgtggacat cagcgcggtt 300
ccgcagagca ttgactggcg tgattacggt gcggtgacca gcgttaagaa ccaaaacccg 360
tgcggtgcgt gctgggcgtt tgcggcgatc gcgaccgttg aaagcatcta caagattaag 420
aaaggtattc tggagccgct gagcgaacag caagtgctgg actgcgcgaa gggttatggc 480
tgcaaaggtg gctgggagtt tcgtgcgttc gaatttatca ttagcaacaa gggtgtggcg 540
agcggcgcga tctacccgta taaggcggcg aaaggcacct gcaaaaccaa cggcgtgccg 600
aacagcgcgt acattaccgg ttatgcgcgt gttccgcgta acaacgagag cagcatgatg 660
tacgcggtga gcaagcagcc gatcaccgtg gcggttgacg cgaacgcgaa cttccaatac 720
tataaaagcg gcgtttttaa cggtccgtgc ggcaccagcc tgaaccatgc ggtgaccgcg 780
atcggttacg gccaagatag caacggtaag aaatattgga ttgttaagaa cagctggggc 840
gcgcgttggg gtgaagcggg ctacatccgt atggcgcgtg acgtgagcag cagcagcggt 900
atttgcggca tcgcgattga tagcctgtat ccgaccctgg agagccgtgc gaacgtggaa 960
gcgatcaaaa tggttagcga aagccgcagc agcgtt 996

<210> SEQ ID NO 5
<211> LENGTH: 336
<212> TYPE: PRT
<213> ORGANISM: Artificial Sequence
<220> FEATURE:
<223> OTHER INFORMATION: The sequence is artificially synthesized

<400> SEQUENCE: 5

Ser Pro Leu Ala Ser Cys Gly Gln Ser Asp Ala His Met Met Thr Arg
1 5 10 15

Phe Glu Asp Trp Met Arg Gln Tyr Gly Arg Val Tyr Asp Ser Glu Asp
20 25 30

Glu Lys Ser Leu Arg Phe Glu Ile Phe Lys Asn Asn Val Asn His Ile
35 40 45

Glu Thr Phe Asn Ser Arg Asn Glu Asn Ser Tyr Thr Leu Gly Ile Asn
50 55 60

Gln Phe Ala Asp Met Thr Asn Glu Glu Phe Val Ala Arg Tyr Ala Gly
65 70 75 80

Thr Phe Phe Pro Gln Asn Ile Glu Ser Glu Pro Thr Ala Ser Leu Glu
85 90 95

Asp Val Asp Leu Ser Lys Leu Pro Asp Ser Ile Asp Trp Arg Gln Lys
100 105 110

```
Gly Ala Val Thr Glu Val Lys Asn Gln Gly Glu Cys Gly Ser Cys Trp
        115                 120                 125

Ala Phe Ser Ala Val Ala Thr Val Glu Gly Leu Tyr Lys Ile Lys Lys
    130                 135                 140

Gly Asn Leu Leu Asp Leu Ser Glu Gln Glu Val Leu Asp Cys Ala Asp
145                 150                 155                 160

Ser Val Glu Cys Ile Gly Gly Trp Val Gln Asn Ala Tyr Lys Phe Ile
                165                 170                 175

Ile Ser Asn Lys Gly Val Thr Asn Glu Lys Ser Tyr Pro Tyr Val Gly
            180                 185                 190

Thr Lys Gly Ser Cys Ala Ala Lys Gly Lys Pro Asn Val Ala Tyr Ile
        195                 200                 205

Thr Gly Tyr Glu Phe Leu Pro Ala Phe Asp Glu Gly Thr Met Met Ala
    210                 215                 220

Ala Val Ala Gln Gln Pro Ile Thr Ser Ala Val Asp Thr Lys Asn Lys
225                 230                 235                 240

Asn Phe Gln Phe Tyr Asn Gly Gly Val Phe Lys Gly Pro Cys Gly Thr
                245                 250                 255

Arg Ile Asp His Ala Ile Thr Ile Val Gly Tyr Gly Lys Asp Ser Ser
            260                 265                 270

Gly Thr Gln Tyr Trp Leu Ile Lys Asn Ser Trp Gly Lys Thr Trp Gly
        275                 280                 285

Glu Ser Gly Tyr Leu Arg Leu Gln Lys Gly Ser Gly Thr Leu Arg Gly
    290                 295                 300

Ala Cys Gly Ile Ala Gln Tyr Val Leu Arg Pro Leu Leu Asn Ser Lys
305                 310                 315                 320

Ala Thr Ala Gln Leu Ser Asp Thr Gly Ser Asp Gly Leu Ser Ser Ile
                325                 330                 335
```

<210> SEQ ID NO 6
<211> LENGTH: 1008
<212> TYPE: DNA
<213> ORGANISM: Artificial Sequence
<220> FEATURE:
<223> OTHER INFORMATION: The sequence is artificially synthesized

<400> SEQUENCE: 6

```
tcgccactcg cctcttgcgg ccaatcggat gctcacatga tgacgaggtt cgaagattgg     60

atgagacaat atggccgagt ttacgacagt gaagacgaga agtccctccg ttttgagatc    120

tttaagaaca acgtgaacca tatcgaaacc ttcaatagcc gcaacgaaaa ctcgtacact    180

ctcggcatta atcaattcgc tgatatgaca aatgaagaat tcgttgcgcg atacgctggt    240

acgttcttcc ctcaaaatat tgaatcggag ccaactgcat cgcttgagga cgtagacttg    300

tccaaactgc ctgatagtat tgattggagg cagaaaggtg ccgtcacgga agtcaagaat    360

caaggcgaat gcggttcatg ctgggcgttc agtgcagttg cgacagtaga agggctctac    420

aagatcaaaa agggaaactt gttagatcta tctgaacaag aagttttaga ctgcgccgac    480

agcgtcgagt gcataggtgg ttgggtgcag aatgcctaca aattcatcat atctaataaa    540

ggtgtgacaa atgaaaagag ctacccttat gtgggaacca aaggcagttg cgccgcaaag    600

ggcaaaccca acgtagcata tattactggt tacgaatttc tgcctgcgtt tgacgaaggc    660

accatgatgg ctgccgtggc gcagcaaccg ataacttccg ccgtcgatac gaaaaacaag    720

aactttcagt tttacaatgg cggcgtgttt aaaggacctt gcgggacaag gattgaccac    780
```

-continued

```
gccatcacca ttgtagggta cgggaaagac agcagcggaa cacagtattg gttaattaag    840

aactcatggg gcaaaacgtg gggcgagagc gggtacttga ggctgcaaaa gggctccgga    900

acattacgcg gagcatgtgg gatcgcccag tatgtcctcc gtccgcttct gaattcgaag    960

gcaaccgccc aactctctga cacggggtct gatggtttaa gttcgatc                1008


<210> SEQ ID NO 7
<211> LENGTH: 10
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MISC_FEATURE
<222> LOCATION: (8)..(9)
<223> OTHER INFORMATION: DPA quencher is present between Glycine and
      Lysine residues

<400> SEQUENCE: 7

Gly Gly Gly Pro Leu Gln Gly Gly Lys Lys
1               5                   10


<210> SEQ ID NO 8
<211> LENGTH: 10
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MISC_FEATURE
<222> LOCATION: (8)..(9)
<223> OTHER INFORMATION: DPA quencher is present between Glycine and
      Lysine residues

<400> SEQUENCE: 8

Gly Gly Gly Pro Arg Arg Gly Gly Lys Lys
1               5                   10
```